US009061001B2

(12) United States Patent
van Drunen Littel-van den Hurk et al.

(10) Patent No.: US 9,061,001 B2
(45) Date of Patent: *Jun. 23, 2015

(54) COMBINATION ADJUVANT FORMULATION

(75) Inventors: Sylvia van Drunen Littel-van den Hurk, Saskatoon (CA); Volker Gerdts, Saskatoon (CA); Andrew Potter, Saskatoon (CA); Lorne Babiuk, Edmonton (CA); Robert Hancock, Vancouver (CA); Scott Halperin, Halifax (CA); Jennifer Kovacs-Nolan, Guelph (CA); George Mutwiri, Saskatoon (CA); Song Lee, Halifax (CA); Mi-Na Kweon, Seoul (KR); Jason Kindrachuk, Vancouver (CA); Melissa Elliott, Vancouver (CA)

(73) Assignees: University of Saskatchewan, Saskatoon (CA); Dalhousie University, Nova Scotia (CA); International Vaccines Institute, Seoul (KR); University of British Columbia, Vancouver (CA)

( * ) Notice: Subject to any disclaimer, the term of this patent is extended or adjusted under 35 U.S.C. 154(b) by 716 days.

This patent is subject to a terminal disclaimer.

(21) Appl. No.: 12/587,955

(22) Filed: Oct. 15, 2009

(65) Prior Publication Data

US 2010/0239611 A1  Sep. 23, 2010

Related U.S. Application Data

(60) Provisional application No. 61/196,226, filed on Oct. 16, 2008.

(51) Int. Cl.
| *A61K 49/00* | (2006.01) |
| *A61K 47/00* | (2006.01) |
| *A61K 38/04* | (2006.01) |
| *A61K 39/39* | (2006.01) |
| *A61K 39/02* | (2006.01) |
| *A61K 39/155* | (2006.01) |
| *C07K 7/08* | (2006.01) |
| *A61K 45/06* | (2006.01) |
| *A61K 47/30* | (2006.01) |
| *A61K 39/00* | (2006.01) |

(52) U.S. Cl.
CPC .............. *A61K 39/39* (2013.01); *A61K 39/099* (2013.01); *A61K 39/155* (2013.01); *A61K 2039/55516* (2013.01); *A61K 2039/55561* (2013.01); *A61K 2039/6093* (2013.01); *C07K 7/08* (2013.01); *A61K 45/06* (2013.01); *A61K 47/30* (2013.01); *C12N 2760/18534* (2013.01)

(58) Field of Classification Search
None
See application file for complete search history.

(56) References Cited

U.S. PATENT DOCUMENTS

| 5,494,673 A | 2/1996 | Andrianov et al. |
| 5,500,161 A | 3/1996 | Andrianov et al. |
| 5,529,777 A | 6/1996 | Andrianov et al. |
| 5,562,909 A | 10/1996 | Allcock et al. |
| 5,760,271 A | 6/1998 | Andrianov et al. |
| 5,855,895 A | 1/1999 | Andrianov et al. |
| 5,891,444 A | 4/1999 | Jenkins et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 7,169,395 B1 | 1/2007 | Cates et al. |
| 2003/0139364 A1 | 7/2003 | Krieg et al. |
| 2005/0244505 A1* | 11/2005 | Higbee et al. ................. 424/489 |
| 2008/0237905 A1 | 10/2008 | Andrianov et al. |

FOREIGN PATENT DOCUMENTS

| WO | WO 95/02628 | 1/1995 |
| WO | 0115727 | 3/2001 |
| WO | 0122990 | 3/2001 |
| WO | 03015711 | 2/2003 |
| WO | WO 03/030934 | 4/2003 |
| WO | 2006050611 | 5/2006 |
| WO | 2008022444 | 2/2008 |

OTHER PUBLICATIONS

Andrianov et al., Synthesis, Properties, and Biological Activity of Poly[di(sodium carboxylatoethylphenoxy)phosphazene], 2006, Biomacromolecules, vol. 7, pp. 394-399.*
Medline Plus Medical Encyclopedia definition of Immune Response, accessed on Aug. 26, 2013 <<http://www.nlm.nih.gov/medlineplus/ency/article/000821.htm>>.*
Mutwiri et al. Innate Immunity and new adjuvants, 2007, Rev. sci. tech. Off. int. Epiz., vol. 26, No. 1, pp. 147-156.*
Asahi-Ozaki et al., Original article Intranasal administration of adjuvant-combined recombinant influenza virus HA vaccine protects mice from the lethal H5N1 virus infection, 2006, Microbes and Infection, vol. 8, pp. 2706-2714.*
U.S. Appl. No. 13/768,694, filed Feb. 15, 2013.*
Andrianov et al., Synthesis and Biologically Relevant Properties of Polyphosphazene Polyacids:, Biomacromolecules, 5:1999-2006 (2004).
Garlapati et al., "Immunization With PCEP Microparticles Containing Pertussis Toxoid, CPG ODN and a Synthetic Innate Defense Regulator Peptide Induces Protective Immunity Against Pertussis", Vaccine, 29:6540-6548 (2011).
Garlapati et al., "PCPP (Poly[Di(Carboxylatophenoxy)-Phosphazene]) Microparticles Co-Encapsulating Ovalbumin and CPG Oligo-Deoxynucleotides are Potent Enhancers of Antigen Specific TH1 Immune Responses in Mice", Vaccine, 28:8306-8314 (2010).

(Continued)

*Primary Examiner* — Benjamin P Blumel
(74) *Attorney, Agent, or Firm* — Roberta L. Robins; Robins Law Group

(57) ABSTRACT

Methods and compositions for enhancing an immune response to a selected antigen are described. The methods are useful for the treatment and prevention of microbial infections, such as infections caused by bacteria, viruses, fungi and parasites. The methods and compositions include host defense peptides, polyphosphazenes and immunostimulatory sequences to enhance the immune response to a coadministered antigen.

17 Claims, 28 Drawing Sheets

(56) References Cited

OTHER PUBLICATIONS

Gracia et al., "Antibody Responses in Adult and Neonatal BALB/C Mice to Immunization With Novel *Bordetella pertussis* Vaccine Formulations," Vaccine, 29:1595-1604 (2011).
Kindrachuk et al., "A Novel Vaccine Adjuvant Comprised of a Synthetic Innate Defence Regulator Peptide and CPG Oligonucleotide Links Innate and Adaptive Immunity", Vaccine, 27:4662-4671 (2009).
Kovacs-Nolan, et al., "Formulation of Bovine Respiratory Syncytial Virus Fusion Protein With CPG Oligodeoxynucleotide, Cationic Host Defence Peptide and Polyphosphazene Enhances Humoral and Cellular Responses and Induces a Protective Type 1 Immune Response in Mice", Journal of General Virology, 90(8):1892-1905 (2009).
Kovacs-Nolan et al., "CPG Oligonucleotide, Host Defense Peptide and Polyphosphazene Act Synergistically, Inducing Long-Lasting, Balanced Immune Responses in Cattle", Vaccine, 27(14):2048-2054 (2009).
Kovacs-Nolan et al., "The Novel Adjuvant Combination of CPG ODN, Indolicidin and Polyphosphazene Induces Potent Antibody- and Cell-Mediated Immune Responses in Mice", Vaccine, 27(14):2055-2064 (2009).
Liang et al., "Priming With DNA Encoding E2 and Boosting With E2 Protein Formulated With CPG Oligodeoxynucleotides Induces Strong Immune Responses and Protection From Bovine Viral Diarrhea Virus in Cattle", Journal of General Virology, 87(10):2971-2982 (2006).
Lopez et al., "Formulation With CPG ODN Enhances Antibody Responses to an Equine Influenza Virus Vaccine", Vet. Immunol. Immunopathol, 15:114(1-2):103-110 (2006).
Mapletoft et al., "Formulation With CPG Oligodeoxynucleotides Increases Cellular Immunity and Protection Induced by Vaccination of Calves With Formalin-Inactivated Bovine Respiratory Syncytial Virus", Virology, 353:316-323 (2006).
Mutwiri et al., "Approaches to Enhancing Immune Responses Stimulated by CPG Oligodeoxynucleotides", Adv Drug Deliv Rev., 61(3):226-232 (2009).
Wilson et at, "A Novel Triple Adjuvant Formulation Promotes Strong, TH1-Biased Immune Responses and Significant Antigen Retention At the Site of Injection", Vaccine, 28(52):8288-8299 (2010).
Biragyn, "Defensins-Non-Antibiotic Use for Vaccine Development," Current Protein and Peptide Science, 6:53-60 (2005).
Kindrachuk, et al., "A Novel Vaccine Adjuvant Comprised of a Synthetic Innate Defence Regulator Peptide and CPG Oligonucleotide Links Innate and Adaptive Immunity," Vaccine, 27:4662-4671 (2009).
Akira and Takeda, "Toll-like Receptor Signalling;" *Nat Rev Immunol* (2004) 4:499-511.
Alcon et al., "Induction of Protective Immunity in Pigs after Immunisation with CpG Oligodeoxynucleotides Formulated in a Lipid-based Delivery System (Biphasic™)," *Vaccine* (2003) 21:1811-1814.
Alexopoulou et al., "Recognition of Double-stranded RNA and Activation of NF-κB by Toll-like Receptor 3," *Nature* (2001) 413:732-738.
An et al., "LL-37 Enhances Adaptive Antitumor Immune Response in a Murine Model when Genetically Fused with M-CSFR$_{J6-1}$ DNA Vaccine," *Leuk Res* (2005) 29:535-543.
Andrianov et al., "Synthesis and Biologically Relevant Properties of Polyphosphazene Polyacids," *Biomacromolecules* (2005) 5:1999-2006.
Bowdish et al., "Immunomodulatory Activities of Small Host Defense Peptides," *Antimicrob Agents Chemother* (2005) 49:1727-1732.
Brogden et al., "Antimicrobial Peptides in Animals and Their Role in Host Defences," *Int J Antimicrob Agents* (2003) 22:465-478.
Brown et al., "Cationic Host Defense (Antimicrobial) Peptides," *Curr Opin Immunol* (2006) 18:24-30.
Cooper et al., "CPG 7909 Adjuvant Improves Hepatitis B Virus Vaccine Seroprotection in Antiretroviral-treated HIV-infected Adults," *AIDS* (2005) 19:1473-1479.
Davis et al., "CpG DNA is a Potent Enhancer of Specific Immunity in Mice Immunized with Recombinant Hepatitis B Surface Antigen," *J Immunol* (1998) 160:870-876.
Falla et al., "Mode of Action of the Antimicrobial Peptide Indolicidin," *J of Biol Chem* (1996) 271 (32):19298-19303.
Hancock, *Lancet Infect Dis* (2001) 1:156-164.
Ioannou et al., "CpG-containing Oligodeoxynucleotides, in Combination with Conventional Adjuvants, Enhance the Magnitude and Change the Bias of the Immune Responses to a Herpesvirus Glycoprotein," Vaccine (2002) 21:127-137.
Ioannou et al., "The Immunogenicity and Protective Efficacy of Bovine Herpesvirus 1 Glycoprotein D plus Emulsigen are Increased by Formulation with CpG Oligodeoxynucleotides," *J Virol* (2002) 76:9002-9010.
Kindrachuk et al., "Nucleic Acids Exert a Sequence-independent Cooperative Effect on Sequence-dependent Activation of Toll-like Receptor 9,"*J Biol Chem* (2007) 282:13944-13953.
Klinman et al. "CpG Motifs as Immune Adjuvants," *Vaccine* (1999) 17:19-25.
Klinman et al. "CpG Motifs Present in Bacterial DNA Rapidly Induce Lymphocytes to Secrete Interleukin 6, Interleukin 12, and Interferon γ," *Proc Natl Acad Sci USA* (1996) 93:2879-2883.
Krieg et al., "Therapeutic Potential of Toll-like Receptor 9 Activation," *Nat Rev Drug Discov* (2006) 5:471-484.
Krieg et al., "CpG Motifs in Bacterial DNA Trigger Direct B-cell Activation," *Nature* (1995) 374:546-549.
Kurosaka et al., "Mouse Cathelin-related Antimicrobial Peptide Chemoattracts Leukocytes Using Formyl Peptide Receptor-like 1/Mouse Formyl Peptide Receptor-like 2 as the Receptor and Acts as an Immune Adjuvant," *J Immunol* (2005) 174:6257-6265.
Lande et al., "Plasmacytoid Dendritic Cells Sense Self-DNA Coupled with Antimicrobial Peptide," *Nature* (2007) 449:564-569.
Lillard et al., "Mechanisms for Induction of Acquired Host Immunity by Neutrophil Peptide Defensins," *Proc Nati Acad Sci USA* (1999) 96:651-656.
Mapletoft et al., Intranasal Immunization of Mice with a Formalin-inactivated Bovine Respiratory Syncytial Virus Vaccine Co-formulated with CpG Oligodeoxynucleotides and Polyphosphazenes Results in Enhanced Protection, *J of Gen Virol* (2008) 89:250-260.
McNeal et al., "Effects of Different Adjuvants on Rotavirus Antibody Responses and Protection in Mice Following Intramuscular Immunization with Inactivated Rotavirus," *Vaccine* (1999) 17:1573-1580.
Mutwiri et al., Co-administration of Polyphosphazenes with CpG Oligodeoxynucletides Strongly Enhances Immune Responses in Mice Immunized with Hepatitis B Virus Surface Antigen, *Vaccine* (2008) 26:2680-2688.
Mutwiri et al., Poly[di(sodium carboxylatoethylphenoxy)phosphazene] (PCEP) is a Potent Enhancer of Mixed Th1/Th2 Immune Responses in Mice Immunized with Influenza Virus Antigens, *Vaccine* (2007) 25:1204-1213.
Payne et al., "Poly[di(carboxylatorphenoxy)phosphazene] (PCPP) is a Potent Immunoadjuvant for an Influenza Vaccine," *Vaccine* (1998) 16:92-98.
Andrianov and Payne, "Protein Release from Polyphosphazene Matrices," *Adv Drug Deliv Rev* (1998) 31:185-196.
Selsted et al., "Indolicidin, a Novel Bactericidal Tridecapeptide Amide from Neutrophils," *J Biol Chem* (1992) 267:4292-4295.
Tani et al., "Defensins Act as Potent Adjuvants that Promote Cellular and Humoral Immune Responses in Mice to a Lymphoma Idiotype and Carrier Antigens," *Int Immunol* (2000) 12:691-700.
Wu et al., "Evaluation of Cholera Vaccines Formulated with Toxin-coregulated Pilin Peptide Plus Polymer Adjuvant in Mice," *Infect and Immun* (2001) 69:7695-7702.
Yang et al., "Participation of Mammalian Defensins and Cathelicidins in Antimicrobial Immunity: Receptors and Activities of Human Defensins and Cathelicidin (LL-37)," *J of Leukocyte Biol* (2001) 69:691-697.

* cited by examiner

Hexachlorocyclotriphosphazene
(phosphazene cyclic trimer)

Polydichlorophosphazene
(PDCP)

Polydichlorophosphazene
(PDCP)

Poly(p-di-n-propoxycarboxylato-
phenoxy)phosphazene

Fig. 12AFig. 12B

SEQUENCE LISTING

<160> NUMBER OF SEQ ID NOS: 27

<210> SEQ ID NO 1
<211> LENGTH: 13
<212> TYPE: PRT
<213> ORGANISM: Artificial Sequence
<220> FEATURE:
<223> OTHER INFORMATION: indolicidin

<400> SEQUENCE: 1

Ile Leu Pro Trp Lys Trp Pro Trp Trp Pro Trp Arg Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: JK1

<400> SEQUENCE: 2

Val Phe Leu Arg Arg Ile Arg Val Ile Val Ile Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: JK2

<400> SEQUENCE: 3

Val Phe Trp Arg Arg Ile Arg Val Trp Val Ile Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: JK3

<400> SEQUENCE: 4

Val Gln Leu Arg Ala Ile Arg Val Arg Val Ile Arg
1               5                   10

-continued

```
<210> SEQ ID NO 5
<211> LENGTH: 12
<212> TYPE: PRT
<213> ORGANISM: Artificial Sequence
<220> FEATURE:
<223> OTHER INFORMATION: JK4

<400> SEQUENCE: 5

Val Gln Leu Arg Arg Ile Arg Val Trp Val Ile Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: JK5

<400> SEQUENCE: 6

Val Gln Trp Arg Ala Ile Arg Val Arg Val Ile Arg
1               5                   10

<210> SEQ ID NO 7
<211> LENGTH: 12
<212> TYPE: PRT
<213> ORGANISM: Artificial Sequence
<220> FEATURE:
<223> OTHER INFORMATION: JK6

<400> SEQUENCE: 7

Val Gln Trp Arg Arg Ile Arg Val Trp Val Ile Arg
1               5                   10

<210> SEQ ID NO 8
<211> LENGTH: 20
<212> TYPE: DNA
<213> ORGANISM: Artificial Sequence
<220> FEATURE:
<223> OTHER INFORMATION: CpG 1826

<400> SEQUENCE: 8
tccatgacgt tcctgacgtt                                           20

<210> SEQ ID NO 9
<211> LENGTH: 22
<212> TYPE: DNA
<213> ORGANISM: Artificial Sequence
<220> FEATURE:
<223> OTHER INFORMATION: CpG 2007

<400> SEQUENCE: 9
tcgtcgttgt cgttttgtcg tt                                        22

<210> SEQ ID NO 10
<211> LENGTH: 24
<212> TYPE: DNA
<213> ORGANISM: Artificial Sequence
<220> FEATURE:
<223> OTHER INFORMATION: CpG 7909 or 10103

<400> SEQUENCE: 10
tcgtcgtttt gtcgttttgt cgtt                                      24

<210> SEQ ID NO 11
<211> LENGTH: 21
<212> TYPE: DNA
<213> ORGANISM: Artificial Sequence
```

```
<220> FEATURE:
<223> OTHER INFORMATION: CpG 8954

<400> SEQUENCE: 11 gggggacgacg tcgtgggggg g                                              21

<210> SEQ ID NO 12
<211> LENGTH: 22
<212> TYPE: DNA
<213> ORGANISM: Artificial Sequence
<220> FEATURE:
<223> OTHER INFORMATION: CpG 2395 or 10101

<400> SEQUENCE: 12
tcgtcgtttt cggcgcgcgc cg                                              22

<210> SEQ ID NO 13
<211> LENGTH: 32
<212> TYPE: DNA
<213> ORGANISM: Artificial Sequence
<220> FEATURE:
<223> OTHER INFORMATION: non-CpG ISS

<400> SEQUENCE: 13
aaaaaaggta cctaaatagt atgtttctga aa                                   32

<210> SEQ ID NO 14
<211> LENGTH: 27
<212> TYPE: PRT
<213> ORGANISM: Artificial Sequence
<220> FEATURE:
<223> OTHER INFORMATION: BMAP27

<400> SEQUENCE: 14

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 15
<211> LENGTH: 28
<212> TYPE: PRT
<213> ORGANISM: Artificial Sequence
<220> FEATURE:
<223> OTHER INFORMATION: BMAP28

<400> SEQUENCE: 15

Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile Gly
            20                  25

<210> SEQ ID NO 16
<211> LENGTH: 12
<212> TYPE: PRT
<213> ORGANISM: Artificial Sequence
<220> FEATURE:
<223> OTHER INFORMATION: Bactenicin 2a (Bac2a)

<400> SEQUENCE: 16

Arg Leu Ala Arg Ile Val Val Ile Arg Val Ala Arg
1               5                   10
```

```
<210> SEQ ID NO 17
<211> LENGTH: 37
<212> TYPE: PRT
<213> ORGANISM: homo sapien

<400> SEQUENCE: 17

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 18
<211> LENGTH: 12
<212> TYPE: PRT
<213> ORGANISM: Artificial Sequence
<220> FEATURE:
<223> OTHER INFORMATION: HH2

<400> SEQUENCE: 18

Val Gln Leu Arg Ile Arg Val Ala Val Ile Arg Ala
1               5                   10

<210> SEQ ID NO 19
<211> LENGTH: 12
<212> TYPE: PRT
<213> ORGANISM: Artificial Sequence
<220> FEATURE:
<223> OTHER INFORMATION: 1002

<400> SEQUENCE: 19

Val Gln Arg Trp Leu Ile Val Trp Arg Ile Arg Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: 1018

<400> SEQUENCE: 20

Val Arg Leu Ile Val Ala Val Arg Ile Trp Arg Arg
1               5                   10

<210> SEQ ID NO 21
<211> LENGTH: 7
<212> TYPE: PRT
<213> ORGANISM: Artificial Sequence
<220> FEATURE:
<223> OTHER INFORMATION: HH18

<400> SEQUENCE: 21

Ile Trp Val Ile Trp Arg Arg
1               5

<210> SEQ ID NO 22
<211> LENGTH: 34
<212> TYPE: PRT
<213> ORGANISM: Artificial Sequence
<220> FEATURE:
<223> OTHER INFORMATION: Nisin Z
<220> FEATURE:
<221> NAME/KEY: misc_feature
<222> LOCATION: (2)..(2)
<223> OTHER INFORMATION: Xaa = Dehydrobutyrine (Dhb)
```

```
<220> FEATURE:
<221> NAME/KEY: misc_feature
<222> LOCATION: (5)..(5)
<223> OTHER INFORMATION: Xaa = Dehydroalanine (Dha)
<220> FEATURE:
<221> NAME/KEY: misc_feature
<222> LOCATION: (8)..(8)
<223> OTHER INFORMATION: Xaa = 2-Aminobutyric acid (Abu)
<220> FEATURE:
<221> NAME/KEY: misc_feature
<222> LOCATION: (13)..(13)
<223> OTHER INFORMATION: Xaa = 2-Aminobutyric acid (Abu)
<220> FEATURE:
<221> NAME/KEY: misc_feature
<222> LOCATION: (23)..(23)
<223> OTHER INFORMATION: Xaa = 2-Aminobutyric acid (Abu)
<220> FEATURE:
<221> NAME/KEY: misc_feature
<222> LOCATION: (25)..(25)
<223> OTHER INFORMATION: Xaa = 2-Aminobutyric acid (Abu)
<220> FEATURE:
<221> NAME/KEY: misc_feature
<222> LOCATION: (33)..(33)
<223> OTHER INFORMATION: Xaa = Dehydroalanine (Dha)

<400> SEQUENCE: 22

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala Asn Ala Ser Ile Asn Val
            20                  25                  30

Xaa Leu

<210> SEQ ID NO 23
<211> LENGTH: 12
<212> TYPE: PRT
<213> ORGANISM: Artificial Sequence
<220> FEATURE:
<223> OTHER INFORMATION: conserved motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 23

Val Xaa Xaa Arg Xaa Ile Arg Val Xaa Val Ile Arg
1               5                   10

<210> SEQ ID NO 24
<211> LENGTH: 13
<212> TYPE: PRT
<213> ORGANISM: Artificial Sequence
<220> FEATURE:
<223> OTHER INFORMATION: HH111

<400> SEQUENCE: 24

Ile Leu Lys Trp Lys Trp Pro Trp Trp Pro Trp Arg Arg
1               5                   10

<210> SEQ ID NO 25
<211> LENGTH: 13
<212> TYPE: PRT
<213> ORGANISM: Artificial Sequence
```

-continued

```
<220> FEATURE:
<223> OTHER INFORMATION: HH113

<400> SEQUENCE: 25

Ile Leu Pro Trp Lys Lys Pro Trp Trp Pro Trp Arg Arg
1               5                   10

<210> SEQ ID NO 26
<211> LENGTH: 13
<212> TYPE: PRT
<213> ORGANISM: Artificial Sequence
<220> FEATURE:
<223> OTHER INFORMATION: HH970

<400> SEQUENCE: 26

Ile Leu Lys Trp Lys Trp Pro Trp Trp Lys Trp Arg Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: HH1010

<400> SEQUENCE: 27

Ile Leu Arg Trp Lys Trp Arg Trp Trp Arg Trp Arg Arg
1               5                   10
```

COMBINATION ADJUVANT FORMULATION

CROSS-REFERENCE TO RELATED APPLICATION

This application claims the benefit under 35 U.S.C. §119 (e)(1) of U.S. Provisional Application No. 61/196,226, filed Oct. 16, 2008, which application is incorporated herein by reference in its entirety.

TECHNICAL FIELD

The present invention pertains generally to compositions for enhancing immune responses. In particular, the invention relates to combination adjuvant compositions including a host defense peptide, an immunostimulatory sequence and a polyanionic polymer, for use as vaccine adjuvants.

BACKGROUND

Killed or subunit vaccines are often poorly immunogenic, and can result in weak and transient T-cell responses, thus requiring adjuvants to boost the immune response. However, many currently available vaccines include adjuvants that are suboptimal with respect to the quality and magnitude of immune responses they induce. For example, alum, the only approved adjuvant for use in humans in the United States, induces good Th2 type immune responses but is not a potent adjuvant for Th1-type immune responses (HogenEsch et al., Vaccine (2002) 20 Suppl 3:S34-39). Thus, there is a need for additional effective and safer adjuvants.

Two broad categories of adjuvants exist—delivery systems and immunostimulatory adjuvants. Delivery systems include particulate formulations such as liposomes and microparticles. The mechanism of action of these systems are not fully understood but are thought to involve increased uptake by antigen presenting cells (APC) and/or formation of a depot at the site of injection. Immunostimulatory adjuvants stimulate innate immunity resulting in the secretion of cytokines and upregulation of costimulatory molecules. These events are now known to play an instructional role in the development of adaptive immune responses.

The most studied immunostimulatory adjuvants are microbial components, which are potent immune modulating molecules. Bacterial DNA, as well as synthetic CpG oligonucleotides bind to the cellular receptor Toll-Like Receptor 9 (TLR9) and stimulate a cascade of cell signaling events. CpG oligonucleotides are DNA sequences containing an unmethylated CpG dinucleotide, flanked by two 5' purines and two 3' pyrimidines. CpG oligonucleotides have been found to stimulate innate immune responses and trigger the production of Th-1 type cytokines, including IFN-γ, IL-6, IL-12, and TNF-α, via interaction of the CpG motif with TLR9 on dendritic cells, macrophages, and B lymphocytes (Klinman et al., Vaccine (1999) 17:19-25; Klinman et al., Proc Natl Acad Sci USA (1996) 93:2879-2883; Krieg, A. M., Nat Rev Drug Discov (2006) 5:471-484; and Krieg et al., Nature (1995) 374:546-549). Co-immunization of protein antigens with synthetic CpG ODNs has been found to increase the production of antigen-specific IgG and direct T-cell responses towards a Th1 phenotype (Ioannou et al., Vaccine (2002) 21:127-137). The adjuvant effects of CpG have been well demonstrated with a variety of viral, bacterial and protozoal antigens in a number of species including mice, cattle, sheep, pigs, and humans (Cooper et al., Aids (2005) 19:1473-1479; Alcon et al., Vaccine (2003) 21:1811-1814; Davis et al., J. Immunol. (1998) 160:870-876; Ioannou et al., J. Virol. (2002) 76:9002-9010; Ioannou et al., Vaccine (2002) 21:127-137).

TLR9 may also bind and be activated by non-CpG DNA (Kindrachuk et al. J. Biol. Chem (2007) 282: 13944-53; Lande et al. Nature (2007) 449:564-9). This activity, coupled with the human cathelicidin LL-37, indicates that the specificity of this receptor may be broadened to microbial or host DNA molecules that are able to localize to the endosome (Lande et al. Nature (2007) 449:564-9).

Viral components such as double stranded (ds) RNA have also been demonstrated to have potent immunostimulatory properties. dsRNA, as well as the synthetic dsRNA analog polyriboinosinic acid-polyribocytidylic acid (poly(I:C)), are recognized by TLR3 resulting in receptor activation (Alexopoulou et al. Nature (2001) 413: 732-8). The expression of TLR3 has been shown to confer responsiveness to purified dsRNA and poly(I:C) in cultured cells. Additionally, TLR3-deficient mice display impaired responses to these ligands (Akira and Takeda Nat Rev Immunol (2004) 4: 499-511). More recently, the host cell component mRNA has been demonstrated to be immunostimulatory due to recognition and activation of TLR3 following release from cells (Kariko et al. J. Biol. Chem. (2004) 26: 12542-12550). TLR3 activation results in the induction of NFkB and IRF3, ultimately leading to the production of antiviral molecules such as type I IFN (Alexopoulou et al., Nature (2001) 413: 732-8). TLR3 activation initiates cascades of phosphorylation and transcriptional activation events that result in the production of numerous inflammatory cytokines that are thought to contribute to innate immunity (Takeda and Akira J. Derm. Sci. (2004) 34:73-82).

Antimicrobial peptides (AMPs), also called "host defense peptides" or "cationic peptides" represent crucial elements of the innate immune system. AMPs can be classified into two broad groups of either cyclic or linear peptides which include a wide variety of molecules such as lysozymes, lactoferrin, secretory leukoprotease inhibitor, defensins and cathelicidins. Typically, AMPs are small molecules which often display a strong cationic charge. AMPs act as effector molecules of innate immunity by killing a broad spectrum of microbes including Gram-positive bacteria, Gram-negative bacteria, fungi, parasites and viruses.

Defensins and cathelicidins are the two major families of mammalian anti-microbial peptides. Defensins display a plethora of immunomodulatory activities, including the ability to stimulate chemotaxis of immature dendritic cells and T-cells, glucocorticoid production, macrophage phagocytosis, mast cell degranulation, complement activation and IL-8 production by epithelial cells (Yang et al., Cell. Mol. Life. Sci. (2001) 58:978-989). Thus, defensins represent an important link between innate and acquired immunity and are potent immune modulators and adjuvants for vaccines. For example, low concentrations of a human α-defensin (10-100 ng, administered with KLH absorbed to alum) lead to strong augmentation of IgG1, IgG2a and IgG2b, indicative of stimulation of both Th1 and Th2 responses (Tani et al., Int. Immunol. (2000) 12:691-700; Lillard et al., Proc. Natl. Acad. Sci. USA (1999) 96:651-656). In contrast, α- and β-defensins, co-delivered intranasally, have been reported to stimulate primarily a Th-2 response (IgG1 and IgG2b, but not IgG2a or IgM) to ovalbumin (Brogden et al., Int. J. Antimicrob. Agents (2003) 22:465-478). Intradermal immunization of mice with a fusion construct encoding the HIV glycoprotein 120 and β-defensin 2 resulted in strong humoral and cell-mediated mucosal immune responses against HIV and antitumor immune responses were greatly enhanced by the presence of defensins.

Likewise, cathelicidins, another class of endogenous mammalian host defense peptides, have been found to exert a number of immune-modulating functions. Besides their well-documented antimicrobial activity, cathelicidins act as chemotactic factors, induce cytokine and chemokine expression, alter gene expression in host cells, and modulate dendritic cell function (Bowdish et al., *Antimicrob. Agents Chemother.* (2005) 49:1727-1732; Brown et al., *Curr. Opin. Immunol.* (2006) 18:24-30; Hancock, R. E., *Lancet Infect. Dis.* (2001) 1:156-164). Recent evidence has also shown that the human cathelicidin LL-37 (An et al., *Leuk. Res.* (2005) 29:535-543) and mouse cathelin-related antimicrobial peptide (CRAMP) (Kurosaka et al., *J. Immunol.* (2005) 174: 6257-6265) were able to enhance adaptive immune responses.

Indolicidin, one of the smallest known host defense peptides, is a linear 13-amino acid peptide found in the cytoplasmic granules of bovine neutrophils (Selsted et al., *J. Biol. Chem.* (1992) 267:4292-4295). In vitro it was found to inhibit LPS-induced TNF-α secretion by human macrophage-like cells, and induce production of the chemokine IL-8 in human bronchial epithelial cells (Bowdish et al., *Antimicrob. Agents Chemother.* (2005) 49:1727-1732), however its activity as an adjuvant in vivo has yet to be established.

Polyphosphazenes are high-molecular weight, water-soluble polymers, containing a backbone of alternating phosphorous and nitrogen atoms (Payne et al., *Vaccine* (1998) 16:92-98). One of the most investigated polyphosphazene polyelectrolytes, poly[di(sodium carboxylatophenoxy)phosphazene] (PCPP) has been found to exert adjuvant activity when incorporated into a number of vaccine formulations, including influenza (Payne et al., *Vaccine* (1998) 16:92-98), human rotavirus (McNeal et al., *Vaccine* (1999) 17:1573-1580), and cholera vaccines (Wu et al., *Infect. Immun.* (2001) 69:7695-7702). Similarly, poly(di-4-oxyphenylproprionate) phosphazene (PCEP) has been shown to enhance antigen-specific immune responses to influenza antigens (Mutwiri et al., *Vaccine* (2007) 25:1204-1213). Polyphosphazene adjuvant activity does not appear to be due to the formation of an injection-site depot, but rather may be linked to the ability of the polymer to form water-soluble, non-covalent complexes with antigens, stabilizing them and allowing efficient presentation to immune cells (Andrianov et al., *Biomacromolecules* (2005) 5:1999-2006; Payne et al., *Adv. Drug Deliv. Rev.* (1998) 31:185-196).

Co-administration of PCPP with a CpG oligonucleotide has been shown to enhance immune responses in mice immunized with hepatitis B surface antigen (Mutwiri et al., *Vaccine* (2008) 26:2680-2688). Additionally, intranasal immunization using a formalin-inactivated bovine respiratory syncytial virus (BRSV) vaccine co-formulated with a CpG oligonucleotide and PCPP resulted in enhanced protection against BRSV challenge (Mapletoft et al., *J. Gen. Virol.* (2008) 89:250-260).

Despite the various advances in adjuvant technology, there remains a need for safe and effective methods to prevent infectious diseases. Thus, the wide-spread availability of new adjuvants would be highly desirable and could save a considerable number of lives.

SUMMARY OF THE INVENTION

The present invention is based in part, on the surprising discovery that the use of a delivery system including a host defense peptide, in combination with a polyanionic polymer such as a polyphosphazene, and a nucleic acid sequence possessing immunostimulatory properties (ISS), such as an oligodeoxynucleotide molecule with or without a CpG motif (a cytosine followed by guanosine and linked by a phosphate bond) or the synthetic dsRNA analog poly(I:C), provides for significantly higher antibody titers to a coadministered antigen, than those observed without such delivery systems. The use of such combinations provides a safe and effective approach for enhancing the immunogenicity of a variety of vaccine antigens for use in both prophylactic and therapeutic compositions.

Accordingly, in one embodiment, the invention is directed to an adjuvant composition comprising a host defense peptide, an immunostimulatory sequence and a polyanionic polymer, wherein the adjuvant composition is capable of enhancing an immune response to a selected antigen. In certain embodiments, the adjuvant composition further comprises the antigen. In additional embodiments, the antigen, whether included or separate from the adjuvant composition, is from a virus, bacteria, parasite or fungus, for example, from a respiratory syncitial virus (RSV), such as from BRSV or from *Bordetella*, such as from *B. pertussis*.

In additional embodiments, the host defense peptide is a defensin or a cathelicidin. In further embodiments, the host defense peptide is one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:14, SEQ ID NO:15: SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26 or SEQ ID NO:27.

In additional embodiments, the polyanionic polymer is poly[di(sodium carboxylatophenoxy)phosphazene] (PCPP), poly(di-4-oxyphenylproprionate)phosphazene (PCEP), or a PCPP polymer comprising 90% PCPP copolymer with 10% hydroxyl groups (90:10 PCPP).

In further embodiments, the immunostimulatory sequence is a CpG oligonucleotide, such as a fully phosphorothioated CpG oligonucleotide, for example, one or more of SEQ ID NO:8; SEQ ID NO:9; SEQ ID NO:10; SEQ ID NO:11 or SEQ ID NO:12.

In additional embodiments, the immunostimulatory sequence is SEQ ID NO:13.

In yet further embodiments, the immunostimulatory sequence is poly (I:C).

In additional embodiments, the invention is directed to a method of enhancing an immune response to a selected antigen. The method comprises administering to a subject any of the compositions described above. In certain embodiments, the host defense peptide, the immunostimulatory sequence, the polyanionic polymer and the selected antigen are present in the same composition. In alternative embodiments, at least one of the host defense peptide, the immunostimulatory sequence, the polyanionic polymer and the selected antigen is present in a different composition than the others.

In further embodiments, the invention is directed to an immunostimulatory peptide comprising an amino acid sequence selected from the group consisting of SEQ ID:2; SEQ ID NO:3; SEQ ID NO:4; SEQ ID NO:5; SEQ ID NO:6; and SEQ ID NO:7. In additional embodiments, the immunostimulatory peptide consists of an amino acid sequence selected from the group consisting of SEQ ID:2; SEQ ID NO:3; SEQ ID NO:4; SEQ ID NO:5; SEQ ID NO:6; and SEQ ID NO:7.

These and other embodiments of the subject invention will readily occur to those of skill in the art in view of the disclosure herein.

BRIEF DESCRIPTION OF THE FIGURES

FIG. 2A shows a ring-opening polymerization (ROP) reaction used to convert hexachlorocyclotriphosphazene [(N═PCl$_2$)$_3$] to polydichlorophosphazene (PDCP). FIG. 2B shows the first step of PCPP synthesis which converts PDCP to poly(p-di-n-propoxycarboxylatophenoxy)-phosphazene. FIG. 2C shows the conversion of poly(p-di-n-propoxycarboxylatophenoxy)phosphazene to 100% PCPP. FIG. 2D shows the conversion of 100% PCPP, sodium salt to poly(p-dicarboxylatophenoxy)phosphazene acid (PCPP-H).

FIG. 4A shows the conversion of PDCP to polydi(methyl-3-(4-oxyphenyl)-propionate)phosphazene. FIG. 4B shows the conversion scheme for polydi(methyl-3-(4-oxyphenyl)-propionate)phosphazene to PCEP.

FIG. 9A shows IgG1 titers; FIG. 9B shows IgG2a titers; FIG. 9C shows the numbers of IFN-γ-secreting splenocytes; and FIG. 9D shows numbers of IL-5-secreting splenocytes. In vitro restimulation results are expressed as the difference between the number of cytokine-secreting cells in ΔF-stimulated wells and medium-control wells per $10^6$ cells. Each data point represents an individual animal, and median values are indicated by horizontal lines. , $P<0.01$; *, $P<0.001$.

FIG. 10A shows the kinetics of the ΔF-specific serum IgG responses after one and two immunizations, and after challenge. Each data point represents the median value of each group. FIG. 10B shows ΔF-specific IgG1 (circles) and IgG2a (squares) after one and two immunizations. Each data point represents an individual animal, and median values are indicated by horizontal lines. FIG. 10C shows ΔF-specific IgG1 (circles) and IgG2a (squares) after challenge. Each data point represents an individual animal, and median values are indicated by horizontal lines. FIG. 10D shows virus-neutralizing antibody titers in sera after two immunizations (empty bars) and after challenge (shaded bars). Empty bars indicate values obtained from pooled sera; shaded bars indicate median values of the individual titers within each group. ***, $P<0.001$.

FIG. 11A shows the numbers of IFN-γ-secreting splenocytes in response to in vitro restimulation with ΔF in mice challenged with BRSV. FIG. 11B shows the numbers of IL-5-secreting splenocytes in response to in vitro restimulation with ΔF in mice challenged with BRSV. Results are expressed as the difference between the number of cytokine-secreting cells in ΔF-stimulated wells and medium-control wells per $10^6$ cells. Each data point represents an individual animal, and median values are indicated by horizontal lines. **, $P<0.01$.

FIGS. 12A-12C show cytokine/chemokine induction and cell populations in the lungs of mice immunized with ΔF alone or ΔF/CpG/indol/PP. FIG. 12A shows IL-5 concentrations in lung-homogenate supernatants. Each data point represents an individual animal, and median values are indicated by horizontal lines. FIG. 12B shows eotaxin concentrations in lung-homogenate supernatants. Each data point represents an individual animal, and median values are indicated by horizontal lines. FIG. 12C shows immune cells present in the lungs following immunization and challenge. Bars represent mean percentage of cell type per minimum 200 cells. **, $P<0.01$.

FIG. 14A shows serum total IgG titers. FIG. 14B shows numbers of IFN-γ-secreting cells. Each data point represents an individual animal, and median values are indicated by horizontal lines. *, $P<0.05$; , $P<0.01$; *, $P<0.001$.

FIG. 15A shows serum total anti-HEL IgG titers following primary immunization. FIG. 15B shows serum total anti-HEL IgG titers following secondary immunization. FIG. 15C shows numbers of IFN-γ-secreting cells. ELISA titers were expressed as the reciprocal of the highest dilution resulting in a reading of two standard deviations above the negative control. ELISPOT results were expressed as the difference between the number of cytokine-secreting cells in HEL-stimulated wells and medium-control wells per $10^6$ cells. Values represent geometric means. *, $P<0.05$; , $P<0.01$; *, $P<0.001$.

FIG. 16A shows levels of IFN-α. FIG. 16B shows levels of TNF-α. FIG. 16B shows levels of IFN-γ. Data shown represent the median values for 8 calves. *, $P<0.05$; , $P<0.01$; *, $P<0.001$.

DETAILED DESCRIPTION OF THE INVENTION

Figure 1:
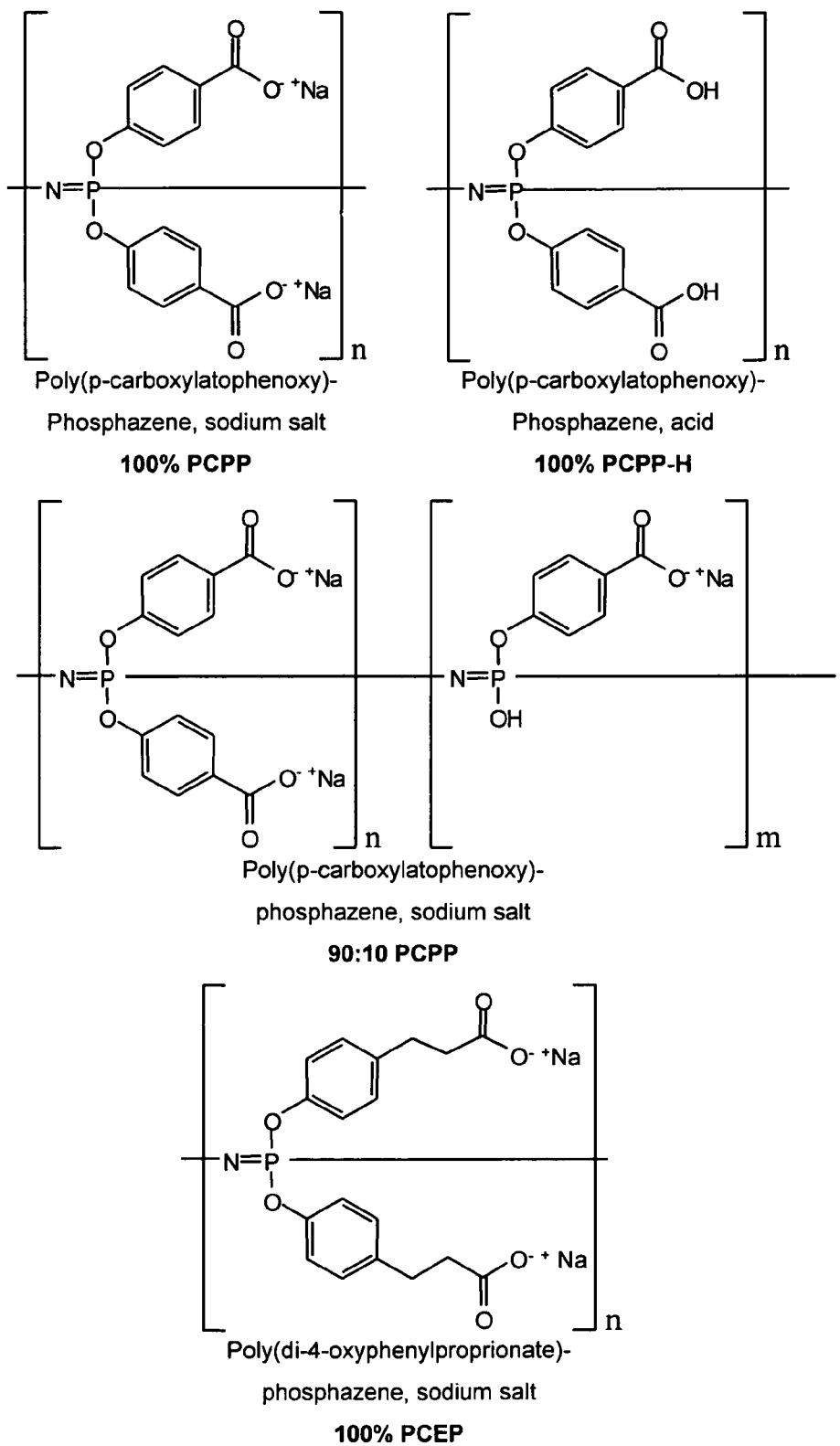
FIG. 1 shows representative polyphosphazine compounds for use in the present formulations.

The practice of the present invention will employ, unless otherwise indicated, conventional methods of microbiology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)
Dehydroalanine (Dha) Dehydrobutyrine (Dhb)

The following sequences are presented herein:

| SEQ ID NO | SEQUENCE | NAME |
|---|---|---|
| 1 | ILPWKWPWWPWRR | indolicidin |
| 2 | VFLRRIRVIVIR | JK1 |
| 3 | VFWRRIRVWVIR | JK2 |
| 4 | VQLRAIRVRVIR | JK3 |
| 5 | VQLRRIRVWVIR | JK4 |
| 6 | VQWRAIRVRVIR | JK5 |
| 7 | VQWRRIRVWVIR | JK6 |
| 8 | TCCATGACGTTCCTGACGTT | CpG 1826 |
| 9 | TCGTCGTTGTCGTTTGTCGTT | CpG 2007 |
| 10 | TCGTCGTTTTGTCGTTTTGTCGTT | CpG 7909 or 10103 |
| 11 | GGGGACGACGTCGTGGGGGGG | CpG 8954 |
| 12 | TCGTCGTTTTCGGCGCGCGCCG | CpG 2395 or 10101 |
| 13 | AAAAAAGGTACCTAAATAGTATGTTTCTGAAA | non-CpG ISS |
| 14 | GRFKRFRKKFKKLFKKLSPVIPLLHLG | BMAP27 |
| 15 | GGLRSLGRKILRAWKKYGPIIVPIIRIG | BMAP28 |
| 16 | RLARIVVIRVAR | Bactenicin 2a (Bac2a) |
| 17 | LLGDFFRKSKEKIGKEFKRIVQRIKDFLRNLVPRTES | human LL-37 |
| 18 | VQLRIRVAVIRA | HH2 |
| 19 | VQRWLIVWRIRK | 1002 |
| 20 | VRLIVAVRIWRR | 1018 |
| 21 | IWVIWRR | HH18 |
| 22 | Ile-Dhb-Ala-Ile-Dha-Leu-Ala-Abu-Pro-Gly-Ala-Lys-Abu-Gly-Ala-Leu-Met-Gly-Ala-Asn-Met-Lys-Abu-Ala-Abu-Ala-Asn-Ala-Ser-Ile-Asn-Val-Dha-Lys | Nisin Z |
| 23 | V**R*IRV*VIR, * = any amino acid | conserved motif |
| 24 | ILKWKWPWWPWRR | HH111 |
| 25 | ILPWKKPWWPWRR | HH113 |
| 26 | ILKWKWPWWKWRR | HH970 |
| 27 | ILRWKWRWWRWRR | HH1010 |

I. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a CpG oligonucleotide" includes a mixture of two or more CpGs, and the like.

By "host defense peptide" or "HDP" is meant any of the various host defense peptides that have the ability to enhance an immune response to a co-administered antigen. The DNA and corresponding amino acid sequences for various host defense peptides are known and described in detail below. Host defense peptides for use in the present methods include the full-length (i.e., a prepro sequence if present, the entire prepro molecule) or substantially full-length proteins, as well as biologically active fragments, fusions or mutants of the proteins. The term also includes postexpression modifications of the polypeptide, for example, glycosylation, acetylation, phosphorylation and the like. Furthermore, for purposes of the present invention, a "host defense peptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification. It is readily apparent that the host defense peptides may therefore comprise an entire leader sequence, the mature sequence, fragments, truncated and partial sequences, as well as analogs, muteins and precursor forms of the molecule. The term also intends deletions, additions and substitutions to the reference sequence, so long as the molecule retains the desired biological activity.

By "CpG oligonucleotide" or "CpG ODN" is meant an immunostimulatory nucleic acid containing at least one cytosine-guanine dinucleotide sequence (i.e., a 5' cytidine followed by 3' guanosine and linked by a phosphate bond) and which activates the immune system. An "unmethylated CpG oligonucleotide" is a nucleic acid molecule which contains an unmethylated cytosine-guanine dinucleotide sequence (i.e., an unmethylated 5' cytidine followed by 3' guanosine and linked by a phosphate bond) and which activates the immune system. A "methylated CpG oligonucleotide" is a nucleic acid which contains a methylated cytosine-guanine dinucleotide sequence (i.e., a methylated 5' cytidine followed by a 3' guanosine and linked by a phosphate bond) and which activates the immune system. CpG oligonucleotides are well known in the art and described in, e.g., U.S. Pat. Nos. 6,194,388; 6,207, 646; 6,214,806; 6,218,371; 6,239,116; and 6,339,068; PCT Publication No. WO 01/22990; PCT Publication No. WO 03/015711; US Publication No. 20030139364, which patents and publications are incorporated herein by reference in their entireties.

By "poly(I:C) oligonucleotide" or "poly(I:C)" is meant a synthetic viral-like double stranded immunostimulatory ribonucleic acid containing strands of polyriboinosinic acid and polyribocytidylic acid that are held together by hydrogen bonds between purine and pyrimidine bases in the chains. Poly I:C has been found to have a strong interferon-inducing effect in vitro and is therefore of significant interest in infectious disease research.

By "polyphosphazene" is meant a high-molecular weight, water-soluble polymer, containing a backbone of alternating phosphorous and nitrogen atoms and organic side groups attached at each phosphorus atom. See, e.g., Payne et al., *Vaccine* (1998) 16:92-98; Payne et al., *Adv. Drug. Deliv. Rev.* (1998) 31:185-196. A number of polyphosphazenes are known and described in more detail below.

By "antigen" or "immunogen" is meant a molecule, which contains one or more epitopes (defined below) that will stimulate a host's immune system to make a cellular antigen-specific immune response when the antigen is presented, or a humoral antibody response. The terms denote both subunit antigens, i.e., proteins which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein. Further, for purposes of the present invention, antigens can be derived from any of several known viruses, bacteria, parasites and fungi, as well as any of the various tumor antigens.

The term "derived from" is used to identify the original source of a molecule (e.g., bovine or human) but is not meant to limit the method by which the molecule is made which can be, for example, by chemical synthesis or recombinant means.

The terms "analog" and "mutein" refer to biologically active derivatives of the reference molecule, that retain desired activity as described herein. In general, the term "analog" refers to compounds having a native polypeptide sequence and structure with one or more amino acid additions, substitutions (generally conservative in nature) and/or deletions, relative to the native molecule, so long as the modifications do not destroy activity and which are "substantially homologous" to the reference molecule as defined below. The term "mutein" refers to peptides having one or more peptide mimics ("peptoids"), such as those described in International Publication No. WO 91/04282. Preferably, the analog or mutein has at least the same desired activity as the native molecule. Methods for making polypeptide analogs and muteins are known in the art and are described further below.

The terms also encompass purposeful mutations that are made to the reference molecule. Particularly preferred analogs include substitutions that are conservative in nature, i.e., those, substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the molecule of interest may include up to about 5-10 conservative or non-conservative amino acid substitutions, or even up to about 15-20 conservative or non-conservative amino acid substitutions, or any integer between 5-20, so long as the desired function of the molecule remains intact. One of skill in the art can readily determine regions of the molecule of interest that can tolerate change by reference to Hopp/Woods and Kyte-Doolittle plots, well known in the art.

By "fragment" is intended a molecule consisting of only a part of the intact full-length polypeptide sequence and structure. The fragment can include a C-terminal deletion, an N-terminal deletion, and/or an internal deletion of the native polypeptide. A fragment will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains the ability to elicit the desired biological response.

By "immunogenic fragment" is meant a fragment of a parent molecule which includes one or more epitopes and thus can modulate an immune response or can act as an adjuvant for a co-administered antigen and/or is capable of inducing an adaptive immune response. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

Immunogenic fragments, for purposes of the present invention, will usually be at least about 2 amino acids in length, more preferably about 5 amino acids in length, and most preferably at least about 10 to 15 amino acids in length. There is no critical upper limit to the length of the fragment, which could comprise nearly the full-length of the protein sequence, or even a fusion protein comprising two or more epitopes of the protein in question.

The term "epitope" refers to the site on an antigen or hapten to which specific B cells and T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

An "immunological response" to a composition is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display a protective immunological response to the microorganism in question, e.g., the host will be protected from subsequent infection by the pathogen and such protection will be demonstrated by either a reduction or lack of symptoms normally displayed by an infected host or a quicker recovery time.

The term "immunogenic" molecule refers to a molecule which elicits an immunological response as described above. An "immunogenic" protein or polypeptide, as used herein, includes the full-length sequence of the protein in question, including the precursor and mature forms, analogs thereof, or immunogenic fragments thereof.

An adjuvant composition comprising a host defense peptide, a polyphosphazene and an immunostimulatory sequence "enhances" or "increases" the immune response, or displays "enhanced" or "increased" immunogenicity vis-a-vis a selected antigen when it possesses a greater capacity to elicit an immune response than the immune response elicited by an equivalent amount of the antigen when delivered without the adjuvant composition. Such enhanced immunogenicity can be determined by administering the antigen and adjuvant composition, and antigen controls to animals and comparing antibody titers against the two using standard assays such as radioimmunoassay and ELISAs, well known in the art.

"Substantially purified" generally refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography, metal chelation chromatography, reversed phase chromatography, hydrophobic interaction chromatography, and sedimentation according to density.

By "isolated" is meant that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The terms "effective amount" or "pharmaceutically effective amount" of a composition, or a component of the composition, refers to a nontoxic but sufficient amount of the composition or component to provide the desired response, such as enhanced immunogenicity, and, optionally, a corresponding therapeutic effect. The exact amount required will vary from subject to subject, depending on the species, age, and general condition of the subject, the severity of the condition being treated, and the particular components of interest, mode of administration, and the like. An appropriate "effective" amount in any individual case may be determined by one of ordinary skill in the art using routine experimentation.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

The term "treatment" as used herein refers to either (1) the prevention of infection or reinfection (prophylaxis), or (2) the reduction or elimination of symptoms of the disease of interest (therapy).

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that compositions including an immunostimulatory sequence, such as CpG or non-CpG oligonucleotides, or poly(I:C), a polyanionic polymer such as a polyphosphazene and a host defense peptide enhance immune responses to a co-administered antigen and confer protection against infections in reliable animal challenge models.

Thus, the combination adjuvants of the present invention are useful for the prevention and treatment of infectious diseases caused by a variety of infectious microorganisms including diseases caused by bacteria, fungi, parasites and viruses in humans and other animals.

The adjuvant compositions of the invention can be introduced into a subject using any of various delivery techniques, described more fully below. The adjuvant compositions can be used with one or multiple antigens or immunogens including polypeptide, polynucleotide, polysaccharide, or lipid antigens or immunogens, as well as with inactivated or attenuated pathogens, to produce an immune response in the subject to which the compositions are delivered. The immune response can serve to protect against future infection, or can be used for the production of antibodies, both polyclonal and monoclonal, for use as diagnostics, immunopurification reagents and the like.

In order to further an understanding of the invention, a more detailed discussion is provided below regarding host defense peptides, immunostimulatory sequences, polyanionic polymers and immunogens for use in the subject compositions and methods.

Host Defense Peptides

As explained above, the methods and compositions of the present invention include host defense peptides. Over 400 of these anti-microbial proteins have been identified in plants, insects and animals. See, e.g., Boman, H. G., *Annu. Rev. Immunol.* (1995) 13:61-92; Boman, H. G., *Scand. J. Immunol.* (1998) 48:15-25; Broekaert et al., *Plant. Physiol.* (1995) 108:1353-1358; Steiner et al., *Nature* (1981) 292:246-248; Ganz et al., *Curr. Opin. Immunol.* (1994) 4:584-589; Lehrer et al., *Curr. Opin. Immunol.* (1999) 11:23-27. The two major families of mammalian host defense peptides are defensins and cathelcidins. See, e.g., Ganz et al., *Curr. Opin. Immunol.* (1994) 4:584-589; Lehrer et al., *Curr. Opin. Immunol.* (1999) 11:23-27; Ouellette et al., *FASEB J.* (1996) 10:1280-1289; Zanetti et al., *FEBS Lett.* (1995) 374:1-5.

Mammalian defensins are a family of cationic proteins that contain six highly conserved cysteine residues that form three pairs of intrachain-disulfide bonds. Mammalian defensins are classified into three subfamilies, α-, β-, and θ-defensins, based on the patterns of their intrachain-disulfide bridges, (Ganz et al., *Curr. Opin. Immunol.* (1994) 4:584-589; Lehrer et al., *Curr. Opin. Immunol.* (1999) 11:23-27; Tang et al., *Science* (1999) 286:498-502). The θ-defensin subfamily includes a cyclic molecule with its six cysteine residues linking C1 to C6, C2 to C5, and C3 to C4 (Tang et al., *Science* (1999) 286:498-502). The three disulfide bonds of α-defensins are paired C1 to C6, C2 to C4, and C3 to C5 (Ganz et al., *Curr. Opin. Immunol.* (1994) 4:584-589; Ouellette et al., *FASEB J.* (1996) 10:1280-1289; Zhang et al., *Biochemistry* (1992) 31:11348-11356). The disulfide bonds of β-defensins are C1 to C5, C2 to C4, and C3 to C6 (Ganz et al., *Curr. Opin. Immunol.* (1994) 4:584-589; Tang et al., *J. Biol. Chem.* (1993) 268:6649-6653).

More than 50 defensin family members have been identified in mammalian species. In humans, at least six α-defensins and three β-defensins have been identified (Ganz et al., *Curr. Opin. Immunol.* (1994) 4:584-589; Lehrer et al., *Curr. Opin. Immunol.* (1999) 11:23-27; Ouellette et al., *FASEB J.* (1996) 10:1280-1289; Ganz et al., *J. Clin. Invest.* (1985) 76:1427-1435; Wilde et al., *J. Biol. Chem.* (1989) 264:11200-11203; Mallow et al., *J. Biol. Chem.* (1996) 271: 4038-4045; Bensch et al., *FEBS Lett.* (1995) 368:331-335; Larrick et al., *Infect. Immun.* (1995) 63:1291-1297). Non-limiting examples of human defensins include human α-defensins 1, 2, 3, and 4, also termed human neutrophil peptides (HNP)1, 2, 3, and 4; human α-defensins 5 and 6 (HD5 and 6); and human β-defensins (HBD) 1, 2 and 3.

Cathelicidins are a family of anti-microbial proteins with a putative N-terminal signal peptide, a highly conserved cathelin (cathepsin L inhibitor)-like domain in the middle, and a less-conserved, C-terminal, anti-microbial domain (Lehrer et al., *Curr. Opin. Immunol.* (1999) 11:23-27; Zanetti et al., *FEBS Lett.* (1995) 374:1-5). About 20 cathelicidin members have been identified in mammals, with at least one cathelicidin from humans (Zanetti et al., *FEBS Lett.* (1995) 374:1-5; Larrick et al., *Infect. Immun.* (1995) 63:1291-1297; Cowland et al., *FEBS Lett.* (1995) 368:173-176; Agerberth et al., *Proc. Natl. Acad. Sci. USA* (1995) 92:195-199). Cleavage of human cathelicidin (hCAP18) liberates its C-terminal, anti-microbial domain, a peptide called LL-37, with two N-terminal leucine residues. LL-37 is 37 amino-acid residues in length (Zanetti et al., *FEBS Lett.* (1995) 374:1-5; Gudmundsson et al., *Eur. J. Biochem.* (1996) 238:325-332).

Another group of host defense peptides contains a high percentage of specific amino acids, such as the proline-/arginine-rich bovine peptides, Bac2a, BacS and Bac7 (Gennaro et al., *Infect. Immun.* (1989) 57:3142-3146) and the porcine peptide PR-39 (Agerberth et al., *Eur. J. Biochem.* (1991) 202:849-854); and indolicidin which is a 13-amino acid host defense peptide with the sequence ILPWKWPWWPWRR (SEQ ID NO:1).

Other representative host defense peptides are presented in Table 1 and in the examples, such as peptides 1002, 1018 and HH2, as well as peptides JK1 (VFLRRIRVIVIR; SEQ ID NO:2); JK2 (VFWRRIRVWVIR; SEQ ID NO:3); JK3 (VQLRAIRVRVIR; SEQ ID NO:4); JK4 (VQLRR-IRVWVIR; SEQ ID NO:5); JK5 (VQWRAIRVRVIR; SEQ ID NO:6); and JK6 (VQWRRIRVWVIR; SEQ ID NO:7).

Any of the above peptides, as well as fragments and analogs thereof, that display the appropriate biological activity, such as the ability to modulate an immune response, such as to enhance an immune response to a co-delivered antigen, will find use in the present methods.

The host defense peptides for use herein can include a prepro sequence, a pro-protein without the pre sequence, or the mature protein without the prepro sequence. If a signal sequence is present the molecules can include, for example, the native signal sequence, along with a pro-sequence or the mature sequence. Alternatively, a host defense peptide for use herein can include a pro sequence or mature sequence with a heterologous signal sequence. Alternatively, host defense peptide for use herein can include only the sequence of the mature protein, so long as the molecule retains biological activity. Moreover, host defense peptides for use herein can be biologically active molecules that display substantial homology to the parent molecule, as defined above.

Thus, host defense peptides for use with the present invention can include, for example, the entire parent molecule, or biologically active fragments thereof, such as fragments including contiguous amino acid sequences comprising at least about 5-10 up to about 50 to the full-length of the molecule in question, or any integer there between. The molecule will typically include one or more epitopes. Such epitopes are readily identifiable using techniques well known in the art, such as using standard antigenicity and hydropathy plots, for example those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots. This program can be used with the following parameters: averaging results over a window of 7; determining surface probability according to Emini; chain flexibility according to Karplus-Schulz; antigenicity index according to Jameson-Wolf; secondary structure according to Garnier-Osguthorpe-Robson; secondary structure according to Chou-Fasman; and identifying predicted glycosylation sites. One of skill in the art can readily use the information obtained in combination with teachings of the present specification to identify antigenic regions which should be included in the molecules for use with the present invention.

Enhanced adjuvant activity displayed by a host defense peptide can be elucidated by determining whether the composition of interest when co-delivered with the immunogen of interest, possesses a greater capacity to elicit an immune response than the immune response elicited by an equivalent amount of the composition delivered without the co-administered host defense peptide. Such enhanced immunogenicity can be determined by administering the composition of interest with and without co-administration of the host defense peptide, and comparing antibody titers or cellular immune response produced using standard assays such as radioimmunoassay, ELISAs, lymphoproliferation assays, and the like, well known in the art.

The host defense peptides for use with the present invention can be obtained using standard techniques. For example, since the host defense peptides are typically small, they can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The host defense peptides of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Alternatively, the host defense peptides can be produced by recombinant techniques. See, e.g., Zhang et al., *FEBS Lett.* (1998) 424:37-40; Zhang et al., *J. Biol. Chem.* (1999) 274: 24031-24037; Shi et al., *Infect. Immun.* (1999) 67:3121-3127. The host defense peptides can be produced recombinantly, e.g., by obtaining a DNA molecule from a cDNA library or vector including the same, or from host tissue using phenol extraction. Alternatively, DNA encoding the desired host defense peptide can be synthesized, along with an ATG initiation codon. The nucleotide sequence can be designed with the appropriate codons for the particular amino acid sequence desired. In general, one selects preferred codons for the intended host in which the sequence is expressed. The complete sequence is generally assembled from overlapping oligonucleotides prepared by standard methods and assembled into a complete coding sequence. See, e.g., Edge *Nature* (1981) 292:756; Nambair et al. *Science* (1984) 223: 1299; Jay et al. *J. Biol. Chem.* (1984) 259:6311. Automated synthetic techniques such as phosphoramide solid-phase synthesis, can be used to generate the nucleotide sequence. See, e.g., Beaucage, S. L. et al. *Tet. Lett.* (1981) 22:1859-1862; Matteucci, M. D. et al. *J. Am. Chem. Soc.* (1981) 103:3185-3191. Next the DNA is cloned into an appropriate vector, either procaryotic or eucaryotic, using conventional methods. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements. The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397. If present, the signal sequence can be the native leader found in association with the peptide of interest.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the peptides of interest. Mutants or analogs of host defense peptides for use in the subject compositions may be prepared by the deletion of a portion of the sequence encoding the molecule of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci. USA* 79:6409.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The host defense peptides, whether produced recombinantly or synthetically, are formulated into compositions and used in methods as detailed herein. Typical amounts of host defense peptides to be administered in the adjuvant compositions are from about 0.01 to about 8000 µg/kg, typically from about 0.05 to about 500 µg/kg, such as from 1 to 100 µg/kg, or 5 to 50 µg/kg, or any integer between these values.

Immunostimulatory Sequences

Bacterial DNA is known to stimulate mammalian immune responses. See, e.g., Krieg et al., *Nature* (1995) 374:546-549. This immunostimulatory ability has been attributed to the high frequency of immunostimulatory nucleic acid molecules (ISSs), such as unmethylated CpG dinucleotides present in bacterial DNA. Oligonucleotides containing unmethylated CpG motifs have been shown to induce activation of B cells, NK cells and antigen-presenting cells (APCs), such as monocytes and macrophages. See, e.g., U.S. Pat. No. 6,207,646, incorporated herein by reference in its entirety.

The present invention makes use of adjuvants that include components derived from ISSs. The ISS includes an oligonucleotide which can be part of a larger nucleotide construct such as plasmid or bacterial DNA. The oligonucleotide can be linearly or circularly configured, or can contain both linear and circular segments. The oligonucleotide may include modifications such as, but are not limited to, modifications of the 3'OH or 5'OH group, modifications of the nucleotide base, modifications of the sugar component, and modifications of the phosphate group. The ISS can comprise ribonucleotides (containing ribose as the only or principal sugar component), or deoxyribonucleotides (containing deoxyribose as the principal sugar component). Modified sugars or sugar analogs may also be incorporated in the oligonucleotide. Examples of sugar moieties that can be used include ribose, deoxyribose, pentose, deoxypentose, hexose, deoxyhexose, glucose, arabinose, xylose, lyxose, and a sugar analog cyclopentyl group. The sugar may be in pyranosyl or in a furanosyl form. A phosphorous derivative (or modified phosphate group) can be used and can be a monophosphate, diphosphate, triphosphate, alkylphosphate, alkanephosphate, phosphorothioate, phosphorodithioate, or the like. Nucleic acid bases that are incorporated in the oligonucleotide base of the ISS can be naturally occurring purine and pyrimidine bases, namely, uracil or thymine, cytosine, inosine, adenine and guanine, as well as naturally occurring and synthetic modifications of these bases. Moreover, a large number of non-natural nucleosides comprising various heterocyclic bases and various sugar moieties (and sugar analogs) are available, and known to those of skill in the art.

Structurally, the root oligonucleotide of the ISS is a CG-containing nucleotide sequence, which may be palindromic. The cytosine may be methylated or unmethylated. Examples of particular ISS molecules for use in the present invention include CpG, CpY and CpR molecules, and the like, known in the art.

Preferred molecules are those derived from the CpG family of molecules, CpG dinucleotides and synthetic oligonucleotides which comprise CpG motifs (see, e.g., Krieg et al. *Nature* (1995) 374:546 and Davis et al. *J. Immunol.* (1998) 160:870-876), such as any of the various immunostimulatory CpG oligonucleotides disclosed in U.S. Pat. Nos. 6,194,388; 6,207,646; 6,214,806; 6,218,371; 6,239,116; 6,339,068, US Publication No. 20030139364; PCT Publication No. WO 01/22990; PCT Publication No.; and WO 03/015711, all of which are incorporated herein by reference in their entireties. Such CpG oligonucleotides generally comprise at least 8 up to about 100 nucleotides, preferably 8 to 40 nucleotides, more preferably 15-35 nucleotides, preferably 15-25 nucleotides, and any number of nucleotides between these values. For example, oligonucleotides comprising the consensus CpG motif, represented by the formula 5'-$X_1$CG$X_2$-3', where $X_1$ and $X_2$ are nucleotides and C is unmethylated, will find use as immunostimulatory CpG molecules. Generally, $X_1$ is A, G or T, and $X_2$ is C or T. Other useful CpG molecules include those captured by the formula 5'-$X_1X_2$CG$X_3X_4$, where $X_1$ and $X_2$ are a sequence such as GpT, GpG, GpA, ApA, ApT, ApG, CpT, CpA, CpG, TpA, TpT or TpG, and $X_3$ and $X_4$ are TpT, CpT, ApT, ApG, CpG, TpC, ApC, CpC, TpA, ApA, GpT, CpA, or TpG, wherein "p" signifies a phosphate bond. Preferably, the oligonucleotides do not include a GCG sequence at or near the 5'- and/or 3' terminus. Additionally, the CpG is preferably flanked on its 5'-end with two purines (preferably a GpA dinucleotide) or with a purine and a pyrimidine (preferably, GpT), and flanked on its 3'-end with two pyrimidines, preferably a TpT or TpC dinucleotide. Thus, preferred molecules will comprise the sequence GACGTT, GACGTC, GTCGTT or GTCGCT, and these sequences will be flanked by several additional nucleotides, such as with 1-20 or more nucleotides, preferably 2 to 10 nucleotides and more preferably, 3 to 5 nucleotides, or any integer between these stated ranges. The nucleotides outside of the central core area appear to be extremely amendable to change.

Moreover, the ISS oligonucleotides for use herein may be double- or single-stranded. Double-stranded molecules are more stable in vivo while single-stranded molecules display enhanced immune activity. Additionally, the phosphate backbone may be modified, such as phosphorodithioate-modified, in order to enhance the immunostimulatory activity of the ISS molecule. As described in U.S. Pat. No. 6,207,646, CpG molecules with phosphorothioate backbones preferentially activate B-cells, while those having phosphodiester backbones preferentially activate monocytic (macrophages, dendritic cells and monocytes) and NK cells.

Different classes of CpG nucleic acids have been described. One class is potent for activating B cells but is relatively weak in inducing IFN-α and NK cell activation. This class has been termed the B class. The B class CpG nucleic acids are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068, incorporated herein by reference in their entireties. Another class is potent for inducing IFN-α and NK cell activation but is relatively weak at stimulating B cells; this class has been termed the A class. The A class CpG nucleic acids typically have stabilized poly-G sequences at 5' and 3' ends and a palindromic phosphodiester CpG dinucleotide-containing sequence of at least 6 nucleotides. See, for example, PCT Publication No. WO 01/22990, incorporated herein by reference in its entirety. Yet another class of CpG nucleic acids activates B cells and NK cells and induces IFN-α; this class has been termed the C-class. The C-class CpG nucleic acids typically are fully stabilized, include a B class-type sequence and a GC-rich palindrome or near-palindrome. This class has been described in PCT Publication No. WO 03/015711, the entire contents of which is incorporated herein by reference.

ISS molecules can readily be tested for their ability to stimulate an immune response using standard techniques, well known in the art. For example, the ability of the molecule to stimulate a humoral and/or cellular immune response is readily determined using the immunoassays described herein. Moreover, the adjuvant compositions and antigen can be administered with and without the ISS to determine whether an immune response is enhanced.

Exemplary, non-limiting examples of CpG oligonucleotides for use in the present compositions include 5'TCCATGACGTTCCTGACGTT3' (SEQ ID NO:8), termed CpG ODN 1826, a Class B CpG; 5'TCGTCGTTGTCGTTTTGTCGTT3' (SEQ ID NO:9), termed CpG ODN 2007, a Class B CpG; 5'TCGTCGTTTTGTCGTTTTGTCGTT3' (SEQ ID NO:10), also termed CPG 7909 or 10103, a Class B CpG; 5' GGGGACGACGTCGTGGGGGGG 3' (SEQ ID NO:11), termed CpG 8954, a Class A CpG; and 5'TCGTCGTTTTCGGCGCGCGCCG 3' (SEQ ID NO:12), also termed CpG 2395 or CpG 10101, a Class C CpG. All of the foregoing class B and C molecules are fully phosphorothioated. Non-CpG oligonucleotides for use in the present composition include the double stranded polyriboinosinic acid:polyribocytidylic acid, also termed poly(I:C); and a non-CpG oligonucleotide 5'AAAAAAGGTACCTAAATAGTATGTTTCTGAAA3' (SEQ ID NO:13).

As explained above, the ISS can be administered either prior to, concurrent with, or subsequent to, delivery of the antigen, the host defense peptide and the polyphosphazene. If administered prior to immunization with the antigen and/or the other adjuvant components, the ISS can be administered as early as 5-10 days prior to immunization, preferably 3-5 days prior to immunization and most preferably 1-3 or 2 days prior to immunization. If administered separately, the ISS can be delivered either to the same site of delivery as the antigen and/or adjuvant compositions or to a different delivery site. If simultaneous delivery is desired, the ISS can be included with the antigen and/or adjuvant compositions.

Generally about 0.01 to about 1000 µg/kg, typically from about 0.05 to about 500 µg/kg, such as from 1 to 100 µg/kg, or 5 to 50 µg/kg, or any amount within these ranges, of the ISS per dose, will find use with the present methods.

Polyanionic Polymers

A polyanionic polymer of the present invention is a polymer which, when present in the adjuvant composition is negatively-charged due to the presence of anionic constitutional repeating units (for example, units containing sulphate, Y sulphonate, carboxylate, phosphate and borate groups). A constitutional repeating unit or I monomer refers to the minimal structural unit of a polymer. The polyanionic polymer may be a polyanionic heteropolymer, comprising two or more different anionic constitutional repeating units, or may be a polyanionic homopolymer, consisting of a single anionic constitutional repeating unit. Not every monomer/repeat unit need be negatively charged.

The polyanionic polymer for use in the adjuvant compositions may be a chemical polymer and may comprise anionic constitutional repeating units obtained from a group such as but not limited to acrylic acid, methacrylic acid, maleic acid, fumaric acid, ethylsulphonic acid, vinyl sulphuric acid, vinyl sulphonic acid, styrenesulphonic acid, vinylphenyl sulphuric I acid, 2-methacryloyloxyethane sulphonic acid, 3-methacryloyloxy-2 hydroxypropanesulphonic acid, 3-methacryl amido-3-methylbutanoic acid, acrylamidomethylpropanesulfonic acid, vinylphosphoric acid, 4-vinylbenzoic acid, 3 vinyl oxypropane-1-sulphonic acid, N-vinylsuccinimidic acid, and salts of the foregoing.

Alternatively, the polyanionic polymer of the invention may be an oligo- or polysaccharide such as dextran.

Additionally, the polyanionic polymer can be an oligopeptide or a polypeptide. Such peptides may be D- or L-peptides, and may comprise anionic constitutional repeating units (or monomers) such as L-aspartic acid, D-aspartic acid, L-glutamic acid, D-glutamic acid, non-natural anionic amino acids (or salts or anionic chemical derivatives thereof).

In certain embodiments, the polyanionic polymer may be a polymethyl methacrylate polymer, as well as a polymer derived from poly(lactides) and poly(lactide-co-glycolides), known as PLG. See, e.g., Jeffery et al., *Pharm. Res.* (1993) 10:362-368; and McGee et al., *J. Microencap.* (1996).

In particularly preferred embodiments, the polyanionic polymer is a polyphosphazene. Polyphosphazenes are high-molecular weight, water-soluble polymers, containing a backbone of alternating phosphorous and nitrogen atoms, and organic side groups attached at each phosphorus atom. See, e.g., Payne et al., *Vaccine* (1998) 16:92-98; Payne et al., *Adv. Drug. Deliv. Rev.* (1998) 31:185-196. Polyphosphazenes can form non-covalent complexes when mixed with compounds of interest, such as antigens and other adjuvants, increasing their stability and allowing for multimeric presentation. More than 700 polyphosphazenes are known with varying chemical and physical properties. For a review, see, Mark et al. in "Inorganic Polymers, 2nd Edition," Oxford University Press, 2005. Typically, polyphosphazenes for use with the present adjuvant compositions will either take the form of a polymer in aqueous solution or a polymer microparticle, with or without encapsulated or adsorbed substances such as antigens or other adjuvants.

For example, the polyphosphazene component of the adjuvant compositions can be a soluble polyphosphazene, such as a polyphosphazene polyelectrolyte with ionized or ionizable pendant groups that contain, for example, carboxylic acid, sulfonic acid or hydroxyl moieties, and pendant groups that are susceptible to hydrolysis under conditions of use to impart biodegradable properties to the polymer. Such polyphosphazene polyelectrolytes are well known and described in, for example, U.S. Pat. Nos. 5,494,673; 5,562,909; 5,855,895; 6,015,563; and 6,261,573, incorporated herein by reference in their entireties.

Alternatively, polyphosphazene polymers in the form of cross-linked microparticles will also find use in the present adjuvant compositions. Such cross-linked polyphosphazene polymer microparticles are well known in the art and described in, e.g., U.S. Pat. Nos. 5,053,451; 5,149,543; 5,308,701; 5,494,682; 5,529,777; 5,807,757; 5,985,354; and 6,207,171, incorporated herein by reference in their entireties.

Particularly preferred polyphosphazene polymers for use in the present methods and compositions are shown in FIG. 1 and include poly[di(sodium carboxylatophenoxy)phosphazene] (PCPP) and poly(di-4-oxyphenylproprionate)phosphazene (PCEP), in various forms, such as the sodium salt, or acidic forms, as well as a polymer composed of varying percentages of PCPP or PCEP copolymer with hydroxyl groups, such as 90:10 PCPP/OH.

Methods for synthesizing these compounds are known and described in the patents referenced above, as well as in Andrianov et al., *Biomacromolecules* (2004) 5:1999; Andrianov et al., *Macromolecules* (2004) 37:414; Mutwiri et al., *Vaccine* (2007) 25:1204; and the examples herein (see FIGS. 2-4).

As with the adjuvant components described above, the polyphosphazene can be administered either prior to, concurrent with, or subsequent to, delivery of the antigen, and other components. If administered prior to immunization with the antigen and/or the other adjuvant components, the polyphosphazene can be administered as early as 5-10 days prior to immunization, preferably 3-5 days prior to immunization and most preferably 1-3 or 2 days prior to immunization. If administered separately, the polyphosphazene can be delivered either to the same site of delivery as the antigen and/or adjuvant compositions or to a different delivery site. If simultaneous delivery is desired, the polyphosphazene can be included with the antigen and/or adjuvant compositions.

Typical amounts of polyphosphazene to be administered in the adjuvant compositions are from about 0.01 to about 2500 µg/kg, typically from about 0.05 to about 500 µg/kg, such as from 0.5 to 100 µg/kg, or 1 to 50 µg/kg, or any integer between these values.

Immunogens

As explained above, the compositions of the invention are useful as adjuvants to be provided in combination with immunogens or vaccines, in order to enhance an immune response, such as a cell-mediated or humoral immune response, to the co-delivered antigen. Immunogens for use with the adjuvant compositions include, but are not limited to, immunogens of viral, bacterial, mycobacterial, fungal, or parasitic origin.

For example, the adjuvant compositions of the invention can be used in combination with immunogens to treat or prevent a wide variety of infections caused by bacteria, including gram-negative and gram-positive bacteria.

Non-limiting examples of bacterial pathogens from which immunogens can be derived include both gram negative and gram positive bacteria. Gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pylori*, *Borelia burgdorferi*, *Legionella pneumophilia*, *Mycobacteria* sp. (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (*anaerobic* sp.), *Streptococcus pneumoniae*, pathogenic *Campylobacter* spp., *Enterococcus* sp., *Haemophilus infuenzae*, *Bacillus antracis*, *Corynebacterium diphtheriae*, *Corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

For example, the adjuvant compositions of the present invention can be used with any of the various *Bordetella* species including *B. pertussis*, *B. parapertussis*, *B. bronhiseptica*, and the like; various *Neisserial* species, including *N. meningitidis*, *N. gonorrhoeae*, etc.; various Enterobacteriaceae such as but not limited to *Salmonella*, such as *S. typhimurium*, *S. enteritidis*, *Shigella*, such as *S. flexneri*, *Escherichia*, such as *E. coli* O157:H7, *Klebsiella*, *Enterobacter*, *Serratia*, *Proteus*, *Morganella*, *Providencia*, *Yersinia*, such as *Y. enterocolitica*, *Listeria*, such as *L. monocytogene*, *Staphylococcus*, such as *S. aureus*; various *Pseudomonas* species, such as *P. aeruginosa*; *Stretococcal* species, such as *S. suis*, *S. uberis*, *S. agalactiae*, *S. dysgalactiae*, *S. pneumoniae*, *S. pyogenes*, and the like; various *Actinobacillus* species, including but not limited to *A. Pleuropneumoniae*, *A. suis*, *A. pyogenes*, etc.

The adjuvant compostitions can be used in combination with immunogens to treat or prevent diseases caused by improper food handling, as well as diseases caused by food-borne pathogens, such as but not limited to *Salmonella enteritidis*, *Salmonella typhimurium*, *Escherichia coli* O157:H7, *Yersinia enterocolitica*, *Shigella flexneri*, *Listeria monocytogene*, and *Staphylococcus aureus*. Additionally, the adjuvant compositions are also useful in combination with immunogens against pathogens that cause nosocomial infections, such as but not limited to pathogens that produce extended spectrum β-lactamases (ESBL) and thus have the ability to inactivate β-lactam antibiotics. These enzymes are produced by various bacteria, including *Klebsiella pneumoniae*, *E. coli* and *Proteus mirabilis*. Additionally, the adjuvant compositions can be used in combination with immunogens to treat or prevent diseases caused by biocontamination of the skin by pathogenic microorganisms such as *Staphylococcus aureus*, *S. epidermitidis*, *Pseudomonas aeruginosa*, *Acinetobacter* spp., *Klebsiella pneumoniae*, *Enterobacter cloacae*, *E. coli*, *Proteus* spp. and fungi such as *Candida albicans*.

The adjuvant compositions can also be used in combination with immunogens to treat or prevent respiratory conditions such as caused by *Streptococcus pneumoniae, Haemophilus influenzae*, and *Pseudomonas aeruginosa*, as well as sexually transmitted diseases, including but not limited to *Chlamydia* infections, such as caused by *Chlamydia trachomatis* and gonococcal infections, such as caused by *Neisseria gonorrhoeae*.

Additionally, the adjuvant compositions can be used with immunogens to treat or prevent a number of viral diseases, such as but not limited to those diseases caused by members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; See, e.g. Virology, 3rd Edition (W. K. Joklik ed. 1988); *Fundamental Virology*, 2nd Edition (B. N. Fields and D. M. Knipe, eds. 1991), for a description of these and other viruses. Other particular examples of viruses include the herpesvirus family of viruses, for example bovine herpes virus (BHV) and human herpes simplex virus (HSV) types 1 and 2, such as BHV-1, BHV-2, HSV-1 and HSV-2, varicella zoster virus (VZV), Epstein-Barr virus (EBV), cytomegalovirus (CMV), HHV6 and HHV7; diseases caused by the various hepatitis viruses, such as HAV, HBV and HCV; diseases caused by papilloma viruses and rotaviruses, etc.

Non-limiting examples of viral pathogens that affect humans and/or nonhuman vertebrates from which immunogens can be derived, or which can be provided in attenuated or inactivated form include retroviruses, RNA viruses and DNA viruses. The group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus, avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses from which immunogens can be derived include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venèzuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, BVDV, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus (BRSV) and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus (BRSV) and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronaviridae, including the SARS virus, Infectious Bronchitis Virus (IBV), Mouse Hepatitis virus, Human enteric corona virus, and Feline infectious peritonitis (Feline coronavirus).

Illustrative DNA viruses from which immunogens can be derived include, but are not limited to: the family Poxyiridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex virus Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesvirises (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

Similarly, the adjuvant compositions of the invention will find use against a variety of parasites, such as but not limited to *Plasmodium*, such as *P. malariae, P. yoelii, P. falciparum, P. ovale,* and *P. vivax, Toxoplasma gondii, Schistosoma japonicum, Leishmania major, Trypanosoma cruzi,* and so forth.

Additionally, the adjuvant compositions find use to enhance an immune response against a number of fungal pathogens, such as but not limited to those fungi causing *Candidiasis, Cryptococcosis, Asperigillosis, Zygomycosis, Blastomycosis, Coccidioidomycosis, Histoplasmosis, Paracoccidiodomycosis, Sporotrichosis*. Particular non-limiting examples of infectious fungi from which immunogens can be derived include: *Cryptococcus neoformans, Histoplasma capsulatum, Coccidioides immitis, Blastomyces dermatitidis, Chlamydia trachomatis, Candida albicans.*

Other medically relevant microorganisms have been described extensively in the literature. See, e.g. C. G. A Thomas, Medical Microbiology, *Bailliere Tindall*, Great Britain 1983, the entire contents of which is hereby incorporated by reference.

In addition to the treatment of infectious human diseases, the methods of the invention are useful for treating infections of animals. For example, birds, cattle, horses and other farm animals are susceptible to infection. Diseases which affect these animals can produce severe economic losses. Thus, the compositions and methods of the invention can be used to protect against infection in livestock, such as cows, horses, pigs, sheep, and goats. For example, the compositions and methods can be used to protect against shipping fever, bovine viral diarrhea virus (BVDV), bovine respiratorysyncytial virus (BRSV) hog cholera virus (HOCV), sheep border disease virus (BDV), Equine herpesviruses (EHV), and visnamaedi. Cats, both domestic and wild, are also susceptible to infection with a variety of microorganisms. Thus, the invention is also useful for protecting pets against, for example, feline infectious peritonitis (FIP), feline leukemia virus (FeLV), feline sarcoma virus (FeSV), endogenous type C oncornavirus (RD-114), feline syncytia-forming virus (FeSFV), and feline T-lymphotropic lentivirus (also referred to as feline immunodeficiency).

As shown in the examples, the use of antigens from respiratory syncytial viruses, such as BRSV, in combination with the adjuvant compositions of the invention, provide immunity from subsequent challenge with BRSV. Useful antigens in this regard include RSV antigens, such as the fusion (F) protein, the attachment (G) protein, and/or the matrix (M) protein. These proteins are well known and can be obtained as described in U.S. Pat. No. 7,169,395, incorporated herein by reference in its entirety. Thus, RSV vaccines containing one, two or all of these proteins will find use herein.

It is readily apparent that adjuvants will find use for the delivery of a wide variety of immunogens to both human and nonhuman organisms to prevent or treat a wide variety of diseases.

These immunogens can be provided as attenuated, inactivated or subunit vaccine compositions. Additionally, the immunogens can be provided in nucleic acid constructs for DNA immunization. Techniques for preparing DNA immunogens are well known in the art and described in, e.g., U.S. Pat. Nos. 5,399,346, 5,580,859, 5,589,466, incorporated by reference herein in their entireties.

The adjuvant compositions of the invention are useful in combination with vaccines, in order to enhance an immune response, such as a cell-mediated or humoral immune response, to the co-delivered antigen. For example, the adjuvant compositions can be co-administered with commercially available animal and human vaccines, including but not limited to pertussis vaccines and combination vaccines, such as the various whole cell (wP) and acellular vaccines (aP). Non-limiting examples of such vaccines include the vaccines known as TRIPEDIA, TRIPACEL, QUADRACEL, TETRAVAL, TETRACT-Hib, PENTACT-Hib, PENTACEL, PENTAVAC, and HEXAVAC (Aventis, Bridgewater, N.J.); INFANRIX and PEDIARIX (GlaxoSmithKline, Research Triangle Park, N.C.); CERTIVA (North American Vaccine, Beltsville, Md.); BIOTHRAX; TICE BCG; MYCOBAX; HiBTITER; PEDVAXHIB; ACTHIB; COMVAX; HAVRIX; VAQTA; TWINRIX; RECOMBIVAX HB; ENGERIX-B; FLUMIST; FLUVIDRIN; FLUZONE; JE-VAX; ATTENUVAX; M-M-VAX; M-M-R II; MENUMONE-A/C/Y/W-135;

MUMPSVAX; PNEUMOVAX 23; PREVNAR; POLIO-VAX; IPOL; IMOVAX; RABAVERT; MERUVAX II; DRY-VAX; TYPHIM Vi; VIVOTIF; VARIVAX; YF-VAX.

The immunogens can be administered prior to, concurrently with, or subsequent to the various components of the adjuvant compositions. If administered concurrently, the immunogens can be administered in the same or in a different composition. If provided in a different composition, the immunogens can be administered at the same or different site of administration.

The immunogens for use with the present invention can be prepared using standard techniques, well known in the art. For example, the immunogens can be isolated directly from the organism of interest, or can be produced recombinantly or synthetically, using techniques described above.

Formulations and Administration

The above adjuvant components can be formulated into compositions, either alone or in combination with antigens, as described above, for delivery to subjects for enhancing an immune response to the co-administered antigen or combination of antigens. Each of the components, i.e., the ISS, the polyphosphazene and the host defense peptide can be formulated together in a single composition, or can be administered separately in an individual composition. Thus, for example, the host defense peptide can be combined in a single composition with the ISS and/or the polyphosphazene. Likewise, the polyphosphazene can be administered separately or combined with either or both of the host defense peptide and/or the ISS. The immunogen can be present in any of these combinations or may be administered separately. Methods of preparing such formulations are described in, e.g., *Remington's Pharmaceutical Sciences*, Mack Publishing Company, Easton, Pa., 18 Edition, 1990.

The compositions of the present invention can be prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Additional adjuvants which enhance the effectiveness of the composition may also be added to the formulation. Adjuvants may include for example, muramyl dipeptides, pyridine, aluminum hydroxide, dimethyldioctadecyl ammonium bromide (DDA), oils, oil-in-water emulsions, saponins, cytokines, and other substances known in the art.

The individual components of the compositions may also be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The various components of the compositions may be used in their native form or their functional group content may be modified by, for example, succinylation of lysine residues or reaction with Cys-thiolactone. A sulfhydryl group may also be incorporated by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides. Other suitable carriers include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as dendritic cells or lymphocytes, since presentation in this form mimics the natural mode of presentation in the subject, which gives rise to the immunized state. Methods of coupling peptides to proteins or cells are known to those of skill in the art.

Furthermore, the various components (or complexes thereof) may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable formulations will contain a "pharmaceutically effective amount" of the active ingredient, that is, an amount capable of achieving the desired response in a subject to which the composition is administered. In the therapy and prevention of pertussis, for example, a "pharmaceutically effective amount" would preferably be an amount which reduces or ameliorates the symptoms of the disease in question. The exact amount is readily determined by one skilled in the art using standard tests. The quantity to be administered depends on the animal to be treated, the capacity of the animal's immune system to synthesize antibodies, and the degree of protection desired. Effective dosages can be readily established by one of ordinary skill in the art through routine trials establishing dose response curves.

The composition can be administered parenterally, e.g., by intratracheal, intramuscular, subcutaneous, intraperitoneal, intravenous injection, or by delivery mucosally, i.e. intranasally, or by delivery directly to the lungs. The subject is administered at least one dose of the composition. Moreover, the animal may be administered as many doses as is required to bring about the desired biological effect.

Additional formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause major irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and HYTREL copolymers, swellable polymers such as hydrogels, resorbable polymers such as collagen and certain polyacids or polyesters such as those used to make resorbable sutures, polyphosphazenes, alginate, microparticles, gelatin nanospheres, chitosan nanoparticles, and the like. The compositions can also be delivered using implanted mini-pumps, well known in the art.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Production of Host Defense Peptides for Use in Combination Adjuvant Formulations Initially, three panels of HDPs were produced using standard methods of protein synthesis. The first panel included bovine cathelicidins BMAP27 (GRFKRFRKKFKKLFKKL-SPVIPLLHLG; SEQ ID NO:14), BMAP28 (GGL-RSLGRKILRAWKKYGPIIVPIIRIG; SEQ ID NO:15), Bactenicin 2a (Bac2a) (RLARIVVIRVAR, SEQ ID NO:16), Indolicidin (ILPWKWPWWPWRR (SEQ ID NO:1) and human LL-37 (LLGDFFRKSKEKIGKEFKRIVQRIKDFL-RNLVPRTES, SEQ ID NO:17). These peptides were used for the initial activity screening in murine, porcine and human PBMCs, using routine methods.

Two panels of 7-12 amino acid linear cationic peptides were produced. One panel of 20 peptides (the HH-class peptides) was based on the sequence of Bac2a, which is a linear variant of peptide bactenecin found in bovine neutrophils. These peptides have been described in PCT Publication No. WO 2006050611, the entire contents of which is incorporated herein by reference. These peptides were tested for induction of chemokines and cytokines in human PBMCs. Human PBMCs stimulated with 20 and 100 µg/ml of host defense peptides were assessed for various cytokines and chemokines at the 24 hour time-point by ELISA (eBiosciences). Production of three chemokines, MCP1, MCP3 and Gro-α were identified as the most robust response and were used in further screening. Peptides HH2 and HH18 (Table 1) were identified as the most active peptides. Activity of these peptides was further confirmed in human cord blood mononuclear cells, representing responses of the monocytic cells of a neonate. Another panel of 50 peptides was then designed based on the sequences of the most active peptides from the first panel using combinations of sequence scrambling, sequence substitutions and sequence deletions (see, PCT Publication No. WO2008022444, incorporated herein by reference in its entirety). Lead candidate peptides 1002 and 1018 were selected based on two criteria; First, the ability to induce chemokines in human PBMCs, and second, minimal cytotoxicity as assessed by LDH release in human PBMCs and haemolysis of human red blood cells. Furthermore the lantibiotic nisin (nisinA, nisinZ) was selected as a natural cationic peptide with immunomodulatory activity (see, U.S. provisional application 60/929,086). Peptides that demonstrated superior immunomodulatory activity and minimal cytotoxicity were assessed for protective abilities in vivo against *S. aureus*. Subsequently, selected host defense peptides were examined for protective activity in vivo. Briefly, BALB/c mice were administered peptides (8 mg/kg) by i.p. administration 4 h prior to infection. Mice were infected with $8.4 \times 10^7$ *S. aureus* in 5% mucin by i.p. administration. Bacterial counts in the peritoneal lavage were determined in 24 h after the initiation of infection.

Peptides HH2, 1002, 1018 and the lantibiotic nisin Z demonstrated the most desirable properties and all offered protection in animal challenges against *S. aureus* (Table 1; WO2006050611, WO2008022444, U.S. provisional application 60/929,086).

TABLE 1

Chemokine induction by synthetic peptides and the lantibiotic nisin Z in human PBMC.

| | | Chemokine Induction (pg/ml) | | | | | |
|---|---|---|---|---|---|---|---|
| | | MCP-1 (Peptide Concentration) | | MCP-3 (Peptide Concentration) | | Gro-α (Peptide Concentration) | |
| Name | Sequence | (20 µg/ml) | (100 µg/ml) | (20 µg/ml) | (100 µg/ml) | (20 µg/ml) | (100 µg/ml) |
| HH2 | VQLRIRVAVIRA (SEQ ID NO: 18) | 4882 | 10235 | 86 | 283 | 867 | 2693 |
| 1002 | VQRWLIVWRIRK (SEQ ID NO: 19) | 2472 | 5566 | 13 | 141 | 1032 | 2117 |
| 1018 | VRLIVAVRIWRR (SEQ ID NO: 20) | 8774 | 13041 | 156 | 604 | 826 | 2692 |
| HH18 | IWVIWRR (SEQ ID NO: 21) | 1111 | 9608 | 32 | 431 | 865 | 2964 |

TABLE 1-continued

Chemokine induction by synthetic peptides and the lantibiotic nisin Z in human PBMC.

| | | Chemokine Induction (pg/ml) | | | | | |
|---|---|---|---|---|---|---|---|
| | | MCP-1 (Peptide Concentration) | | MCP-3 (Peptide Concentration) | | Gro-α (Peptide Concentration) | |
| Name | Sequence | (20 µg/ml) | (100 µg/ml) | (20 µg/ml) | (100 µg/ml) | (20 µg/ml) | (100 µg/ml) |
| Nisin Z | Ile-Dhb-Ala-Ile-Dha-Leu-Ala-Abu-Pro-Gly-Ala-Lys-Abu-Gly-Ala-Leu-Met-Gly-Ala-Asn-Met-Lys-Abu-Ala-Abu-Ala-Asn-Ala-Ser-Ile-Asn-Val-Dha-Lys (SEQ ID NO: 22) | 434 | 7329 | nd | nd | 62 | 5811 | nd.: not determined

Currently Quantitative Structure Activity Relationship (QSAR) modeling is being employed to analyze the structural principles that govern biological activities amongst host defense peptides (HDPs) (Jenssen et al. *J Pept Sci* (2008) 14:110 and Jenssen et al. *Chem Biol Drug Des* (2007) 70:134). Using this methodology a conserved sequence motif was identified based on multiple sequence alignments of the most active immunomodulatory peptides as follows:

V**R*IRV*VIR (SEQ ID NO:23), where * denotes any amino acid. A set of 6 novel peptides that encompass slight variations of this core motif (L-, D-, and RI-derivatives) were produced with the following sequences:

TABLE 2

| Name | Sequence | SEQ ID | Peptide Concentration (µg/ml) | Chemokine Induction (pg/ml) MCP-1 | Gro-α |
|---|---|---|---|---|---|
| JK1 | VFLRRIRVIVIR | 2 | 20 | 663 | 377 |
| | | | 100 | 1226 | 105 |
| JK2 | VFWRRIRVWVIR | 3 | 20 | 414 | 150 |
| | | | 100 | 286 | 43 |
| JK3 | VQLRAIRVRVIR | 4 | 20 | 873 | 430 |
| | | | 100 | 747 | 320 |
| JK4 | VQLRRIRVWVIR | 5 | 20 | 655 | 245 |
| | | | 100 | 557 | 80 |
| JK5 | VQWRAIRVRVIR | 6 | 20 | 673 | 317 |
| | | | 100 | 529 | 123 |
| JK6 | VQWRRIRVWVIR | 7 | 20 | 721 | 254 |
| | | | 100 | 671 | 68 |

These peptides, as well as their enantiomeric and retroinverso counterparts were synthesized using standard techniques and it was demonstrated that these peptides for induced MCP-1 and Gro-α release in human PBMCs. Interestingly, the retroinverso and enantiomeric versions of these active immunomodulatory peptides were superior to their L-amino acid analogs.

One more panel of peptides was produced as derivatives of indolicidin (Table 3; WO2008022444). Based on their superior activity in ex vivo screening with human PBMCs, four of these peptides were selected for further in vivo analysis in mice. This study demonstrated that HH1010 had stronger in vivo adjuvanticity properties when combined with CpG ODN in comparison to indolicidin.

TABLE 3

Indolicidin derivatives

| Peptide | Sequence | Peptide Concentration | Chemokine Induction (pg/ml) MCP-1 | Gro-α |
|---|---|---|---|---|
| Indolicidin | ILPWKWPWWPWRR (SEQ ID NO: 1) | 20 | 245 | 84 |
| | | 100 | 3120 | 846 |
| HH111 | ILKWKWPWWPWRR (SEQ 1D NO: 24) | 20 | 905 | 328 |
| | | 100 | 346 | 409 |
| HH113 | ILPWKKPWWPWRR (SEQ ID NO: 25) | 20 | 253 | 163 |
| | | 100 | 1615 | 491 |
| HH970 | ILKWKWPWWKWRR (SEQ ID NO: 26) | 20 | 780 | 149 |
| | | 100 | 1133 | 256 |
| HH1010 | ILRWKWRWWRWRR (SEQ ID NO: 27) | 20 | 3487 | 281 |
| | | 100 | 3494 | 918 |

Example 2

Production of Polyphosphazines for Use in Combination Adjuvant Formulations

The polyphosphazines shown in FIG. 1 were synthesized using described techniques (Andrianov et al., *Biomacromolecules* (2004) 5:1999; Andrianov et al., *Macromolecules* (2004) 37:414; Mutwiri et al., *Vaccine* (2007) 25:1204). In particular, hexachlorocyclotriphosphazene [(N=PCL$_2$)$_3$] was converted to polydichlorophosphazene (PDCP) using ring-opening polymerization (ROP). See, FIG. 2A. In order to do so, (N=PCL$_2$)$_3$ was sublimed, transferred to a glass tube and flame sealed under high vacuum, as described in Singler et al., *J. Poly. Sci. Polym. Chem. Ed.* (1974) 12:433; Allcock, H. R., Phosphorus-Nitrogen Compounds, Academic: New York, 1972; Gleria et al., *Top. Curr. Chem.* (2005) 250:165; De Jaeger et al., *Prog. Polym. Sci.* (1998) 23:179. The ROP reaction and its affiliated conditions destroy virtually any organic contaminants introduced during reactant preparation. The reaction time ranged from 24 to 48 hours at 250° C. The linear polymer PDCP is formed during this process. PDCP was isolated by precipitation of the polymer in hexanes.

Figure 2A:
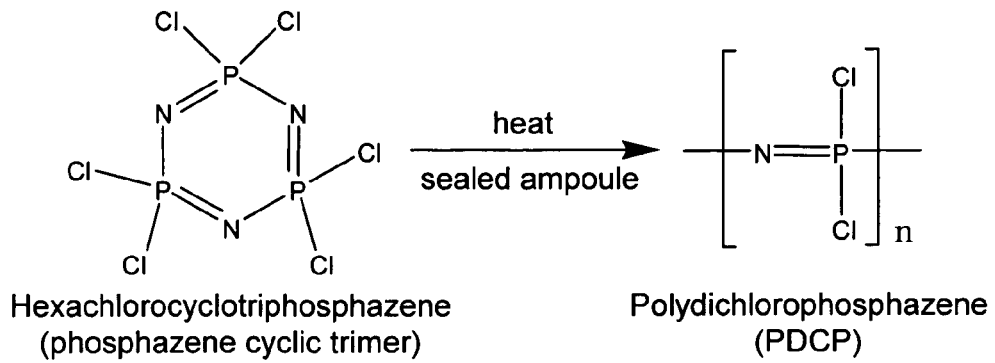
FIGS. 2A-2D show the synthesis scheme for PCPP.
Figure 2B:
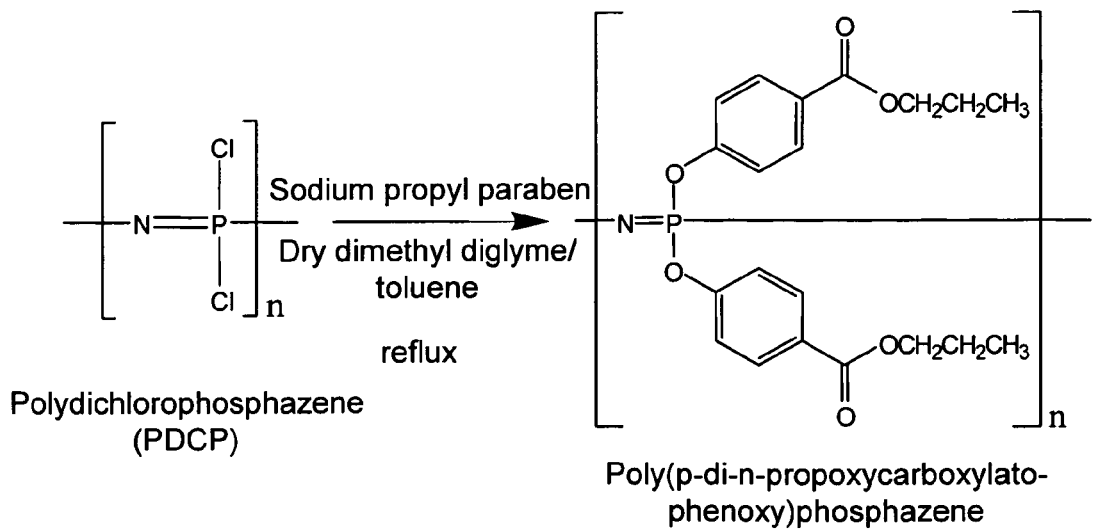

PDCP was then used to produce poly(p-dicarboxylatophenoxy)phosphazene (PCPP) using techniques essentially as described in Andrianov et al., *Biomacromolecules* (2004) 5:1999; Andrianov et al., *Macromolecules* (2004) 37:414; and Mutwiri et al., *Vaccine* (2007) 25:1204) with the following modifications. FIG. 2B shows the first step of the PCPP synthesis technique. Unlike the technique described in the above references, anhydrous toluene provided as a 50:50 mixture of diglyme and toluene was used to dissolve PDCP. This PDCP solution was added directly to a heated sodium propyl paraben solution by cannula and heated to reflux (approximately 115° C.) with mechanical stirring, resulting in the production of poly(p-di-n-propoxycarboxylatophenoxy) phosphazene. This was then used to produce 100% PCPP, 100% PCPP-H, 90:10 PCPP and PCEP as follows.

A. Production of 100% PCPP and 100% PCPP-H

Figure 2C:
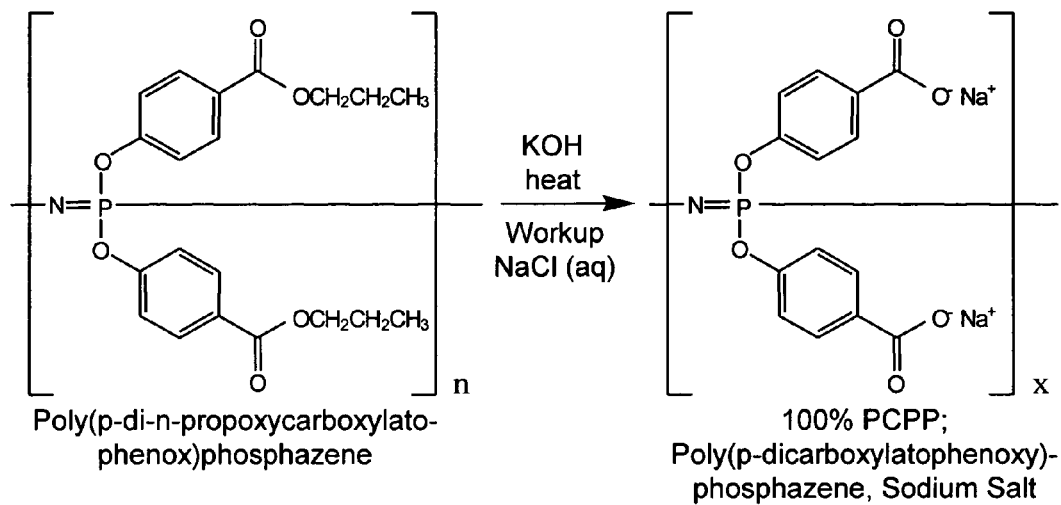

FIG. 2C shows the saponification reaction used to produce 100% PCPP. In order to produce 100% PCPP as the sodium salt, a potassium hydroxide-based method was used (Andrianov et al., *Biomacromolecules* (2004) 5:1999; Andrianov et al., *Macromolecules* (2004) 37:414). The reaction solution from step 1 above was cooled to approximately 90° C., and an aqueous solution of approximately 16M KOH was added and stirred. After stirring for 20-30 minutes, the solution viscosity increased dramatically and the mechanical stirrer was set to approximately 1200 rpm. Caution is needed during this step because the polymer adheres to the walls of the flask. Additional toluene was used to decrease the viscosity. Over time, the polymer broke up into smaller pieces and eventually into white flakes. After this, the solution was cooled to ambient temperature and the polymer precipitated to the bottom of the flask. The organic solvent was decanted and the precipitate dissolved in a saturated aqueous sodium chloride solution. Endotoxin-free water was added as needed. The polymer was again precipitated and rinsed several times with ethanol.

The precipitate was dissolved in endotoxin-free water and transferred to a sterile beaker. Filtration was used to remove insoluble polymer masses from the aqueous solution. The polymer solutions were filtered through a 2.7 μm (or 5.0 μm) Whatman GF/D syringe filter using a sterile syringe. The filtered solution was added directly into a sterile Erlenmeyer flask, followed by autoclaving for 20 minutes. The PCPP salt polymer solution was precipitated in ethanol. The solids were collected and dried in a vacuum oven at about 110° C. and purged with argon.

Figure 2D:
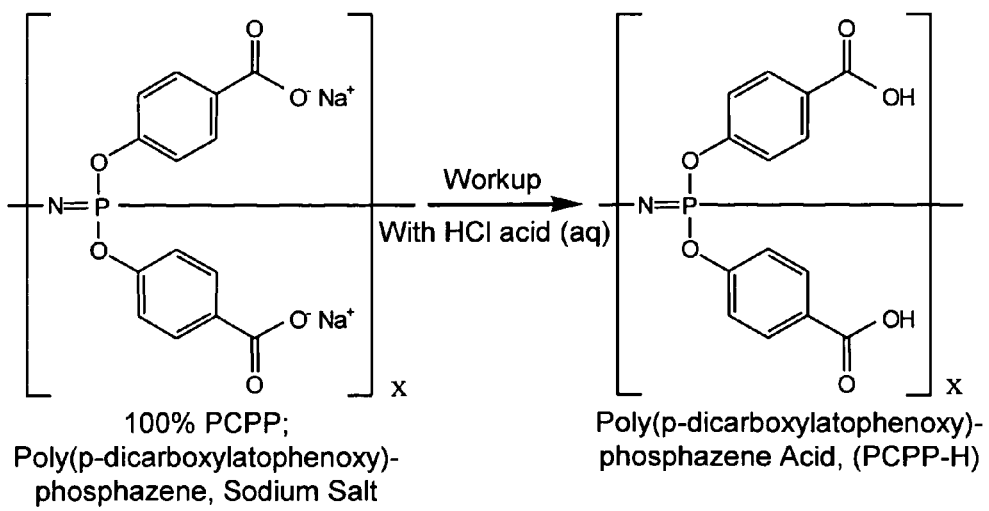

100% PCPP-H, which is the acidified PCPP, was made as shown in FIG. 2D. In particular, the aqueous PCPP sodium salt polymer above was precipitated with clean acidic water (aqueous hydrochloric acid) resulting with poly(p-dicarboxylatophenoxy)phosphazene acid (PCPP-H).

B. Production of 90:10 PCPP/OH

Figure 3:
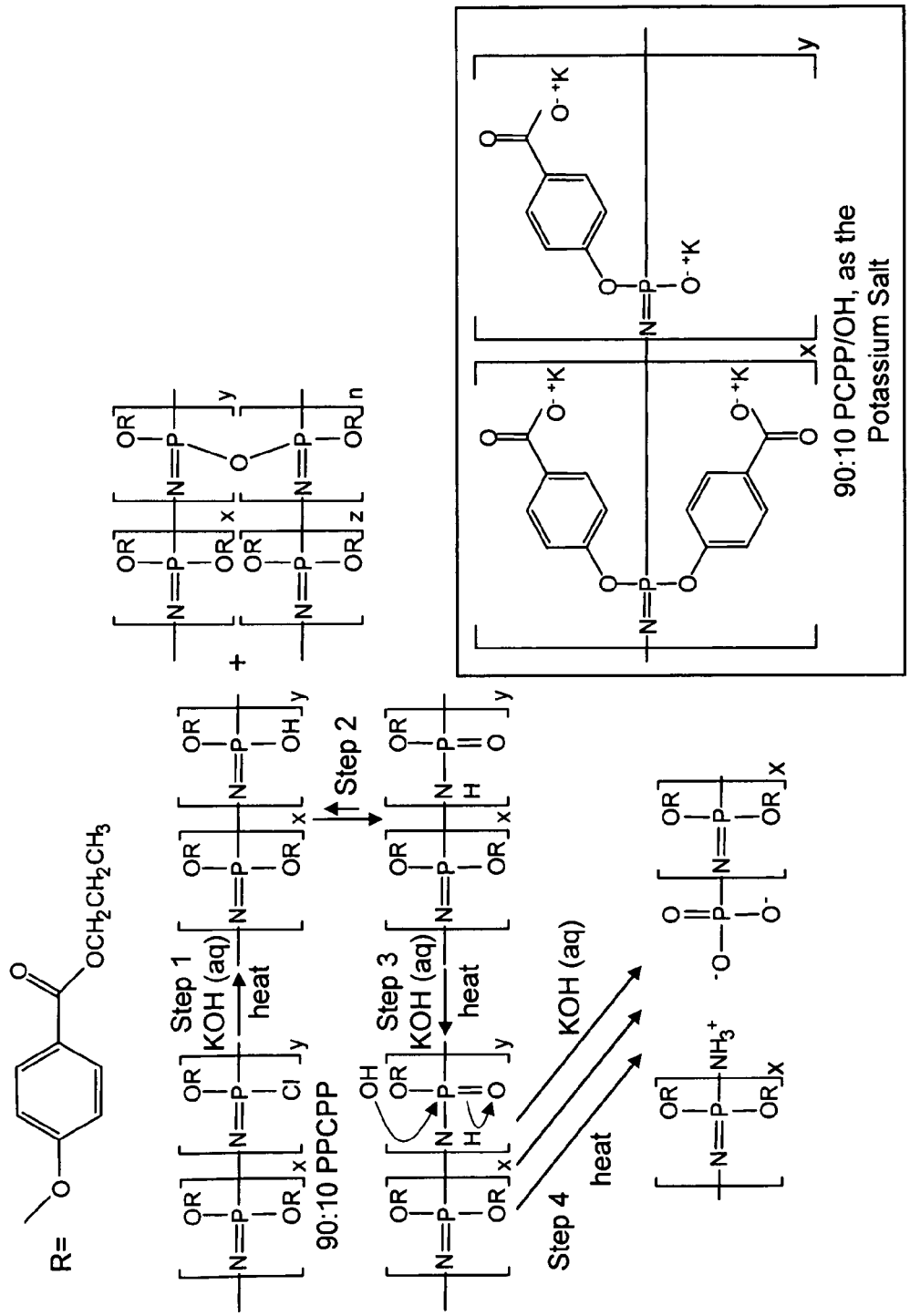
FIG. 3 shows the production scheme for a PCPP polymer comprised of 90% PCPP copolymer with 10% hydroxyl groups (90:10 PCPP).

FIG. 3 shows the production scheme for a PCPP polymer comprised of 90% PCPP copolymer with 10% hydroxyl groups (90:10 PCPP/OH). In order to produce 90:10 PCPP/OH, the solution from step 1 above, containing a 50:50 mixture of diglyme and toluene, was heated to reflux (approximately 115° C.) until 90% substitution was obtained (less than six hours). The solution was cooled to approximately 90° C., and an aqueous solution of 16M KOH was added. The polymer slowly precipitated out of solution (30-60 minutes). If excessive polymer adhered to the walls of the flask, more endotoxin-free water was added. The reaction was stopped by cooling the reaction mixture with an ice bath. The precipitated polymer (or solution) was allowed to settle and organic solvent decanted. The precipitate was dissolved with a saturated sodium chloride aqueous solution and precipitated out of solution by ethanol. The precipitate was washed several more times with ethanol.

The precipitate was dissolved in endotoxin-free water and transferred to a sterile beaker. The polymer solutions were filtered through a 2.7 μm Whatman GF/D syringe filter using a sterile syringe. The 90:10 PCPP salt polymer solution was precipitated in ethanol. The solids were collected and dried in a vacuum oven at about 110° C. and purged with argon.

C. Production of PCEP

Figure 4A:
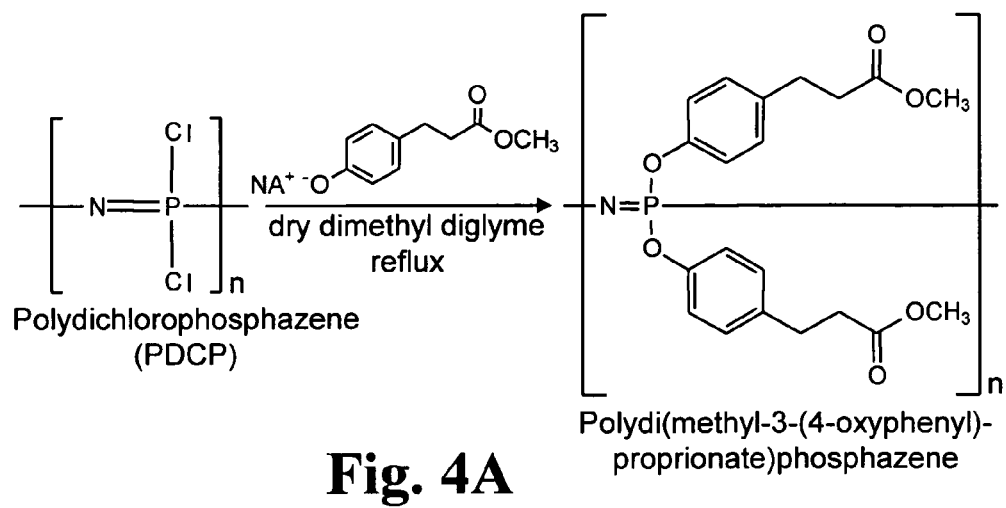
FIGS. 4A and 4B show the synthesis scheme for poly(di-4-oxyphenylproprionate)phosphazene (PCEP).
Figure 4B:
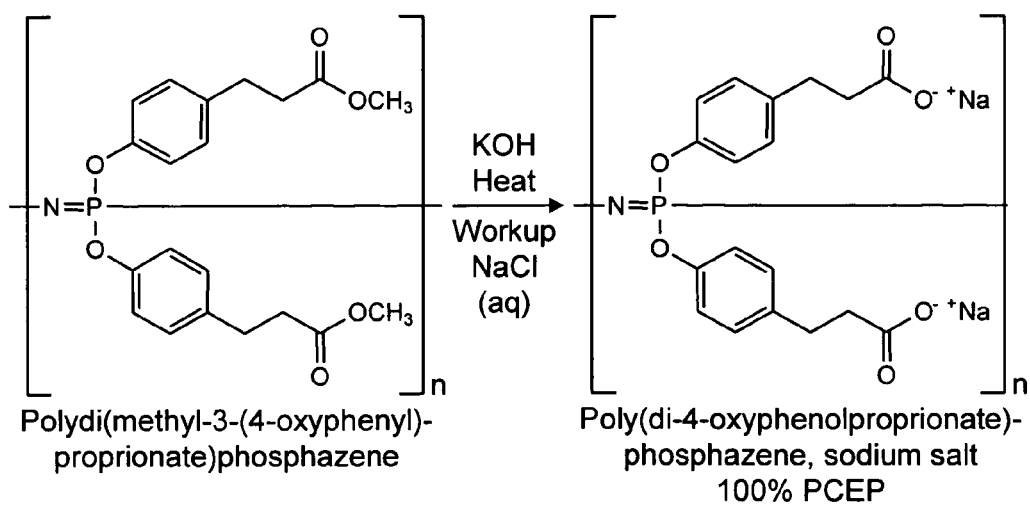

FIGS. 4A and 4B show the production steps for poly(di-4-oxyphenylproprionate)phosphazene (PCEP). The previous PCPP procedures were followed for the PCEP synthesis. In the first step, the substituent (ligand) used was a methyl-protected ester of the hydroxyhyrocinnamate (methyl-3-[4-oxyphenyl]-proprionate). See, FIG. 4A. Then, the previous 100% PCPP synthetic route was used to make the 100% PCEP. See, FIG. 4B.

Example 3

Immunization of Mice Using Combination Adjuvant Formulations

In order to evaluate the efficacy of various adjuvant compounds, the following experiments were done in mice.

A. Materials and Methods

Six- to eight-week-old female C57BL/6 mice (Charles River, Montreal, Quebec) were immunized twice subcutaneously at 3 week intervals with 100 μL of vaccine containing 0.5 μg ΔF from BRSV (a truncated form of the BRSV F protein engineered to lack the transmembrane domain (aa1-522 only), either alone, or co-formulated with CpG oligonucleotide 1826 (CpG ODN), indolicidin (indol), and/or polyphosphazene (PP). CpG ODN, indolicidin and polyphosphazene were given at doses of 10 μg, 20 μg, and 50 μg, respectively. Negative control animals were immunized with buffer (placebo). CpG ODN 1826 (TCCATGA CGTTCCTGACGTT) (SEQ ID NO:8) was provided by Merial (Lyon, France), and contained a phosphorothioate-modified backbone. Indolicidin (ILPWKWPWWPWRR) (SEQ ID NO:1) was chemically synthesized on a Pioneer solid-phase peptide synthesizer (PerSeptive Biosystems, Foster City, Calif.) using 9-fluorenylmethoxy carbonyl (Fmoc) chemistry. The polyphosphazene polymer, 90:10 PCPP/OH, is described above. The ΔF antigen is a truncated version of the BRSV F protein (aa1-522) lacking the transmembrane domain. A comparison of the immune responses to the ΔF protein, alone and formulated with CpG ODN, indolicidin, and polyphosphazene (ΔF/CpG/indol/PP) in C57BL/6 and Balb/c mice was carried out following the immunization protocol described above.

The vaccine composed of ΔF formulated with CpG ODN, indolicidin, and polyphosphazene (ΔF/CpG/indol/PP) was further evaluated for its ability to enhance protection against BRSV. Six- to eight-week-old female Balb/c mice (Charles River) were immunized twice subcutaneously at 3 week intervals with 0.5 μg of ΔF alone or combined with CpG ODN 1826, indolicidin and polyphosphazene (ΔF/CpG/indol/PP). Negative control animals were immunized with buffer alone (placebo). Two weeks following the second immunization, mice were challenged intranasally with $10^7$ p.f.u. of BRSV strain 375, in a final volume of 50 μL. Mock challenged animals were given 50 μL of saline intranasally. Four days following challenge, lungs were collected from half of the mice for detection of viral RNA, and IL-5 and eotaxin production. Six days following challenge, spleens were collected from the remaining mice for analysis by enzyme-linked immunospot (ELISPOT) assay. Bronchoalveaolar lavage fluids were collected from each group and pooled. Cytospin slides were prepared using $1\times10^5$ and $5\times10^4$ cells, and stained with Wright-Giemsa stain (Bayer HealthCare, Toronto, Ontario). The numbers of macrophages, neutrophils, lymphocytes and eosinophils for each group were determined by examination of at least 200 cells. All procedures were carried out in accordance with the guidelines of the Canadian Council for Animal Care.

Statistical analysis was carried out using GraphPad Prism version 5.00 for Windows (GraphPad Software, San Diego, Calif.). Differences between groups were determined using a Mann-Whitney U test.

B. Results

Co Formulation of Ova with CpG ODN, Indolicidin, and Polyphosphazene

Figure 5A:
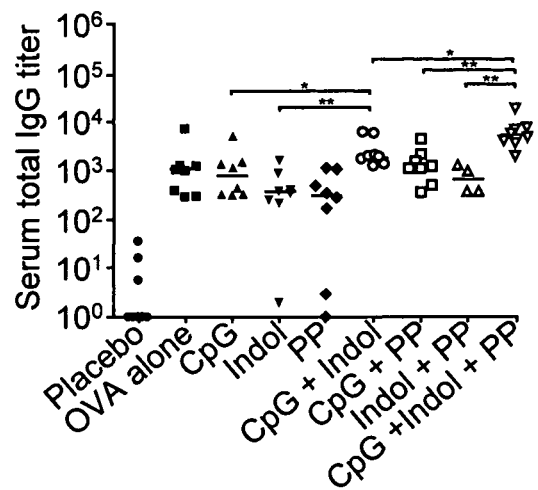
FIGS. 5A-5D show OVA-specific IgG1 (FIGS. 5A and 5C) and IgG2a (FIGS. 5B and 5D) titres following one immunization (FIGS. 5A and 5B) or two immunizations (FIGS. 5C and 5D) as described in the examples.
Figure 5B:
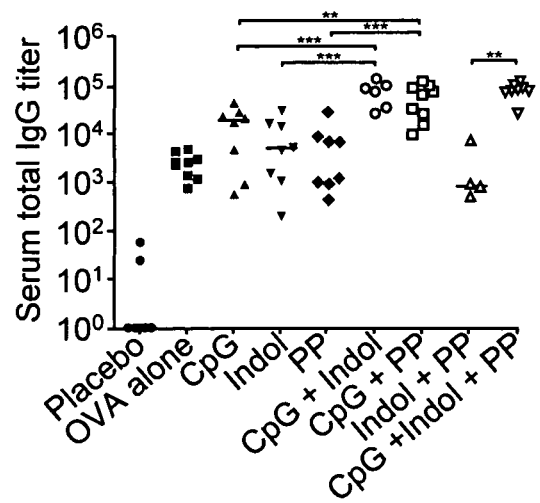

The adjuvant activity of the combination of CpG ODN and indolicidin was examined by co-formulation of CpG ODN, indolicidin and polyphosphazene. Mice were immunized with a sub-optimal dose of OVA (10 µg), either alone or co-formulated with CpG ODN (CpG), indolicidin (indol), and/or polyphosphazene (PP), at doses of 10 µg, 10 nmoles, and 50 µg, respectively. Control mice were immunized with buffer (placebo). Serum total IgG titers were measured by ELISA after one immunization (FIG. 5A), and again two weeks later following the second immunization (FIG. 5B). The combination of OVA with CpG ODN complexed with indolicidin induced significantly higher serum total IgG titers than mice immunized with either CpG ODN or indolicidin alone, following one ($P<0.05$ and $P<0.01$) and two ($P<0.001$) immunizations.

The inclusion of polyphosphazene in the formulation significantly enhanced IgG titers after only one immunization. After two immunizations, IgG titers induced by OVA formulated with either CpG+indol ($P<0.001$) and CpG+PP ($P<0.05$ and $P<0.001$) were significantly higher than those induced by the individual adjuvants, however no significance was observed between the titers in these two groups and those induced by the combination of all three adjuvants, CpG+indol+PP.

Figure 5C:
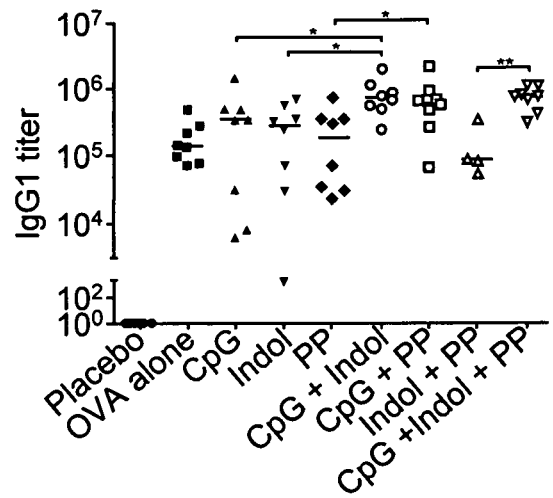
Figure 5D:
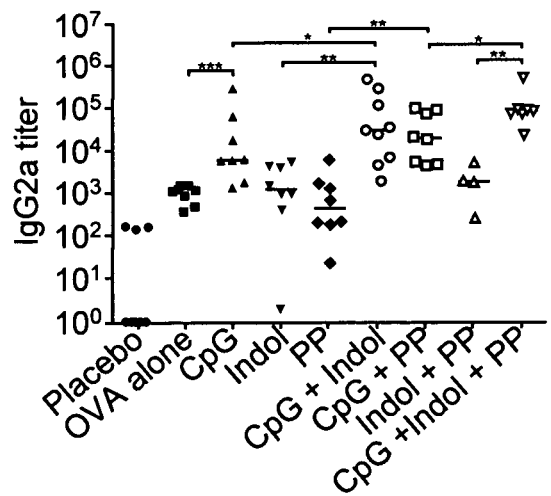

Further analysis of the humoral anti-OVA immune response induced by each of the formulations was carried out by measuring serum subclass IgG1 and IgG2a titers following two immunizations. A trend similar to that observed for the total IgG titers was observed for IgG1, with higher IgG1 titers observed in mice immunized with CpG+indol, CpG+PP, and CpG+indol+PP (FIG. 5C). Significantly higher levels of IgG2a were observed in groups immunized with CpG+indol and CpG+indol+PP (FIG. 5D), suggesting that the combination of CpG and indolicidin may support the induction of a balanced immune response.

Figure 6A:
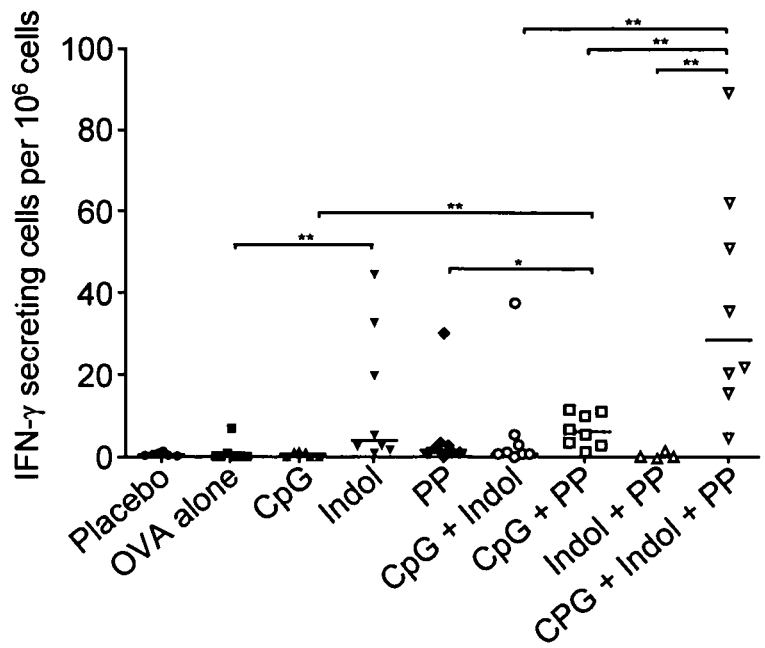
FIGS. 6A and 6B show antigen-specific cytokine secretion following immunization with OVA and selected vaccine formulations, as described in the examples.
Figure 6B:
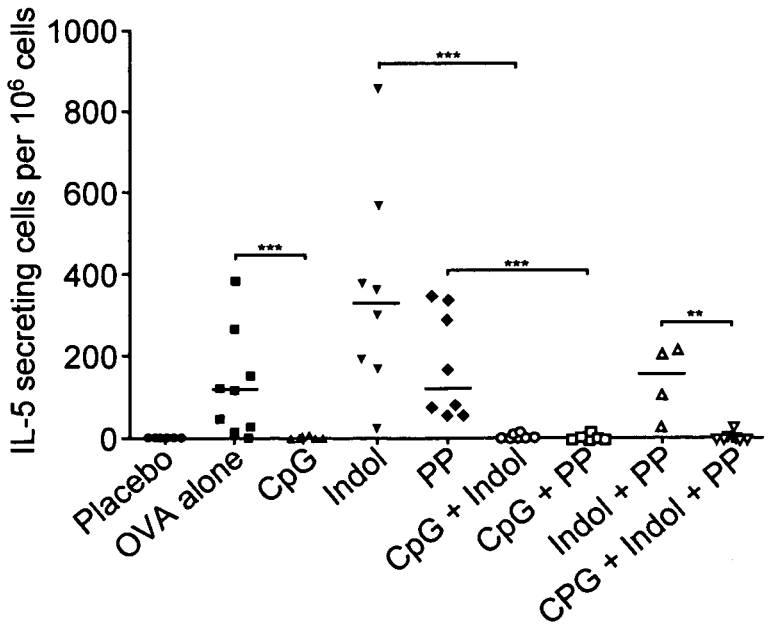

To further characterize the immune response induced by each of the formulations, cellular immune responses were examined by re-stimulating primed splenocytes with OVA or the OVA-derived MHC class I-restricted peptide SIINFEKL. Following re-stimulation with OVA, significantly higher numbers of IFN-γ-secreting cells were observed in mice immunized with antigen co-formulated with all three adjuvants (CpG+indol+PP) when compared to IFN-γ secretion by splenocytes from all other vaccine groups, including those formulated with the two adjuvant combinations ($P<0.01$) (FIG. 6A). All formulations which did not contain CpG ODN resulted in significantly higher frequencies of IL-5-secreting cells when compared to OVA formulations with CpG ODN (FIG. 6B). Moreover, immunization with OVA co-formulated with CpG+indol+PP significantly increased IFN-γ secretion in response to the epitope SIINFEKL, indicating that the co-formulation of OVA with CpG ODN, indolicidin and polyphosphazene also enhanced antigen-specific CD8 T cell responses. These results suggest that while the combination of CpG ODN and indolicidin was capable of enhancing anti-OVA antibody titers, it did not as effectively enhance cellular immune responses. Co-formulation of OVA with CpG ODN, indolicidin, and polyphosphazene, however, led to significant increases in both humoral and cellular immune responses, with a Th1 bias.

Humoral and Cell-Mediated Immune Responses after Immunization with ΔF Formulated with CpG ODN, Indolicidin and Polyphosphazene CpG ODN 1826, indolicidin, and polyphosphazene were examined for their ability to enhance antigen-specific immune responses when administered with the ΔF protein, either alone, or co-formulated with CpG, indolicidin, and/or PP. CpG ODN, indolicidin and polyphosphazene were given at doses of 10 µg, 20 µg, and 50 µg, respectively. Negative control animals were immunized with buffer (placebo)

In order to examine the efficacy of each of the adjuvant compounds, vaccines were formulated with a sub-optimal amount of ΔF protein (0.5 µg/dose), a dose which had been established in a previous dose-titration study. Mice were immunized twice subcutaneously, and serum total anti-ΔF IgG titers were measured after each immunization by ELISA. One mouse in the ΔF/PP group died and was excluded from analysis.

Figure 7A:
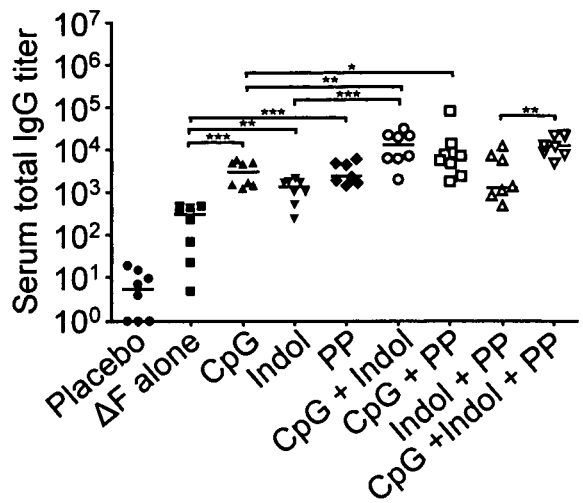
FIGS. 7A-7D show ΔF-specific antibody responses in sera of immunized mice. Total serum anti-ΔF IgG titers were measured after one (FIG. 7A) and two (FIG. 7B) immunizations. IgG1 (FIG. 7C) and IgG2a (FIG. 7D) titers were measured after two immunizations. Each data point represents an individual animal, and median values are indicated by horizontal lines. *, $P<0.05$; , $P<0.01$; *, $P<0.001$.
Figure 7B:
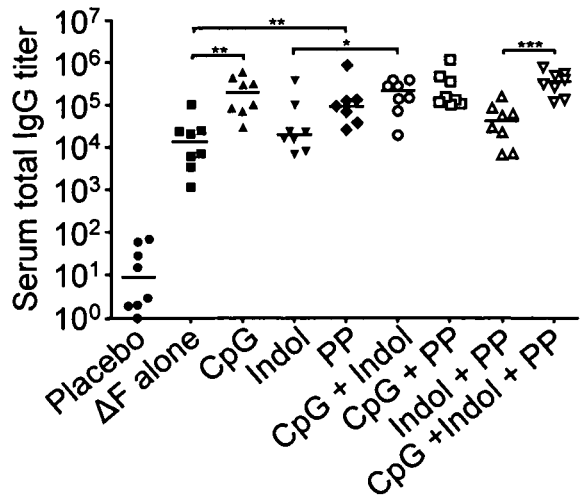

While the total IgG titers elicited by all adjuvants were significantly higher than those of groups immunized with ΔF alone after one immunization (FIG. 7A), mice immunized with ΔF/CpG/indol also developed significantly higher titers than the corresponding single-component vaccine groups. Furthermore, mice immunized with ΔF/CpG/PP or ΔF/CpG/indol/PP had higher titers than the corresponding groups not immunized with CpG. Following two immunizations the IgG titers of all groups, with the exception of those immunized with ΔF/indol and ΔF/indol/PP, were significantly higher than groups immunized with ΔF alone (FIG. 7B). Titers induced by immunization with ΔF/indol or ΔF/indol/PP were not significantly higher than ΔF alone, and were significantly lower than those elicited by all other adjuvant groups.

Figure 7C:
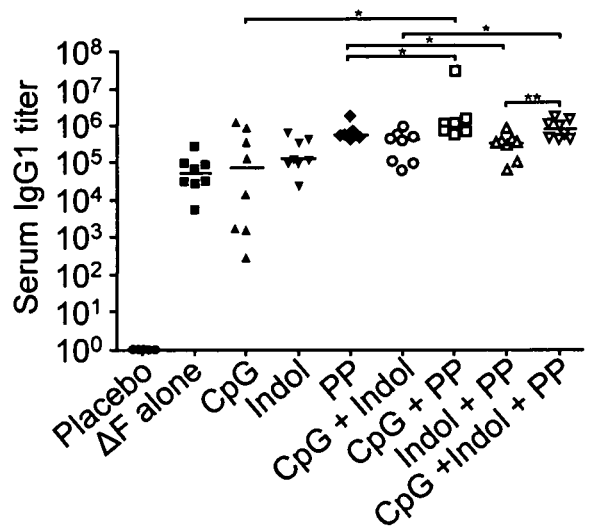
Figure 7D:
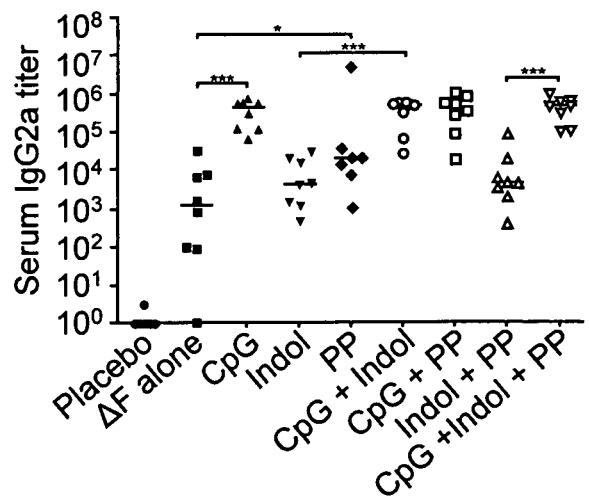

Determination of serum IgG1 and IgG2a subclass titers revealed that all of the vaccine formulations were capable of eliciting high IgG1 antibody titers, with the highest titers observed in the groups immunized with ΔF/CpG/PP and ΔF/CpG/indol/PP (FIG. 7C). However, CpG-containing formulations also resulted in IgG2a titers which were significantly higher than those observed in the groups not immunized with CpG ODN (FIG. 7D), suggesting the induction of a Th1-biased immune response.

Figure 8A:
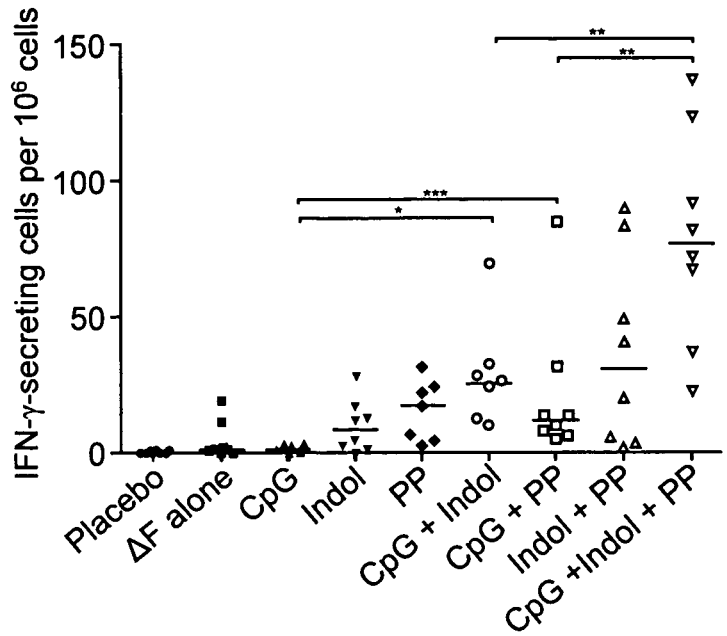
FIGS. 8A and 8B show numbers of IFN-γ-secreting (FIG. 8A) and IL-5 secreting (FIG. 8B) splenocytes in response to in vitro restimulation with ΔF. Results are expressed as the difference between the number of cytokine-secreting cells in ΔF-stimulated wells and medium-control wells per $10^6$ cells. Each data point represents an individual animal, and median values are indicated by horizontal lines. *, $P<0.05$; , $P<0.01$; *, $P<0.001$.
Figure 8B:
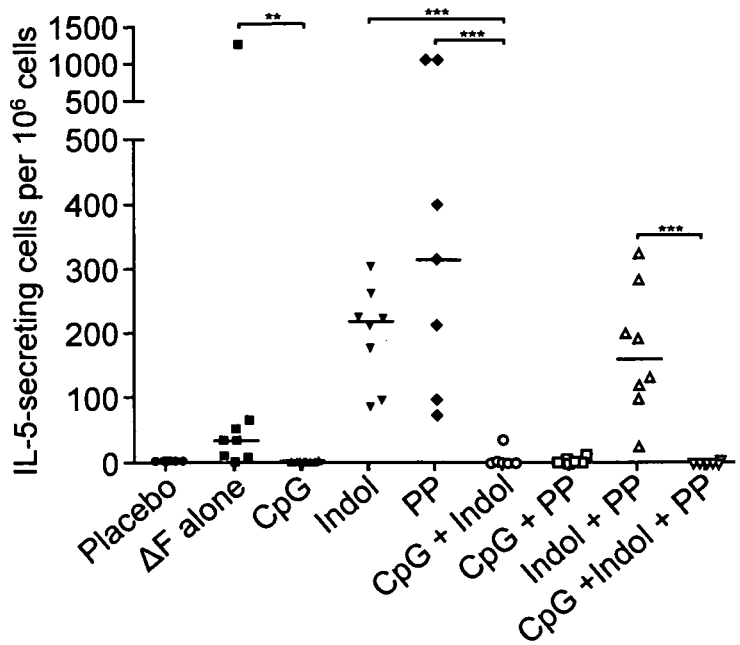

ΔF-induced secretion of IFN-γ and IL-5 by in vitro re-stimulated splenocytes was measured after the second immunization, in order to further evaluate the immune response induced by the ΔF protein when co-formulated with the different adjuvant components. A marked increase in the frequency of IFN-γ-secreting cells was observed in mice immunized with ΔF/CpG/indol/PP when compared to IFN-γ secretion in all other vaccine groups (FIG. 8A). Significantly fewer IL-5-secreting cells were observed in all groups immunized with CpG-containing formulations (FIG. 8B).

These results suggest that the ΔF protein alone induced a Th2-biased immune response. However, the inclusion of CpG ODN in the vaccine formulations resulted in a shift towards a Th1 or balanced immune response. On the other hand, indolicidin and polyphosphazene, in the absence of CpG ODN, appeared to sustain the type-2 immune response induced by ΔF. Only the combination of all three adjuvants, ΔF/CpG/indol/PP, demonstrated a significant enhancement of both the ΔF-specific humoral and cellular immune responses, and was therefore selected for further characterization as a potential BRSV vaccine candidate.

Comparison of Immune Responses in C57BL/6 and Balb/c Mice

Balb/c mice are permissive to RSV infection, and are therefore most commonly used for RSV and BRSV challenge studies. They are, however, more likely to develop a Th2-skewed immune response than C57BL/6 mice. Therefore, the immune response to ΔF formulated with the combination of CpG ODN, indolicidin and polyphosphazene was further evaluated in both strains of mice. Mice were immunized subcutaneously with ΔF alone, or ΔF/CpG/indol/PP. Control mice were immunized with buffer (Placebo). After two immunizations, serum subclass titers were measured in order to determine whether immunization with ΔF/CpG/indol/PP could similarly increase antigen-specific IgG1 and IgG2a levels in both strains of mice. One Balb/c mouse in the ΔF/CpG/indol/PP group died and was excluded from analysis.

Figure 9A:
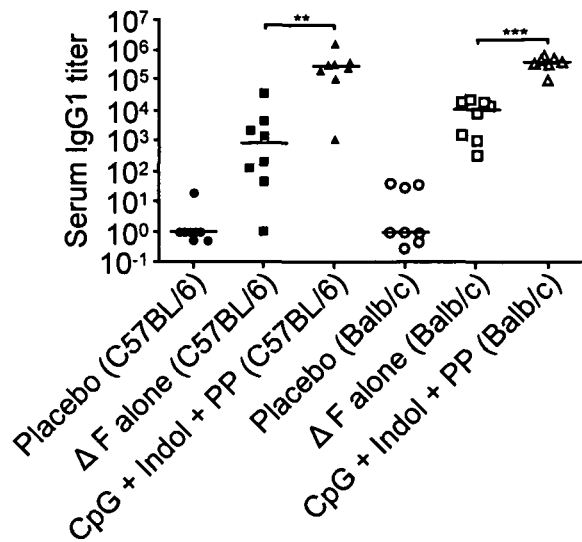
FIGS. 9A-9D show a comparison of ΔF-specific immune responses in C57BL/6 (shaded symbols) and Balb/c (open symbols) mice.
Figure 9B:
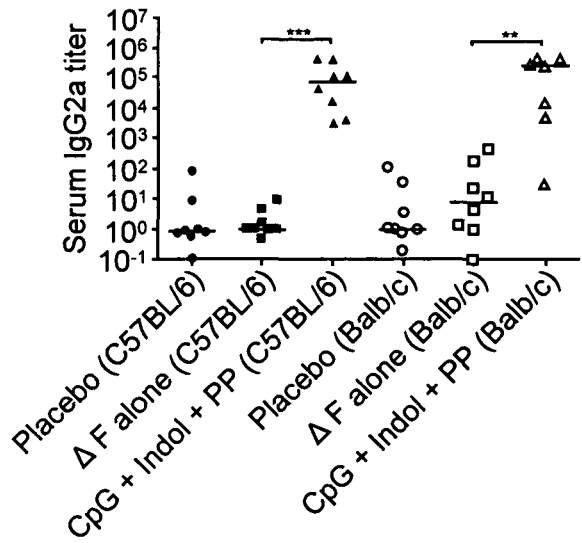
Figure 9C:
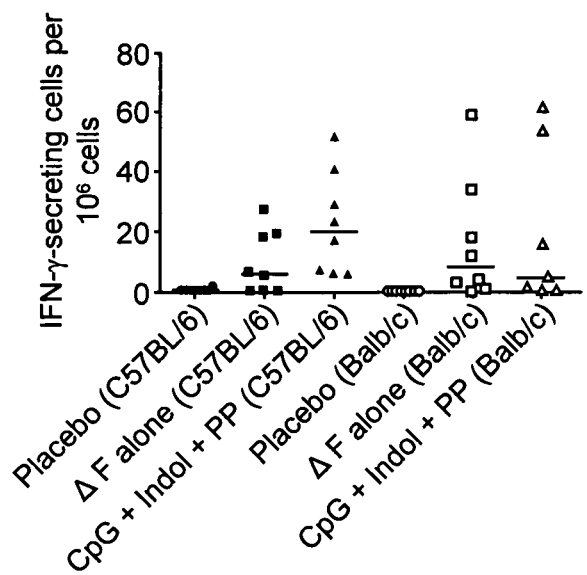
Figure 9D:
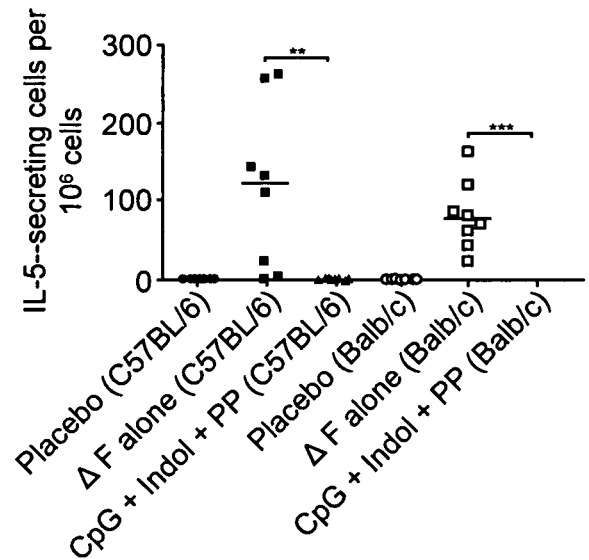

Mice immunized with AΔF/CpG/indol/PP developed significantly higher IgG1 (FIG. 9A) and IgG2a (FIG. 9B) titers than those immunized with ΔF alone. There was no significant difference in the number of IFN-γ-secreting cells between the two strains (FIG. 9C), and both strains demonstrated a decrease in the number of IL-5 secreting cells when immunized with ΔF/CpG/indol/PP (FIG. 9D).

ΔF-Specific Humoral and Cell-Mediated Immune Responses in Mice Immunized with ΔF Protein Formulated with CpG ODN, Indolicidin and Polyphosphazene, and Challenged with BRSV In order to evaluate the protective efficacy of the ΔF protein when formulated with CpG ODN, indolicidin, and polyphosphazene against BRSV, mice were immunized twice subcutaneously with either ΔF alone or ΔF/CpG/indol/PP, and challenged with strain 375 of BRSV two weeks after the second vaccination. Control mice were immunized with buffer, and were challenged with BRSV or mock-challenged with saline.

Figure 10A:
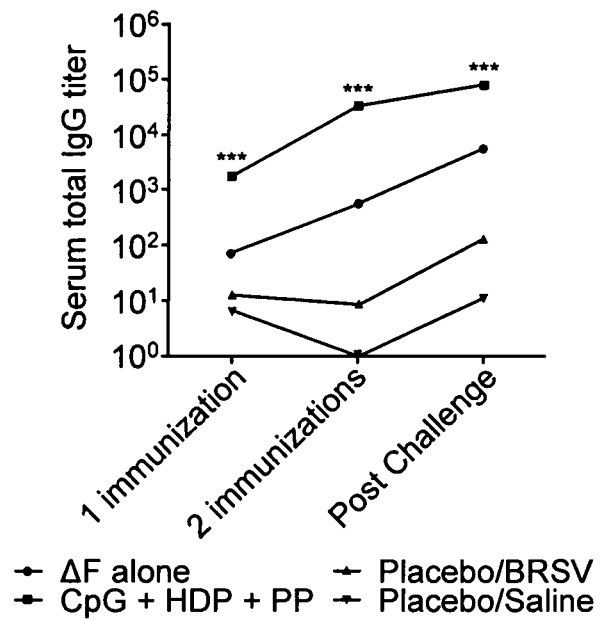
FIGS. 10A-10D show ΔF-specific serum IgG responses in mice as detailed in the examples.
Figure 10B:
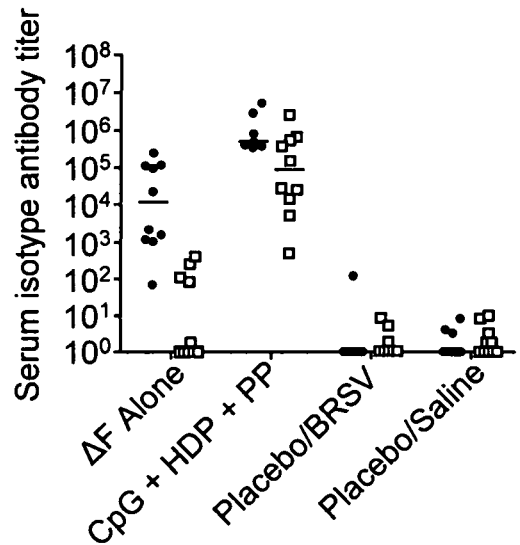
Figure 10C:
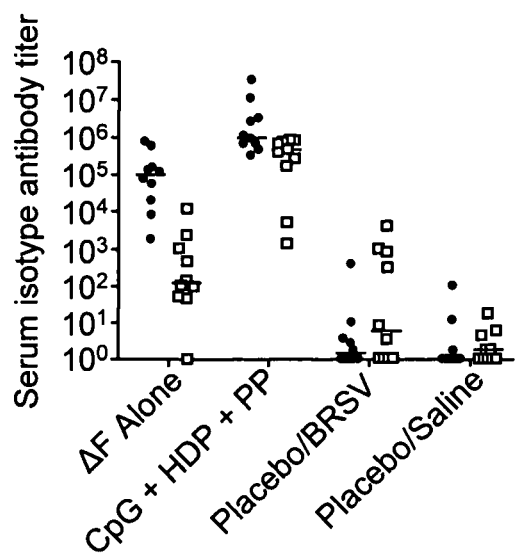
Figure 10D:
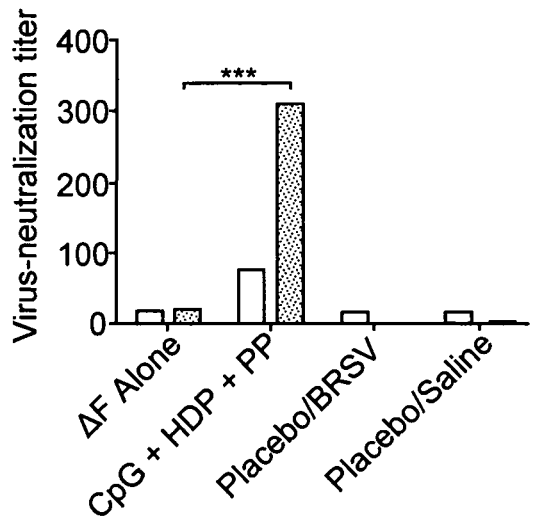

As observed in the previous trials, serum total IgG responses were significantly higher in mice immunized with ΔF/CpG/indol/PP than in mice immunized with ΔF alone (FIG. 10A). This was evident in both the primary and secondary immune responses, as well as after challenge. In both groups, titers increased following the second immunization as well as after challenge, suggesting the induction of an anamnestic response. Likewise, determination of serum subclass titers revealed significantly higher IgG1 and IgG2a production in mice immunized with ΔF/CpG/indol/PP, both after two immunizations (FIG. 10B) and after challenge (FIG. 10C). The ability of the resulting serum antibodies to neutralize the virus in vitro was assessed using a virus neutralization assay. Immunization with ΔF/CpG/indol/PP induced neutralizing antibody titers which were significantly higher than those elicited by ΔF alone (FIG. 10D), and increased approximately 4-fold following challenge with BRSV.

Figure 11A:
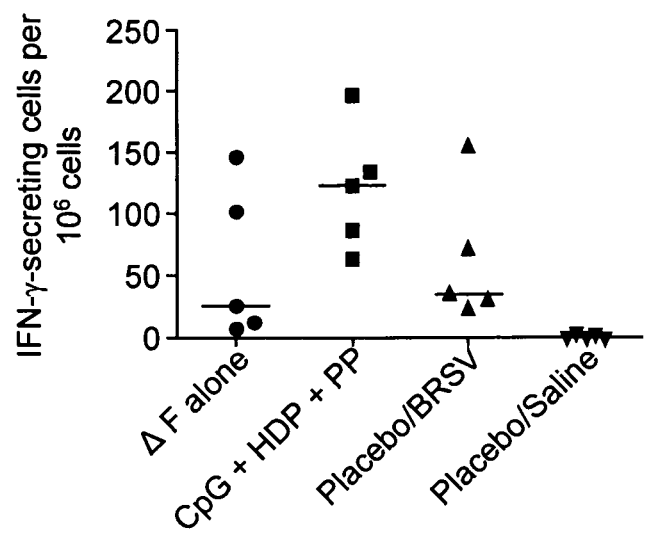
FIGS. 11A and 11B show cellular immune responses in mice immunized with ΔF alone or ΔF/CpG/indol/PP.
Figure 11B:
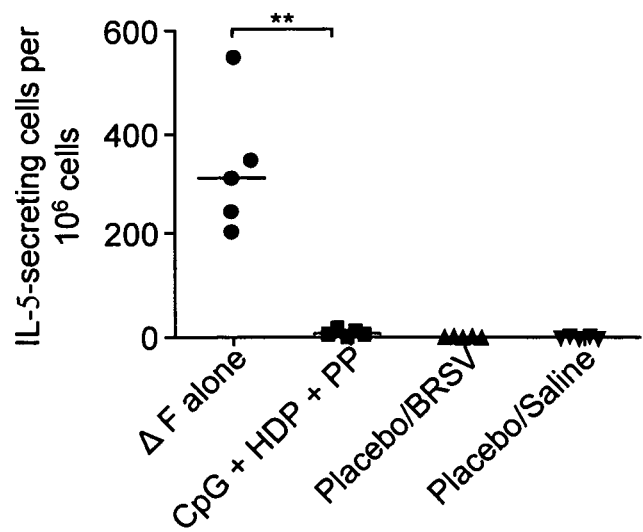

To examine the cellular immune responses generated by each of the vaccines, ΔF-induced secretion of IFN-γ and IL-5 by splenocytes was measured six days after challenge. Although not significantly different, immunization with ΔF/CpG/indol/PP resulted in an increase in the frequency of ΔF-specific IFN-γ-producing splenocytes (FIG. 11A). In contrast, the number of IL-5-producing cells was significantly reduced in mice immunized with ΔF/CpG/indol/PP when compared to immunization with ΔF alone (FIG. 11B). These results further substantiate the ability of the formulation of CpG ODN, indolicidin, and polyphosphazene to shift the immune response generated by ΔF from a Th2 response to a Th1-biased response.

Cytokine/Chemokine Induction and Cell Populations in the Lungs

Lung homogenates were examined for the presence of IL-5 and eotaxin four days after challenge. Mice were immunized twice subcutaneously with ΔF alone or ΔF/CpG/indol/PP and challenged two weeks later with BRSV. Control groups were immunized with buffer and then challenged with BRSV (Placebo/BRSV) or mock-challenged with saline (Placebo/Saline).

IL-5 was only detected in the lungs of mice immunized with ΔF alone, and was absent in all other groups (FIG. 12A). Significantly higher levels of eotaxin, a potent eosinophil chemoattractant, were also detected in mice immunized with ΔF alone, compared to mice immunized with ΔF/CpG/indol/PP (FIG. 12B). Similar results were observed in lungs from animals six days after challenge (data not shown).

Figure 12C:
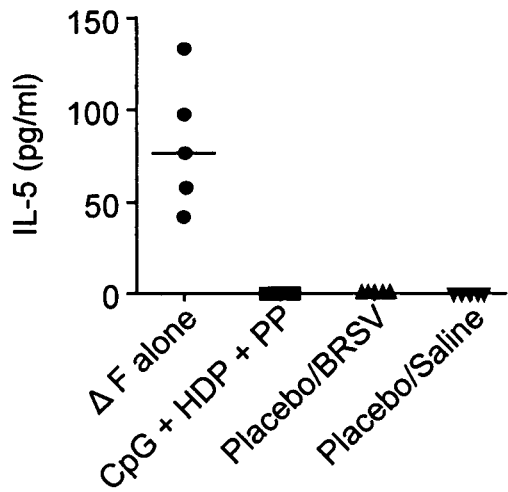
Figure 12C:
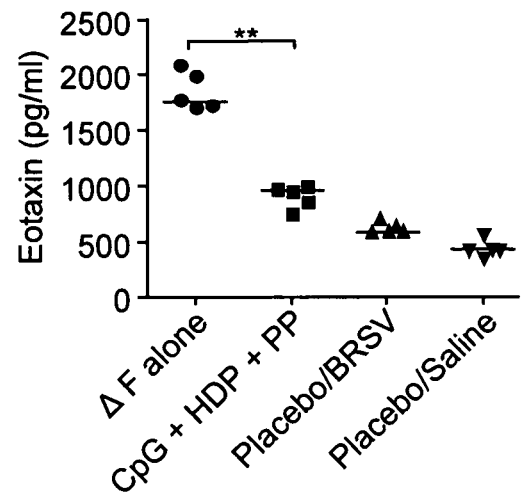
Figure 12C:
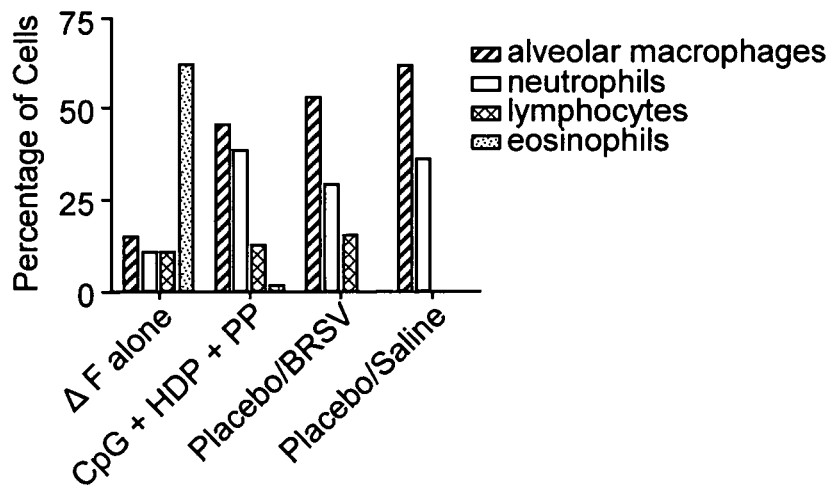

The effect of formulation of ΔF with CpG ODN, indolicidin and polyphosphazene on the pulmonary immune response following BRSV infection was also examined. The percentage of eosinophils present in the lungs of mice immunized with ΔF was 63%, in contrast to 2% in mice immunized with ΔF/CpG/indol/PP (FIG. 12C). No eosinophils were observed in either of the control groups. The percentage of both neutrophils and alveolar macrophages was higher in the control mice and mice immunized ΔF/CpG/indol/PP when compared to ΔF alone, whereas the percentage of lymphocytes was low in all of the groups.

Detection of Viral RNA in the Lungs of Infected Mice

To determine whether immunization with the ΔF/CpG/indol/PP could reduce viral replication, and thereby prevent BRSV infection, viral RNA in the lungs of the mice was measured four days after infection using qRT-PCR. Mice were immunized twice subcutaneously with ΔF alone or ΔF/CpG/indol/PP and challenged two weeks later with BRSV. Control groups were immunized with buffer and then challenged with BRSV (Placebo/BRSV) or mock-challenged with saline (Placebo/Saline).

Figure 13:
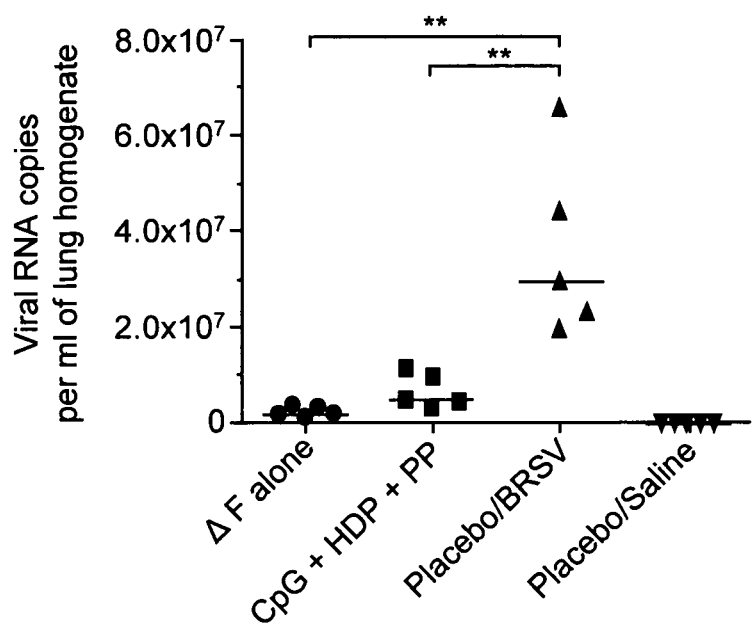
FIG. 13 shows viral RNA copies in lung tissue following immunization and challenge in mice immunized with ΔF alone or ΔF/CpG/indol/PP. Each data point represents an individual animal, and median values are indicated by horizontal lines. **, $P<0.01$.

The amount of viral RNA detected in mice immunized with ΔF/CpG/indol/PP was significantly lower than that detected in the placebo group, as was that in mice immunized with ΔF alone (FIG. 13).

To summarize, the above experiments show that the combination of a host defense peptide with a CpG oligonucleotide and a phosphazine enhances immune responses in mice as compared to the use of these components alone. There still exists no licensed HRSV vaccine, and BRSV vaccines are only moderately effective. Efforts to develop RSV vaccines have been slowed by the inability of candidate vaccines to induce protection against natural infection and the induction of exaggerated disease upon subsequent exposure to the virus, now widely accepted to be due to vaccine-induced type-2 polarized T cell responses. It is therefore essential to identify novel adjuvant candidates which will induce balanced or Th1 responses when co-administered with RSV vaccines.

Evaluation of the adjuvant effects of CpG ODN, indolicidin and polyphosphazene, when co-formulated with the ΔF protein revealed that they were most efficacious when used in combination. Adjuvant doses were selected based on previous reports of adjuvanticity of the individual components. Complete immunostimulatory effects of CpG ODN 1826 have been observed with doses as low as 10 μg (Davis et al., J. Immunol. (1998) 160:870-876), and polyphosphazene when administered at 50 tag per dose has demonstrated enhancement of immune responses even in the presence of low amounts of antigen (Mutwiri et al., Vaccine (2007) 25:1204-1213). Examination of the effect of indolicidin dose and adjuvant activity when co-administered with CpG ODN 1826 indicated that 20 µg of peptide enhanced antigen-specific immune responses and effected class switching to IgG2a better than when the peptide was administered at a 10-fold higher dose (unpublished results). Similar to findings described previously (Hancock et al., Vaccine (2001) 19:4874-4882; Hancock et al., Vaccine (1995) 13:391-400), the ΔF protein, when administered alone, resulted in a predominantly Th2 immune response. In the experiments detailed above, immunization of mice with ΔF co-formulated with a combination of all three adjuvants at the indicated doses led to a significant increase in serum total IgG, IgG1 and IgG2a titers, and significantly increased IFN-γ production, which is important in establishing a protective Th1 antigen-specific immune response to RSV infection, and preventing vaccine-induced disease enhancement (Durbin et al., J. Immunol. (2002) 168:2944-2952).

Hancock et al. (Hancock et al., Vaccine (2001) 19:4874-4882) found that the RSV F protein when administered with CpG ODN in the absence of another adjuvant did not induce significant levels of anti-F total or subclass IgG, or neutralizing antibody. Likewise, mucosal immunization of cotton rats with RSV F protein co-adjuvanted with only CpG ODN resulted in only modest protection from viral challenge and did not prevent the development of enhanced pulmonary pathology (Prince et al., J. Virol. (2003) 77:13156-13160. Mapletoft et al. (Mapletoft et al., J. Gen. Virol. (2008) 89:250-260) observed an increase in antigen-specific IgG titers and frequency of INF-γ-secreting cells following mucosal immunization of mice with a FI-BRSV vaccine co-formulated with CpG ODN and polyphosphazene. The combination of ΔF with CpG ODN and polyphosphazene enhanced antigen-specific humoral immunity.

As detailed in the present experiments, however, inclusion of the cationic cathelicidin peptide indolicidin further enhanced cell-mediated immune responses, suggesting it also plays an important role in the vaccine formulation. In this study indolicidin on its own did not appear to be an effective adjuvant, and promoted a Th2-biased response. The combination of indolicidin, however, along with CpG ODN and polyphosphazene enhanced ΔF-specific humoral and cellular immune responses, and generated a Th1 response. Furthermore, we have recently demonstrated that indolicidin acts synergistically with CpG ODN to increase the production of Th1 cytokines such as IL-12 and IFN-γ, as well as the chemotactic factor MCP-1 (unpublished results). The combination of all three adjuvants was required for optimal enhancement of the immune response, as well as to shift the resulting anti-ΔF immune response from Th2 to Th1. However the mechanisms of this immune enhancement are unclear. Without being bound by a particular theory, the enhanced immunogenicity and Th1-biasing effect of the combination with all three adjuvants with ΔF could be as a result of the stabilization and prolonged effect of CpG ODN and/or ΔF, and an increased uptake of CpG ODN and ΔF into antigen-presenting cells.

Example 4

Figure 14A:
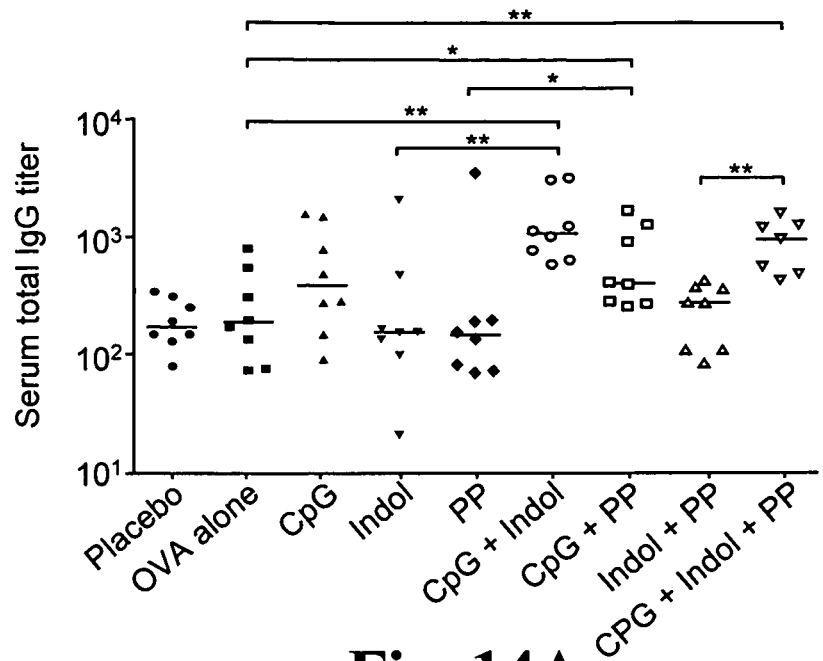
FIGS. 14A and 14B show immune responses in cattle to OVA vaccinated with selected vaccine formulations.
Figure 14B:
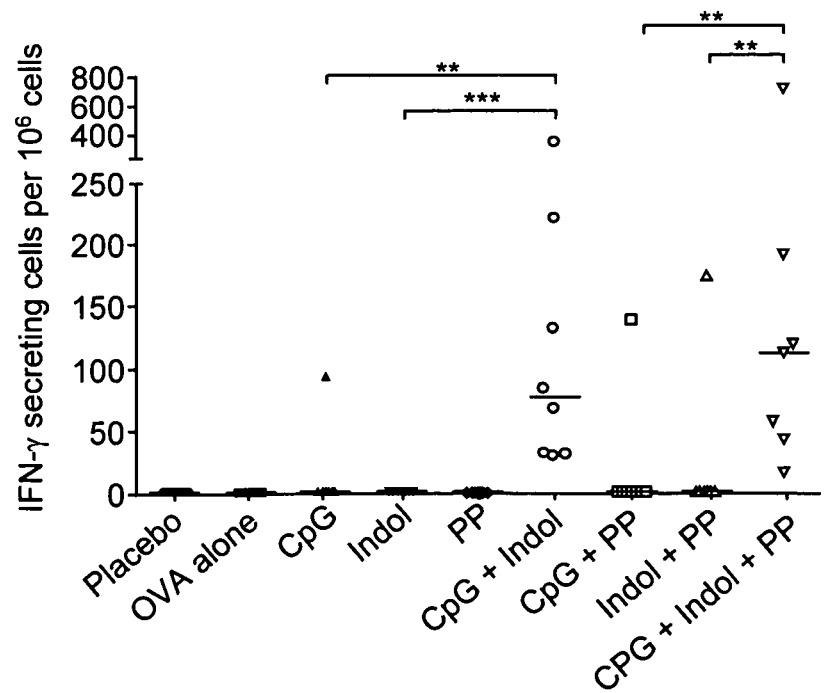

Immunization of Cattle Using Combination Adjuvant Formulations Combined with OVA To determine whether co-formulation with CpG ODN 1826, indolicidin and polyphosphazene polymer 90:10 PCPP/OH could effectively enhance antigen-specific immune responses in a large, outbred species, cattle were immunized with 1 mg ovalbumin (OVA) either alone or co-formulated with CpG ODN, indolicidin, and/or polyphosphazene, at doses of 0.5 mg, 2 mg, and 1 mg, respectively. Control animals were immunized with buffer (placebo). Serum total IgG titers and IFN-γ secretion by re-stimulated PBMCs were measured following two immunizations. Similar to the results observed in mice, immunization with OVA formulated with CpG+indol or CpG+indol+PP increased serum total IgG titers when compared to titers induced by immunization with OVA alone, or OVA combined with the adjuvants individually (FIG. 14A). Likewise, significantly higher numbers of IFN-γ-secreting cells were also observed in these two groups (FIG. 14B), indicating that co-formulation of CpG ODN with indolicidin and polyphosphazene can also enhance antigen-specific immune responses in an outbred population.

Example 5

Immunization of Cattle Using Combination Adjuvant Formulations Combined with HEL To determine whether co-formulation with CpG ODN 2007, indolicidin and polyphosphazene polymer 90:10 PCPP/OH could effectively enhance antigen-specific immune responses in cattle, the following experiments were conducted. CpG ODN 2007 (TCGTCGT-TGTCGTTTTGTCGTT) (SEQ ID NO:9) was provided by Merial (Lyon, France), and contained a phosphorothioate-modified backbone. 90:10 PCPP/OH and indolicidin are described above.

Figure 15A:
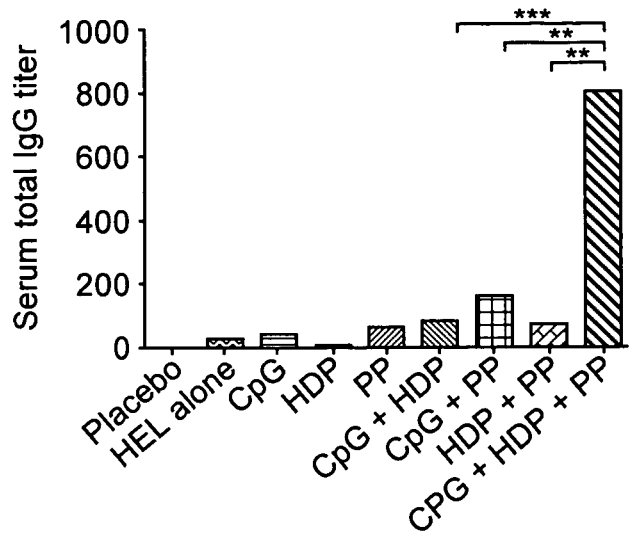
FIGS. 15A-15C show the results of experiments where cattle were immunized with various compositions as indicated.
Figure 15B:
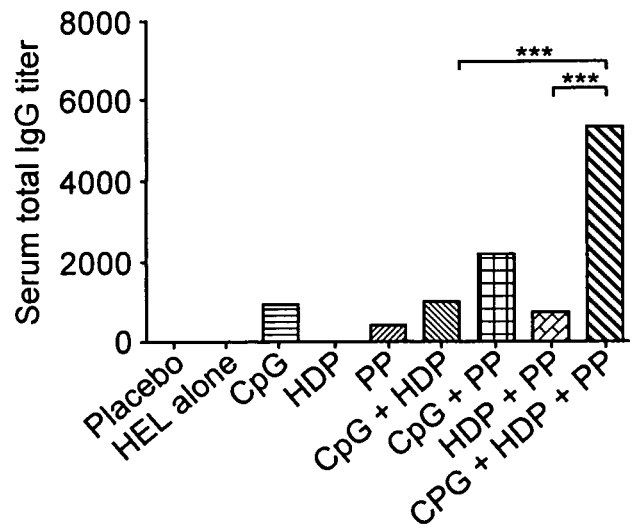
Figure 15C:
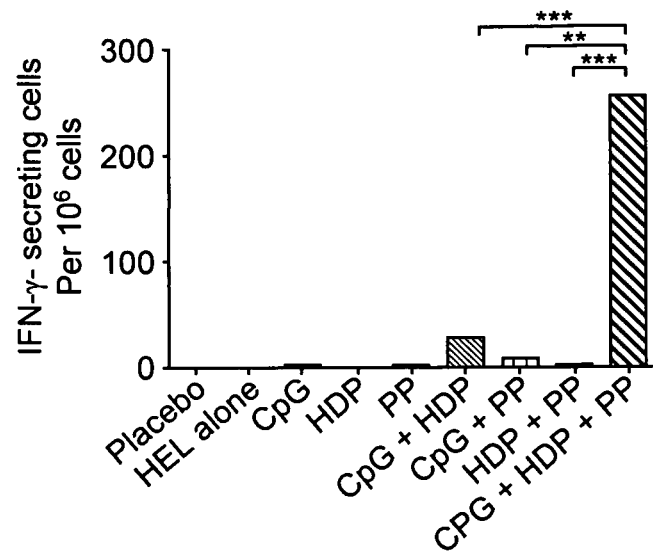

Cows were immunized with hen-egg lysozyme (HEL, Sigma-Aldrich) adjuvanted with CpG ODN 2007 (CpG), indolicidin (HDP), and polyphosphazene (PP) in order to measure HEL-specific humoral and cellular immune responses as follows. Cattle (8/group) were immunized twice subcutaneously with 1 mg of HEL, alone or co-formulated with 500 µg CpG ODN 2007, 2 mg indolicidin, and/or 1 mg polyphosphazene. Serum total anti-HEL IgG titers were measured following primary (FIG. 15A) and secondary (FIG. 15B) immunizations. Following secondary immunization, peripheral blood mononuclear cells (PBMCs) were re-stimulated with 10 µg/mL HEL and numbers of IFN-γ-secreting cells were measured by ELISPOT assay (FIG. 15C). ELISA titers were expressed as the reciprocal of the highest dilution resulting in a reading of two standard deviations above the negative control. ELISPOT results were expressed as the difference between the number of cytokine-secreting cells in HEL-stimulated wells and medium-control wells per $10^6$ cells. Values represent geometric means. *, P<0.05; , P<0.01; *, P<0.001.

As can be seen, co-formulation of HEL with CpG ODN, indolicidin and polyphosphazene led to significantly enhanced immune responses in calves as compared to HEL formulated with either one or two of the adjuvants.

Example 6

Figure 16A:
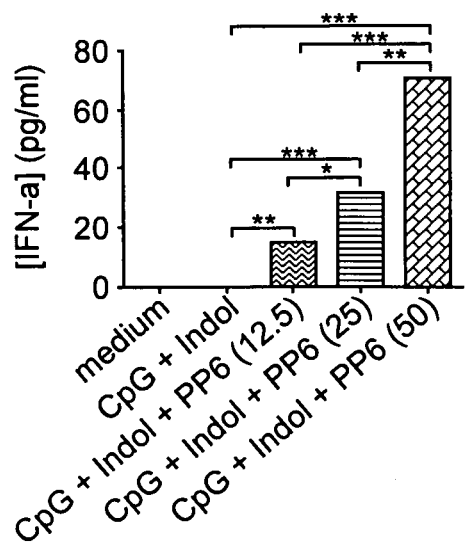
FIGS. 16A-16C show in vitro cytokine secretion by bovine PBMCs stimulated with various combinations of adjuvants at various concentrations.
Figure 16B:
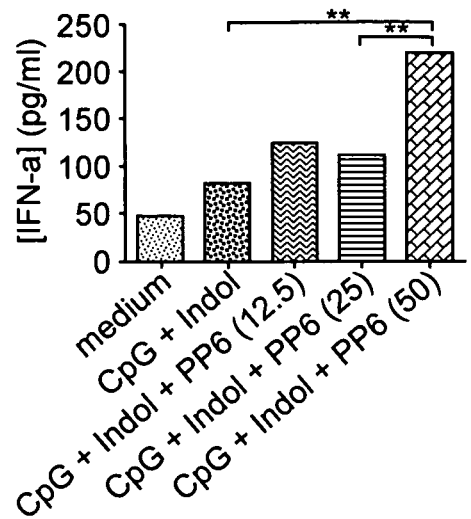
Figure 16C:
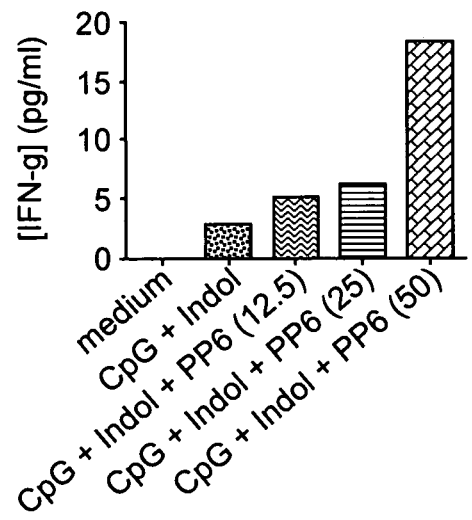

Cytokine Production by Bovine PBMCs In Vitro Following Administration of the Combination Adjuvant Formulations Combined with HEL In order to determine the effects of the combination adjuvant formulation on cytokine production in vitro, the following experiment was conducted. Various, combinations of CpG ODN 2007, indolicidin (indol) and polyphosphazene polymer (90:10 PCPP:OH, labeled as PP6 in the figure) at final concentrations of 0, 12.5, 25, 50 µg/mL, respectively, as shown in FIGS. 16A-16C, were used to stimulate bovine PBMCs for 24 hours. Levels of IFN-α (FIG. 16A), TNF-α (FIG. 16B) and IFN-γ (FIG. 16C) were measured by ELISA. Data shown represent the median values for 8 calves. *, P<0.05; , P<0.01; *, P<0.001.

As can be seen, the triple combination formulation resulted in increased cytokine and chemokine release from immune cells in vitro.

Example 7

Pertussis Toxoid Immune Responses in Mice Using the Combination Adjuvant Formulation In order to determine if the combination adjuvant was effective in eliciting an immune response to pertussis toxoid, the following experiment was conducted. 8 groups of 15 mice were administered various combinations of pertussis toxoid (PTd) obtained from Novartis Vaccines and Diagnostics, Italy, polyphosphazine polymer (PZ#6), CpG oligonucleotide CpG-C 2395 and HH2. Control groups were given either PBS as a negative control or the commercially available vaccine QUADRACEL (Sanofi-Pasteur, Inc) as a positive control. See, Table 5. The polyphosphazine polymer used was 90:10 PCPP:OH, produced as described above. CpG-C 2395 has the sequence TCGTCGTTTTCGGCGCGCGCCG (SEQ ID NO:12) and is fully phosphorothioated and was obtained from Coley Pharmaceuticals. The sequence of the host defense peptide HH2 is shown in Table 1 above. QUADRACEL contains pertussis toxoid as well as additional *Bordetella* protein antigens. Two doses of pertussis toxoid were chosen in order to determine if the adjuvants were able to enhance the immune response to a sub-optimal dose of antigen.

Figure 17:
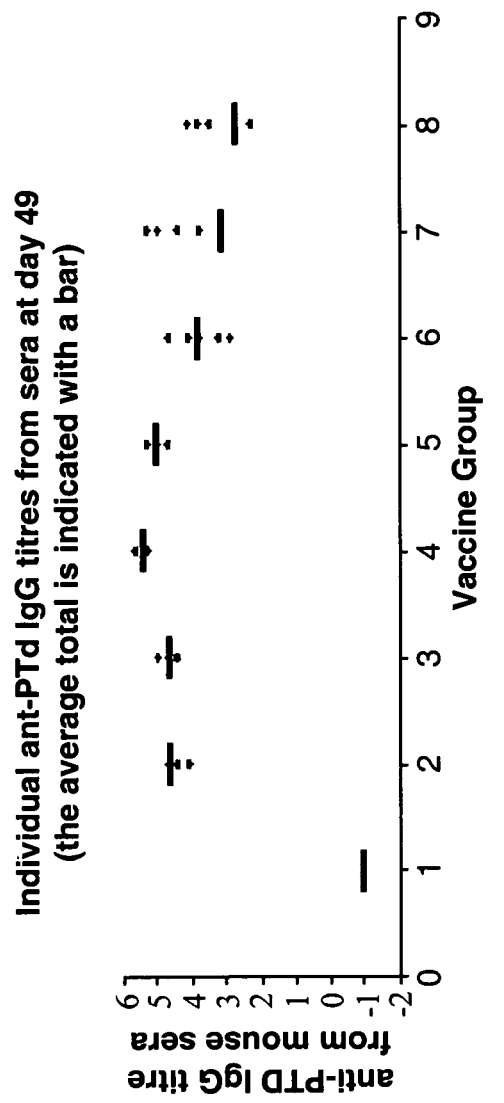
FIG. 17 shows total IgG response to vaccination with pertussis toxoid either alone or co-formulated with various adjuvants as described in the examples. Vaccine groups are as follows: 1-PBS; 2-QUADRACEL; 3-1.0 μg PTd alone; 4-1.0 μg PTd+triple adjuvant; 5-1.0 μg PTd+triple adjuvant (two doses); 6-0.2 μg PTd alone; 7-0.2 μg PTd+triple adjuvant; 8-0.2 μg PTd+triple adjuvant (two doses).
Figure 18:
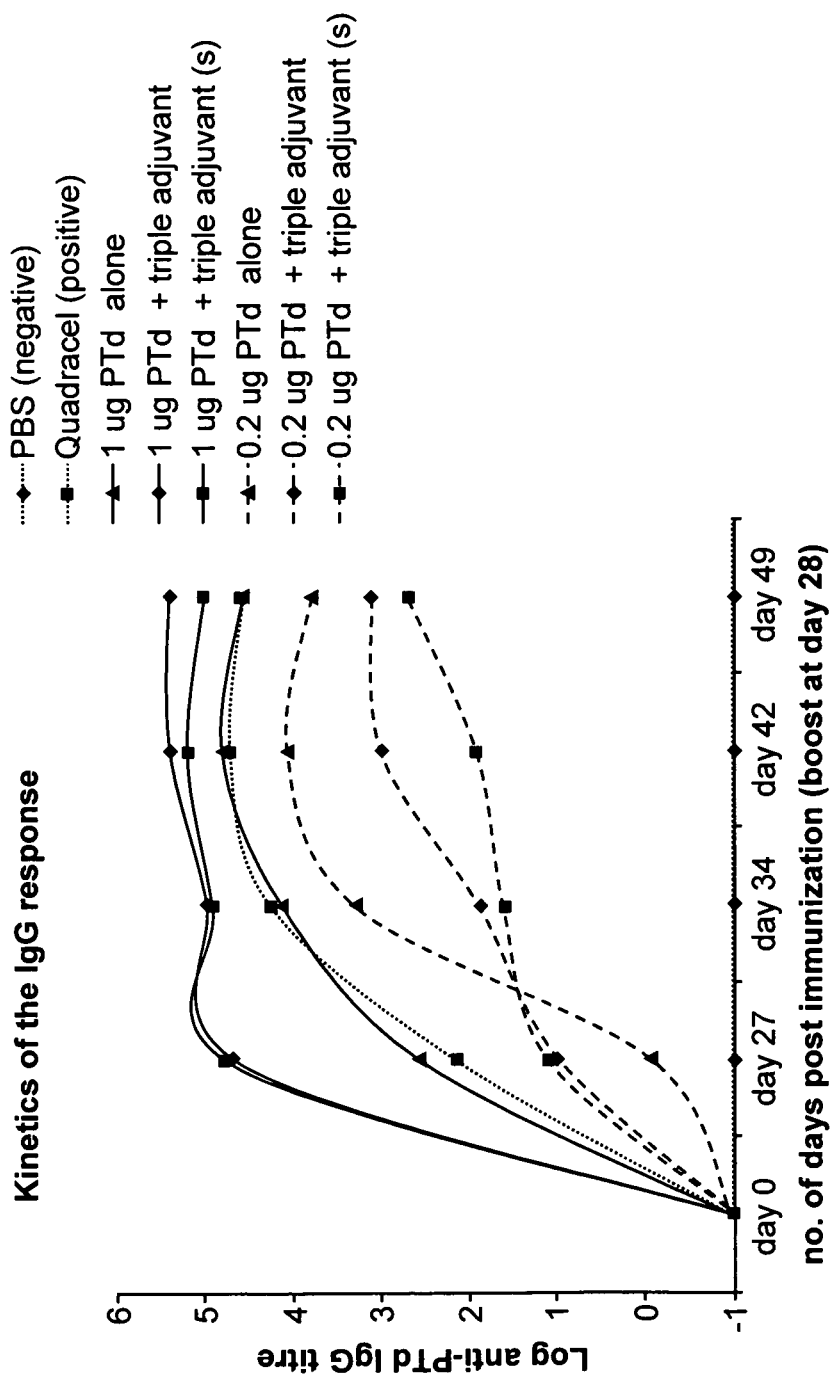
FIG. 18 shows the kinetics of the anti-PTd IgG response to vaccination with pertussis toxoid (PTd) either alone, or co-formulated with various adjuvants as specified. Two groups received two vaccinations of the formulation—the 1 μg PTD+triple adjuvant and 0.2 μg PTd+triple adjuvant groups.
Figure 19:
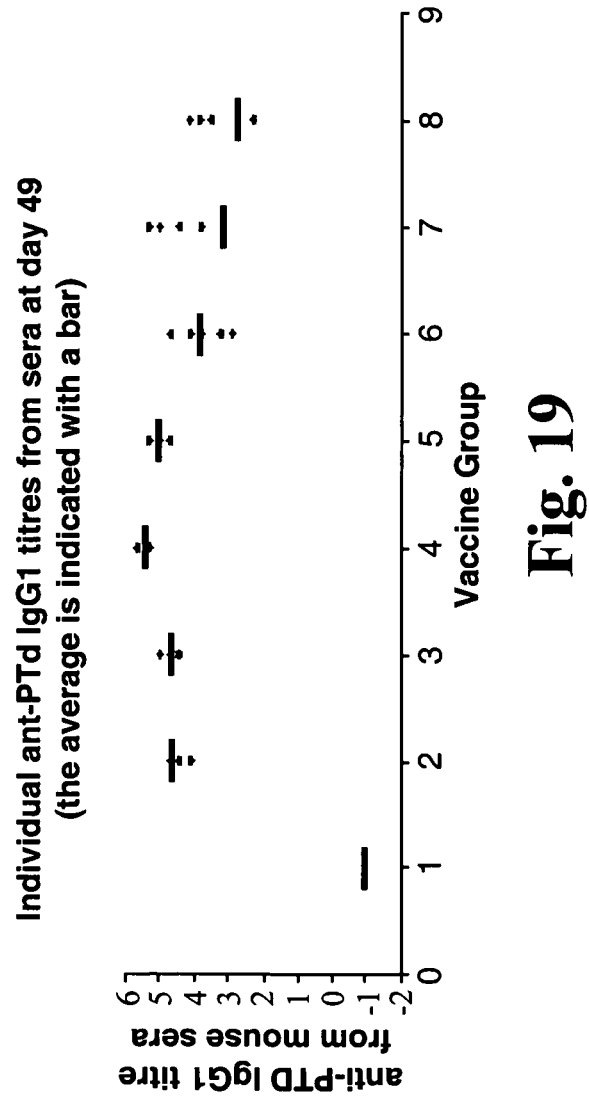
FIG. 19 shows individual IgG1 responses to vaccination with pertussis toxoid either alone or co-formulated with various adjuvants as described in the examples at day 49. Vaccine groups are as follows: 1-PBS; 2-QUADRACEL; 3-1.0 μg PTd alone; 4-1.0 μg PTd+triple adjuvant; 5-1.0 μg PTd+triple adjuvant (two doses); 6-0.2 μg PTd alone; 7-0.2 μg PTd+triple adjuvant; 8-0.2 μg PTd+triple adjuvant (two doses).
Figure 20:
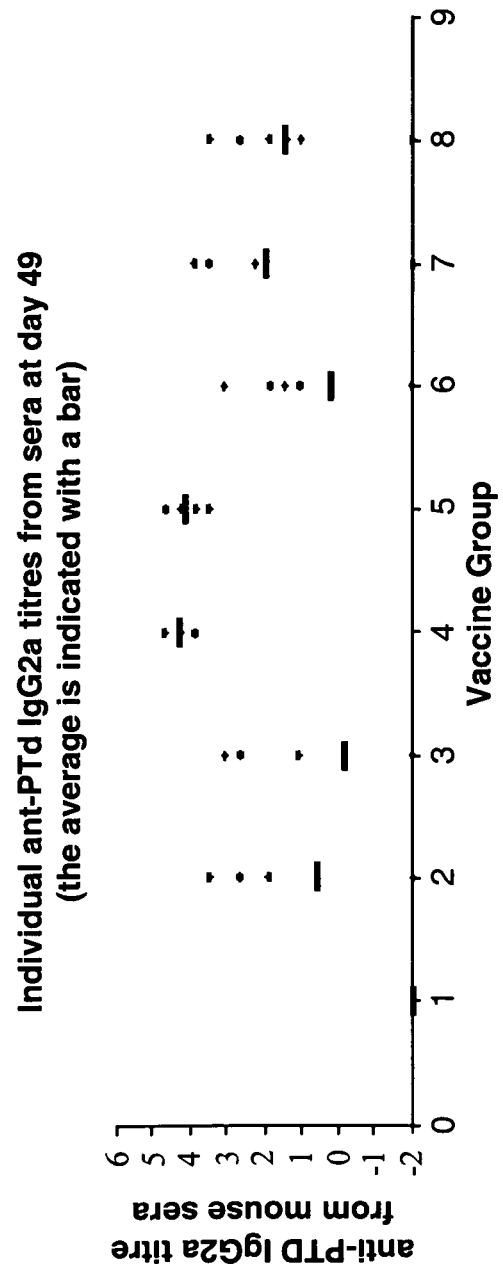
FIG. 20 shows individual IgG2a responses to vaccination with pertussis toxoid either alone or co-formulated with various adjuvants as described in the examples at day 49. Vaccine groups are as follows: 1-PBS; 2-QUADRACEL; 3-1.0 μg PTd alone; 4-1.0 μg PTd+triple adjuvant; 5-1.0 μg PTd+triple adjuvant (two doses); 6-0.2 μg PTd alone; 7-0.2 μg PTd+triple adjuvant; 8-0.2 μg PTd+triple adjuvant (two doses).
Figure 21:
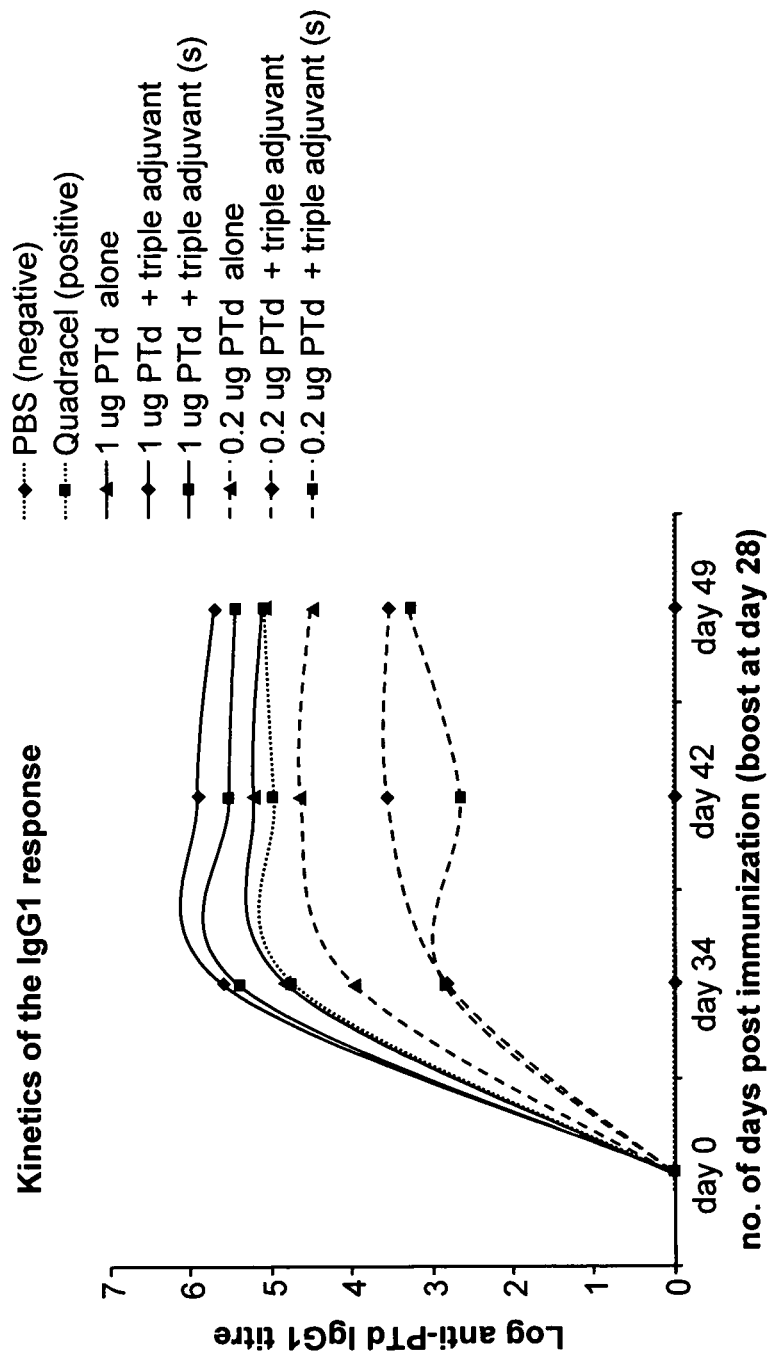
FIG. 21 shows the kinetics of the anti-PTd-specific IgG1 responses to vaccination with pertussis toxoid (PTd) either alone, or co-formulated with various adjuvants as specified. Two groups received two vaccinations of the formulation—the 1 μg PTD+triple adjuvant and 0.2 μg PTd+triple adjuvant groups.
Figure 22:
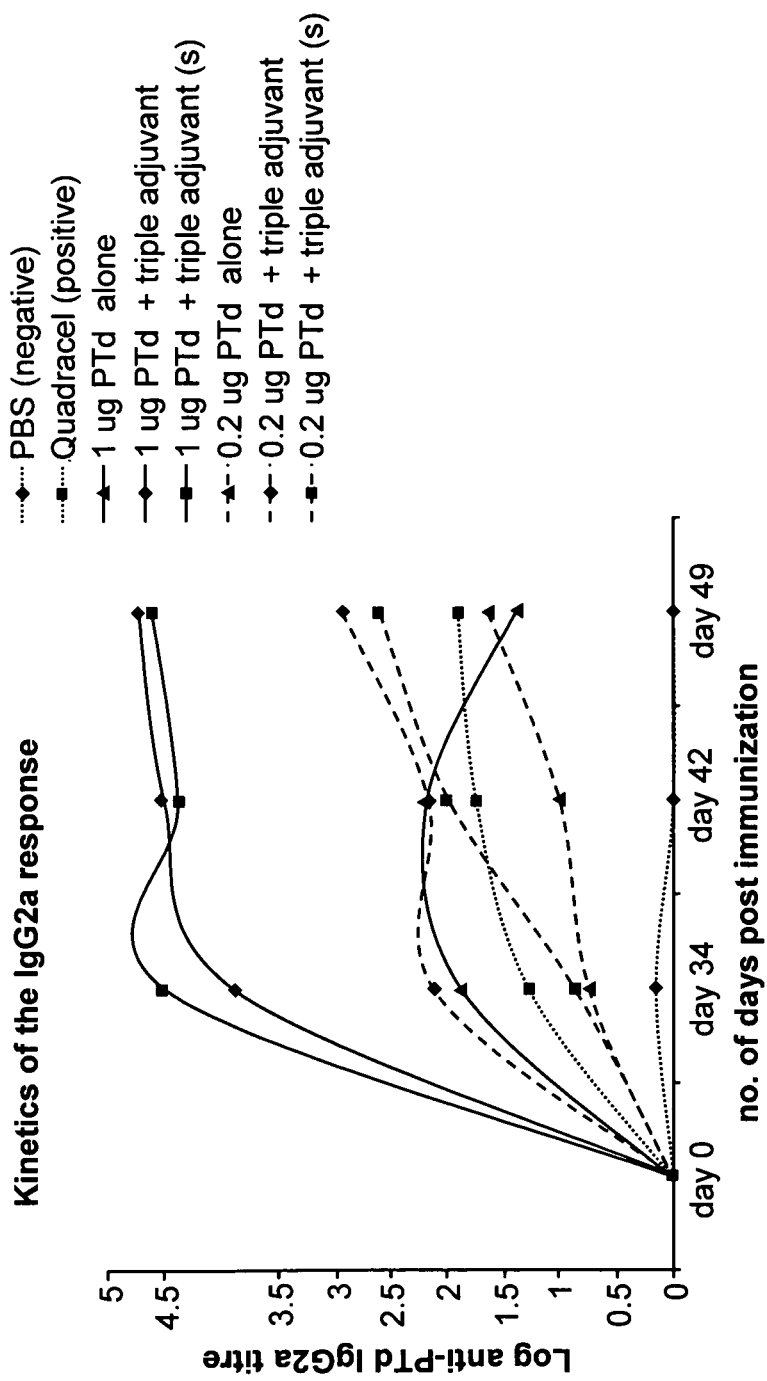
FIG. 22 shows the kinetics of the anti-PTd-specific IgG2a responses to vaccination with pertussis toxoid (PTd) either alone, or co-formulated with various adjuvants as specified. Two groups received two vaccinations of the formulation—the 1 μg PTD+triple adjuvant and 0.2 μg PTd+triple adjuvant groups.

The resulting total IgG titres showed that the immune response to the lower dose of toxoid (0.2 µg vs 1.0 µg) was more variable than to the 1.0 µg dose and that the total IgG response to the lower dose of PTd was lower at all time points (FIG. 17). However, the kinetics of the specific anti-PTd response showed that the combination adjuvants induced a much more rapid response to the PTd (FIG. 18), even when compared to the commercially available vaccine. As well, the individual IgG1 and IgG2a titres (FIGS. 19 to 22) showed that the addition of the combination adjuvants increased the specific anti-PTd IgG1 titre when 1.0 µg of PTd was used and the specific IgG2a titre at all PTd doses used. Importantly, a single dose of 1.0 µg PTd formulated together with the triple adjuvant combination induced PTd specific IgG1 titres to the same levels as two doses of the commercially available vaccine (FIG. 21). The PTd specific IgG2a titres in response to a single dose of the triple adjuvant formulation and 1.0 µg of PTd were 100 fold higher than to the commercial vaccine (FIG. 22). Thus, a single dose of the triple combination is as effective at inducing a more balanced immune response as two doses of the commercially available product.

Example 8

Chemokine Production by Human PBMCs In Vitro Following Administration of Adjuvant Formulations Comprised of CpG, Non-CpG, and Poly(I:C) Nucleic Acids, Host Defence Peptides 1002 and Nisin Z, and Polyphosphazene PCPP Chemokine Induction by Nucleic Acid-Peptide Formulations Direct complex formation between the various nucleic acids and synthetic host defense peptides was verified prior to human PBMC stimulations. For determination of the immunostimulatory activities of various nucleic acids in complex with host defense peptides in vitro, the following experiment was conducted. Various combinations of CpG ODN 10103, non-CpG ODN 5'AAAAAAGGTACCTAAATAGTAT-GTTTCTGAAA3' (SEQ ID NO:13), poly(I:C) and the synthetic host defense peptides 1002 and 1018 were examined for chemokine induction. Briefly, nucleic acids and peptide were co-incubated for 30 min at 37° C. prior to cell stimulations. Human PBMCs were stimulated with the various formulations for 24 hours and levels of MCP-1 were measured by ELISA. Optimal ratios 2:1, 1:1 and 1:2 nucleic acid:host defense peptide (µg/ml:µg/ml) were identified between concentration thresholds of 40 µg/ml and 10 µg/ml. The results were from four biological replicates.

Formulations using poly(I:C), the non-CpG ODN, and CpG 10103 all demonstrated synergistic induction of MCP-1 when coupled with the lead synthetic peptide candidates 1002 or 1018 as compared to stimulations with the individual components. Total MCP-1 release and synergistic effect were comparable regardless of the form of nucleic acid utilized in the adjuvant formulations with host defense peptide.

Chemokine Induction by Triple Adjuvant Formulations in Human PBMCs

The effect of PCPP addition on chemokine induction by peptide-CpG 10103 complexes was assessed by the induction of MCP-1 in human PBMCs. Briefly, peptide-CpG complexes were formed as previously described and following incubation PCPP, with or without MgCl$_2$ (pH 7.4), was added to the peptide-CpG complexes at various concentrations and incubated for 30 min at 37° C. Following incubation, human PBMCs were stimulated with the various formulations for 24 hours and levels of MCP-1 were measured by ELISA.

TABLE 4

Potential adjuvant properties of peptides 1002 and Nisin Z in combination with polyphosphazines (PCPP) and CpG 10103 as assessed by MCP-1 induction in human PBMC.

| Treatment | Specific details of Formulation Components | MCP-1 Induction (pg/ml) | Synergistic Induction of MCP-1* |
|---|---|---|---|
| Peptide alone (40 µg/ml) | 1002 | 371 | na |
|  | Nisin Z | 47 | na |
| CpG (20 µg/ml) | CpG 10103 | 755 | na |
| Peptide + CpG | 1002 + CpG | 8163 | 4.5 |
|  | Nisin Z + CpG | 10604 | 8.9 |
| Peptide + CpG 10103 + 1 mM MgCl$_2$ | 1002 + CpG | 11437 | 6.3 |
|  | Nisin Z + CpG | 15497 | 13 |
| 1002 + CpG 10103 + 10 mM MgCl$_2$ | 1002 + CpG | 10970 | 6.0 |
| 1002 + CpG 10103 + PCPP | PCPP (9.375 µg/ml) | 10103 | 4.4 |
|  | PCPP (18.75 µg/ml) | 10751 | 7.3 |
|  | PCPP (37.5 µg/ml) | 6169 | 4.5 |
|  | PCPP (75 µg/ml) | 0 | 0 |
|  | PCPP (150 µg/ml) | 0 | 0 |
| Nisin Z + CpG 10103 + PCPP | PCPP (9.375 µg/ml) | 11386 | 8.4 |
|  | PCPP (18.75 µg/ml) | 8506 | 7.0 |
|  | PCPP (37.5 µg/ml) | 1493 | 1.3 |
|  | PCPP (75 µg/ml) | 119 | 0.1 |
|  | PCPP (150 µg/ml) | 0 | 0 |
| 1002 + CpG 10103 + PCPP + 1 mM MgCl$_2$ | PCPP (9.375 µg/ml) | 11484 | 5.0 |
|  | PCPP (18.75 µg/ml) | 9201 | 6.2 |
|  | PCPP (37.5 µg/ml) | 3343 | 2.4 |
|  | PCPP (75 µg/ml) | 0 | 0 |
|  | PCPP (150 µg/ml) | 0 | 0 |
| Nisin Z + CpG 10103 + PCPP + 1 mM MgCl$_2$ | PCPP (9.375 µg/ml) | 10154 | 7.5 |
|  | PCPP (18.75 µg/ml) | 11505 | 9.5 |
|  | PCPP (37.5 µg/ml) | 7663 | 6.5 |
|  | PCPP (75 µg/ml) | 473 | 0.4 |
|  | PCPP (150 µg/ml) | 0 | 0 |
| 1002 + CpG 10103 + PCPP + 10 mM | PCPP (9.375 µg/ml) | 11968 | 5.2 |
|  | PCPP (18.75 µg/ml) | 12102 | 8.2 |

TABLE 4-continued

Potential adjuvant properties of peptides 1002 and Nisin Z in combination with polyphosphazines (PCPP) and CpG 10103 as assessed by MCP-1 induction in human PBMC.

| Treatment | Specific details of Formulation Components | MCP-1 Induction (pg/ml) | Synergistic Induction of MCP-1* |
|---|---|---|---|
| $MgCl_2$ | PCPP (37.5 µg/ml) | 5603 | 4.1 |
|  | PCPP (75 µg/ml) | 835 | 0.6 |
|  | PCPP (150 µg/ml) | 0 | 0 |

Peptides and CpGs were maintained at 40 µg/ml and 20 µg/ml, respectively, through all formulation experiments.
Synergistic induction of MCP-1 was calculated as follows: induction of MCP-1 by formulation/sum of MCP-1 inductions of individual components of the formulation. A number greater than 1 signifies synergistic induction of MCP-1 with higher numbers indicating improved synergy compared to the individual formulation components.
The data presented represents the average of 4 biological replicates.
*"na" = not applicable.

TABLE 5

| Group | # mice | PTd | PZ#6 | CpG-C (2395) | HH2 | Other |
|---|---|---|---|---|---|---|
| 1 | 15 |  |  |  |  | PBS-negative control |
| 2 | 15 |  |  |  |  | Quadracel-positive control |
| 3 | 15 | 1 µg |  |  |  |  |
| 4 | 15 | 1 µg | 100 µg | 10 µg | 100 µg |  |
| 5 | 15 | 1 µg | 100 µg | 10 µg | 100 µg | Two doses given |
| 6 | 15 | 0.2 µg |  |  |  |  |
| 7 | 15 | 0.2 µg | 100 µg | 10 µg | 100 µg |  |
| 8 | 15 | 0.2 µg | 100 µg | 10 µg | 100 µg | Two doses given |

Thus, novel methods for treating and preventing infectious diseases are disclosed. Although preferred embodiments of the subject invention have been described in some detail, it is understood that obvious variations can be made without departing from the spirit and the scope of the invention as defined by the claims.

The invention claimed is:

1. An adjuvant composition comprising a host defense peptide, an immunostimulatory sequence and a polyanionic polymer, wherein the polyanionic polymer is poly[di(sodium carboxylatophenoxy)phosphazene] (PCPP), poly(di-4-oxyphenylproprionate)phosphazene (PCEP), or a PCPP polymer comprising 90% PCPP copolymer with 10% hydroxyl groups (90:10 PCPP), wherein said adjuvant composition is capable of enhancing a protective immune response to a selected antigen from a pathogen as compared to the immune response elicited by an equivalent amount of the antigen when delivered without an adjuvant composition.

2. The adjuvant composition of claim 1, wherein said composition further comprises said antigen.

3. The adjuvant composition of claim 1, wherein said host defense peptide is one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:14, SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26 or SEQ ID NO:27.

4. The adjuvant composition of claim 3, wherein said host defense peptide is SEQ ID NO:19.

5. The adjuvant composition of claim 1, wherein the immunostimulatory sequence is a CpG oligonucleotide.

6. The adjuvant composition of claim 5, wherein the CpG oligonucleotide is fully phosphorothioated and is one or more of SEQ ID NO:8; SEQ ID NO:9; SEQ ID NO:10; SEQ ID NO:11 or SEQ ID NO:12.

7. The adjuvant composition of claim 1, wherein the immunostimulatory sequence is poly (I:C).

8. The adjuvant composition of claim 1, wherein the antigen is from a virus, bacteria, parasite or fungus.

9. The adjuvant composition of claim 8, wherein the antigen is from *Bordetella*.

10. The adjuvant composition of claim 9, wherein the antigen is from *B. pertussis*.

11. An adjuvant composition comprising a host defense peptide comprising the sequence of SEQ ID NO:19, a CpG oligonucleotide comprising the sequence of SEQ ID NO:12, and poly(di-4-oxyphenylproprionate)phosphazene (PCEP), wherein said adjuvant composition is in the form of a PCEP microparticle and is capable of enhancing a protective immune response to a selected antigen as compared to the immune response elicited by an equivalent amount of the antigen when delivered without an adjuvant composition.

12. The adjuvant composition of claim 11, wherein said composition further comprises a bacterial antigen.

13. The adjuvant composition of claim 11, wherein the antigen is from *Bordetella*.

14. The adjuvant composition of claim 12, wherein the antigen is from *Bordetella*.

15. The adjuvant composition of claim 13, wherein the antigen is from *B. pertussis*.

16. The adjuvant composition of claim 14, wherein the antigen is from *B. pertussis*.

17. The adjuvant composition of claim 1, wherein the adjuvant composition is in the form of a polyphosphazene microparticle.

* * * * *